United States Patent
Meyer et al.

(10) Patent No.: US 8,481,574 B2
(45) Date of Patent: Jul. 9, 2013

(54) COMPOUNDS AS CANNABINOID RECEPTOR LIGANDS

(75) Inventors: Michael D. Meyer, Lake Villa, IL (US); Michael J. Dart, Highland Park, IL (US); William A. Carroll, Evanston, IL (US); Meena V. Patel, Green Oaks, IL (US); Tedozyi Kolasa, Lake Villa, IL (US); Xueqing Wang, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 843 days.

(21) Appl. No.: 11/871,656

(22) Filed: Oct. 12, 2007

(65) Prior Publication Data

US 2008/0255123 A1  Oct. 16, 2008

Related U.S. Application Data

(60) Provisional application No. 60/851,216, filed on Oct. 12, 2006.

(51) Int. Cl.

| | | |
|---|---|---|
| A61K 31/5377 | (2006.01) | |
| A61K 31/454 | (2006.01) | |
| A61K 31/4439 | (2006.01) | |
| A61K 31/429 | (2006.01) | |
| A61K 31/428 | (2006.01) | |
| A61K 31/427 | (2006.01) | |
| A61K 31/426 | (2006.01) | |
| C07D 513/04 | (2006.01) | |
| C07D 417/06 | (2006.01) | |
| C07D 417/12 | (2006.01) | |
| C07D 277/60 | (2006.01) | |
| C07D 277/58 | (2006.01) | |
| C07D 277/56 | (2006.01) | |
| C07D 277/30 | (2006.01) | |
| C07D 277/28 | (2006.01) | |
| C07D 277/26 | (2006.01) | |
| C07D 277/24 | (2006.01) | |

(52) U.S. Cl.
USPC ........ 514/365; 514/342; 514/367; 514/236.8; 514/326; 544/133; 546/209; 546/269.7; 548/153; 548/152; 548/200; 548/201; 548/146

(58) Field of Classification Search
USPC ....... 514/365, 342, 367, 236.8, 326; 544/133; 546/209, 269.7; 548/153, 152, 200, 201, 548/146
See application file for complete search history.

(56) References Cited

U.S. PATENT DOCUMENTS 4,966,828 A * 10/1990 Doenges et al. ........... 430/281.1
5,055,579 A * 10/1991 Pawlowski et al. ........... 544/216
2004/0029040 A1  2/2004  Watanabe et al.

FOREIGN PATENT DOCUMENTS

| CA | 2587667 | | 5/2006 |
|---|---|---|---|
| DE | 1522361 | A1 | 7/1969 |
| DE | 1772867 | A1 | 6/1971 |
| DE | 2458933 | A1 | 6/1975 |
| EP | 1060734 | A2 | 12/2000 |
| EP | 1219612 | A1 | 7/2002 |
| WO | WO-03097605 | A1 | 11/2003 |
| WO | WO-2005058887 | A1 | 6/2005 |
| WO | WO-2007140385 | A2 | 12/2007 |
| WO | WO-2007140439 | A2 | 12/2007 |

OTHER PUBLICATIONS

Rautio et al. Nature Reviews Drug Discovery 2008, 7, pp. 255-270.*
Wang et al. Drug Delivery: Principles and Applications, 2005 John Wiley & Sons, Inc. Publication, Section 8.3, pp. 136-137.*
Smith, D. A. Current Opinion in Drug Discovery & Development 2007, 10, 550-559.*
Testa, B. Current Opinion in Chemical Biology 2009, 13, pp. 338-344.*
"IUPAC Commission on Nomenclature of Organic Chemistry Rules for the Nomenclature of Organic Chemistry, Section E: Stereochemistry (Recommendations 1974)," Pure Appl Chem, 1976, 13-30, vol. 45.
Ansell M.F. and Mason J.S., "The Synthesis of (+/−)-10a-Homo-11a-carbathromboxane A1, a Stable Thromboxane A Analogue," J Chem Soc Perkin Trans I, 1984, 1061-1068.
Arevalo-Martin, A., et al., "Therapeutic Action of Cannabinoids in a Murine Model of Multiple Sclerosis," Journal of Neuroscience, 2003, 2511-2516, vol. 23, No. 7.
Benito, C, et al., "A Glial Endogenous Cannabinoid System Is Upregulated in the Brains of Macaques with Simian Immunodeficiency Virus-Induced Encephalitis," Journal of Neuroscience, 2005, 2530-2536, vol. 25—Issue 10.

(Continued)

Primary Examiner — Joseph Kosack
Assistant Examiner — Matthew Coughlin
(74) Attorney, Agent, or Firm — Lisa V. Mueller; Michael Best & Friedrich LLP

(57) ABSTRACT

The present invention relates to compounds of formula (I)

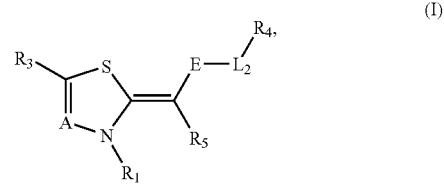

(I)

wherein A, E, $L_2$, $R_1$, $R_3$, $R_4$ and $R_5$ are as defined in the herein, compositions comprising such compounds, and methods of treating conditions and disorders using such compounds and compositions.

15 Claims, No Drawings

OTHER PUBLICATIONS

Benito, C. et al., "Cannabinoid CB2 Receptors and Fatty Acid Amide Hydrolase are Selectively Overexpressed in Neuritic Plaque-Associated Glia in Alzheimer's Disease Brains," Journal of Neuroscience, 2003, 11136-11141, vol. 23—Issue 35.

Berge, S.M. et al., "Journal of Pharmaceutical Sciences, Pharmaceutical Salts," J Pharmaceutical Sciences, 1977, 1-19, vol. 66.

Bouchard, J-F et al., "Contribution of endocannabinoids in the endothelial protection afforded by ischemic preconditioning in the isolated rat heart", Life Sciences, 2003, 1859-1870, vol. 72.

Boyle, W.J. et al., "Osteoclast differentiation and activation," (Binary/Image), 2003, 337-342, vol. 423.

Brennan, T.J. et al., "Characterization of a rat model of incisional pain," (Binary/Image), 1996, 493-501, vol. 64.

Bruson H.A. and Eastes J.W., "Action of Sulfuric Acid upon Unsaturated Isothiocyanates: Mercaptothiazolines," J. Am. Chem. Soc, 1937, 2011-2013, vol. 59—Issue 10.

Buckley, N.E. et al., "Immunomodulation by cannabinoids is absent in mice deficient for the cannabinoid CB receptor," European Journal of Pharmacology, 2000, 141-149, vol. 396.

Carrier, E.J. et al., "Endocannabinoids in Neuroimmunology and Stress," Current Drug Targets CNS and Neurological Disorders, 2005, 657-665, vol. 4.

Casanova, M.L. et al., "Inhibition of skin tumor growth and angiogenesis in vivo by activation of cannabinoid receptors," Journal of Clinical Investigation, 2003, 43-50, vol. 111.

Chaplan, S.R. et al., "Quantitative assessment of tactile allodynia in the rat paw," Journal of Neuroscience Methods, 1994, 55-63, vol. 53.

Cichewicz, D.L. et al., "Synergistic interactions between cannabinoid and opioid analgesics," Life Sciences, 2004, 1317-1324, vol. 74.

Clayton, N. et al., "CB1 and CB2 cannabinoid receptors are implicated in inflammatory pain," (Binary/Image), 2002, 253-260, vol. 96.

Dawood et al., "Synthesis, anticonvulsant, and anti-inflammatory evaluation of some new benzotriazole and benzofuran-based heterocycles", Bioorganic and Medicinal Chemistry, 2006, vol. 14—Issue 11, 3672-3680.

Dixon, W.J. "Efficient analysis of experimental observations," Annual Review of Pharmacology and Toxicology, 1980, 441-462, vol. 20.

Filippo, C.D. et al., "Cannabinoid CB2 receptor activation reduces mouse myocardial ischemia-reperfusion injury: involvement of cytokine/chemokines and PMN," Journal of Leukocyte Biology, 2004, 453-459, vol. 75.

Galiégue, et al., "Expression of central and peripheral cannabinoid receptors in human immune tissues and leukocyte subpopulations," European Journal of Biochemistry, 1995, 54-61, vol. 232.

Golech, S.A. et al., "Human brain endothelium: coexpression and function of vannilloid and endocannabinoid receptors," Molecular Brain Research, 2004, 87-92, vol. 132.

Greene, T.W. et al., "Protective Groups in Organic Synthesis", 1999, 3 rd Ed, 494-653.

Grotenhermen, F. et al., "IACM 2nd Conference on Cannabinoids in Medicine," Expert Opinion in Pharmacotherapy, 2003, 2367-2371, vol. 4—Issue 12.

Hanus, L. et al., "HU-308: A specific agonist for CB 2, a peripheral cannabinoid receptor," Proceedings of the National Academy of Science, 1999, 14228-14233, vol. 96.

Hohmann, A.G. et al., "Selective Activation of Cannabinoid CB2 Receptors Suppresses Hyperalgesia Evoked by Intradermal Capsaicin," Journal of Pharmacology and Experimental Therapeutics, 2004, 446-453, vol. 308.

Ibrahim, M.M. et al., "Activation of CB2 cannabinoid receptors by AM1241 inhibits experimental neuropathic pain: Pain inhibition by receptors not present in the CNS," Proceedings of the National Academy of Science, 2003, 10529-10533, vol. 100—Issue 18.

Ibrahim, M.M. et al., "CB2 cannabinoid receptor activation produces antinociception by stimulating peripheral release of endogenous opioids," Proceedings of the National Academy of Science, 2005, 3093-3098, vol. 102—Issue 8.

Idris, A.I. et al., "Regulation of bone mass, bone loss and osteoclast activity by cannabinoid receptors," Nature Medicine, 2005, 774-779, vol. 11—Issue 7.

Ihenetu, K. et al., "Inhibition of interleukin-8 release in the human colonic epithelial cell line HT-29 by cannabinoids," European Journal of Pharmacology, 2003, 207-215, vol. 458.

International Search Report for application No. PCT/US07/081263, Mailed on Nov. 27, 2008, 3 pages.

Joshi S.K. et al., "Comparison of Antinociceptive Actoins of Standard Analgesics in Attenuating Capsaicin and Nerve-Injury-Induced Mechanical Hypersensitivty," Neurosci, 587-596, vol. 143, 2006.

Julien, B, et al., "Antifibrogenic Role of the Cannabinoid Receptor CB2 in the Liver," Gastroenterology, 2005, 742-755, vol. 128.

Karsak, M, et al., "Cannabinoid receptor type 2 gene is associated with human osteoporosis," Human Molecular Genetics, 2005, 3389-3396, vol. 14—Issue 22.

Kim, S.H. and Chung, J.M. "An experimental model for peripheral neuropathy produced by segmental spinal nerve ligation in the rat," (Binary/Image), 1992, 355-363, vol. 50—Issue 3.

Kreutzberg, G W "Microglia: a sensor for pathological events in the CNS," Trends in Neuroscience, 1996, 312-318, vol. 19.

Lepicier, P. et al., "Endocannabinoids protect the rat isolated heart against ischaemia," British Journal of Pharmacology, 2003, 805-815, vol. 139.

Lotersztajn, S. et al., "Hepatic Fibrosis: Molecular Mechanisms and Drug Targets," Annual Review of Pharmacology and Toxicology, 2005, 605-628, vol. 45.

Malan, T.P. et al., "CB2 cannabinoid receptor-mediated peripheral antinociception," (Binary/Image), 2001, 239-245, vol. 93.

Maresz, K, et al., "Modulation of the cannabinoid CB2 receptor in microglial cells in response to inflammatory stimuli," Journal of Neurochemistry, 2005, 437-445, vol. 95.

Mathison, R, et al., "Effects of cannabinoid receptor-2 activation on accelerated gastrointestinal transit in lipopolysaccharide-treated rats," British Journal of Pharmacology, 2004, 1247-1254, vol. 142.

McKallip, R.J. et al., "Targeting CB2 cannabinoid receptors as a novel therapy to treat malignant lymphoblastic disease," (Binary/Image), 2002, 637-634, vol. 100.

Meyers A.I. and Ford M.E., "Oxazolines. XX. Synthesis of Achiral and Chiral Thiiranes and Olefins by Reaction of Carbonyl Compounds with 2-(Alkylthio)-2-oxazolines," J. Org. Chem, 1735-1742, vol. 41—Issue 10, 1976.

Molina-Holgado, F. et al., "Endogenous Interleukin-1 Receptor Antagonist Mediates Anti-Inflammatory and Neuroprotective Actions of Cannabinoids in Neurons and Glia," Journal of Neuroscience, 2003, 6470-6474, vol. 23—Issue 16.

Nackley, A.G. et al., "Selective activation of cannabinoid CB2 receptors suppresses spinal fos protein expression and pain behavior in a rat model of inflammation," Neuroscience, 2003, 747-757, vol. 119.

Ni, X. et al., "Win 55212-2, a cannabinoid receptor agonist, attenuates leukocyte/endothelial interactions in an experimental autoimmune encephalomyelitis model," Multiple Sclerosis, 2004, 158-164, vol. 10.

Nunez, E. et al., "Cannabinoid CB2 Receptors are Expressed by Perivascular Microglial Cells in the Human Brain: An Immunohistochemical Study," Synapse, 2004, 208-213, vol. 53.

Partch, Ret al., "2-Oxaadamantane-1-N,N,N-trimethylmethanaminium Iodide:1 Synthesis and Potential for Muscarinic Activity," Croatia Chemical Acta, 1985, 661-66, vol. 58—Issue 4.

Patel, J.J. et al., "Inhibition of guinea-pig and human sensory nerve activity and the cough reflex in guinea-pigs by cannabinoid (CB2) receptor activation," British Journal of Pharmacology, 2003, 261-268, vol. 140.

Pertwee, R.G. "Cannabinoids and multiple sclerosis," Pharmacology and Therapeutics, 2002, 165-174, vol. 95.

Prescott, et al., "Lipid Vesicles as Carriers for Introducing Biologically Active Materials into Cells," Methods in Cell Biology, 1976, 33-71, vol. 14, Academic Press.

Quartilho, A. et al., "Inhibition of Inflammatory Hyperalgesia by Activation of Peripheral CB2 Cannabinoid Receptors," Anesthesiology, 2003, 955-960, vol. 99.

Ralston, S.H. "Genetic determinants of susceptibility to osteoporosis," Current Opinion in Pharmacology, 2003, 286-290, vol. 3.

Ralston, S.H. "Regulation of bone mass, bone loss and osteoclast activity by cannabinoid receptors," Nature Medicine, 2005, 774-779, vol. 11.

Ramirez, B.G. et al., "Prevention of Alzheimer's Disease Pathology by Cannabinoids: Neuroprotection Mediated by Blockade of Microglial Activation," Journal of Neuroscience, 2005, 1904-1913, vol. 25—Issue 8.

Sanchez C. et al., "Inhibition of Glioma Growth in Vivo by Selective Activation of the CB2 Cannabinoid Receptor1," Cancer Research, 2001, 5784-5789, vol. 61.

Steffens S. et al., "Low dose oral cannabinoid therapy reduces progression of atherosclerosis in mice," (Binary/Image), 2005, 782-786, vol. 434.

Valenzano K.J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, 658-672, vol. 48.

Walter L. et al., "Cannabinoids and neuroinflammation," Pharmacology, 2004, 775-785, vol. 141.

Warhurst A.C. et al., "Interferon ? induces differential upregulation of α and β chemokine secretion in colonic epithelial cell lines," (Binary/Image), 1998, 208-213, vol. 42.

Watkins L.R. et al, "Glial activation: a driving force for pathological pain," Trends in Neuroscience, 2001, 450-455, vol. 24—Issue 8.

Weyer et al., "Blutzuckersenkende Chinolin-8-carboxamidoalkyl-benzol sulfonamid derivate", Arzneimittel-Forschung, 1974, vol. 24, 269-275.

Williams K. et al., "Central nervous system perivascular cells are immunoregulatory cells that connect the CNS with the peripheral immune system," (Binary/Image), 2001, 156-164, vol. 36.

Wright K. et al., "Differential Expression of Cannabinoid Receptors in the Human Colon: Cannabinoids Promote Epithelial Wound Healing," Gastroenterology, 2005, 437-453, vol. 129.

Yoshihara S. et al., "Cannabinoid Receptor Agonists Inhibit Sensory Nerve Activation in Guinea Pig Airways", American Journal of Respiratory and Critical Care Medicine, 2004, 941-946, vol. 170.

Yoshihara S. et al., "Endogenous Cannabinoid Receptor Agonists Inhibit Neurogenic Inflammations in Guinea Pig Airways" Allergy and Immunology, 2005, 80-87, vol. 138.

Yoshihara S. et al., "The Cannabinoid Receptor Agonist Win 55212-2 Inhibits Neurogenic Inflammations in Airway Tissues," Journal of Pharmacological Sciences, 2005, 77-82, vol. 98—Issue 1.

Zimmer, A et al., "Increased mortality, hypoactivity, and hypoalgesia in cannabinoid CB1 receptor knockout mice," Proceedings of the National Academy of Science, 1999, 5780-5785, vol. 96.

International Preliminary Report on Patentability and Written Opinion for Application No. PCT/US07/081263, mailed on Apr. 15, 2010, 8 pages.

* cited by examiner

COMPOUNDS AS CANNABINOID RECEPTOR LIGANDS

This application claims priority to U.S. Patent Application Ser. No. 60/851,216 filed Oct. 12, 2006 and is incorporated herein by reference.

TECHNICAL FIELD

The present invention relates to compounds that are $CB_2$ receptor ligands, compositions comprising such compounds, and methods of treating conditions and disorders using such compounds and compositions.

BACKGROUND OF THE INVENTION (−)-$\Delta^9$-Tetrahydrocannabinol ($\Delta^9$-THC), the major psychoactive constituent of marijuana, exerts a broad range of biological effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

Accordingly, the need exists to further explore and develop $CB_2$ receptor ligands that exhibit immunomodulatory and anti-inflammatory properties. These $CB_2$ receptors ligands will offer a unique pharmacotherapy for the treatment of immune and inflammatory disorders.

SUMMARY OF THE INVENTION

The present invention generally provides compounds that are $CB_2$ receptor ligands and pharmaceutical compositions and methods for the treatment of disorders using these compounds and pharmaceutical compositions.

In one embodiment, the present invention provides compounds of formula (I), or pharmaceutically acceptable salts, prodrugs, salts of prodrugs, or combinations thereof,

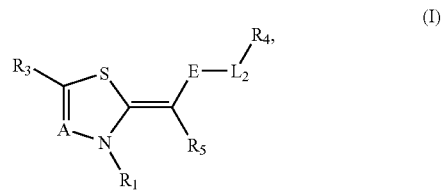

wherein
A is N or $C(R_2)$;
E is C(O) or C(S);
$R_1$ is $C_3$-$C_7$ alkyl, alkenyl, alkoxy-($C_2$-$C_6$ alkylene)-, alkoxycarbonylalkyl, alkylcarbonylalkyl, alkylsulfinylalkyl, alkylsulfonylalkyl, alkylthioalkyl, alkynyl, aryloxy-($C_2$-$C_6$ alkylene)-, arylalkoxy-($C_2$-$C_6$ alkylene)-, arylcarbonyloxy-($C_2$-$C_6$ alkylene)-, carboxyalkyl, cycloalkyl, cycloalkylalkyl, cyanoalkyl, haloalkyl, haloalkoxy-($C_2$-$C_6$ alkylene)-, heteroaryl, heteroarylalkyl, heteroaryloxy-($C_2$-$C_6$ alkylene)-, heteroarylcarbonyloxy-($C_2$-$C_6$ alkylene)-, heterocycle, heterocyclealkyl, heterocycleoxy-($C_2$-$C_6$ alkylene)-, hydroxy-($C_2$-$C_6$ alkylene)-, $R_aR_bN$—($C_2$-$C_6$ alkylene)-, $R_cR_dN$—C(O)-alkylene-, $R_cR_dN$—C(O)—$NR_c$—($C_2$-$C_6$ alkylene)-, $R_eO$—N=$C(R_z)$-alkylene-, or $R_fR_gN$—N=$C(R_z)$-alkylene-;

$R_2$ and $R_3$ are each independently hydrogen, alkenyl, alkoxy, alkoxyalkyl, alkoxycarbonyl, alkoxycarbonylalkyl, alkyl, alkynyl, alkylcarbonyl, alkylsulfinyl, alkylsulfonyl, alkylthio, aryl, arylalkyl, arylalkenyl, azidoalkyl, cyano, cycloalkyl, formyl, halogen, haloalkyl, heteroaryl, heterocycle, hydroxyalkyl, hydroxyalkynyl, hydroxyhaloalkyl, $R_jR_kN$—, $R_jR_kN$-alkylene-, $R_mR_nN$—C(O)—, $R_pO$—N═C($R^z$)-alkylene-, $R_pO$—N═C($R^z$)—, or $R_rR_sN$—N═C($R^z$)-alkylene-, or $R_2$ and $R_3$ taken together with the carbon atoms to which they are attached form an aryl, a heteroaryl, a heterocycle, or a cycloalkenyl ring;

$R_4$ is $C_4$-$C_{10}$ alkyl, wherein the $C_4$-$C_{10}$ alkyl group is optionally substituted with one substituent selected from the group consisting of hydroxy, alkoxy, haloalkoxy, cyano, —C(O)N($R^z$)$_2$, and —N($R^z$)C(O)$R^z$; alkenyl, alkynyl, naphthyl, arylalkyl, cycloalkyl, cycloalkylalkyl, cycloalkenyl, cycloalkenylalkyl, haloalkyl, heteroaryl, heteroarylalkyl, heterocycle, heterocyclealkyl, wherein the naphthyl, cycloalkyl, cycloalkenyl, heteroaryl, heterocycle, the aryl moiety of the arylalkyl, the cycloalkyl moiety of the cycloalkylalkyl, the cycloalkenyl moiety of the cycloalkenylalkyl, the heteroaryl moiety of the heteroarylalkyl, and the heterocycle moiety of the heterocyclealkyl are each independently unsubstituted or substituted with 1, 2, 3, 4, 5, or 6 substituents as represented by $R_6$;

or phenyl substituted with 1, 2, 3, 4, or 5 substituents as represented by $R_6$;

$R_6$, at each occurrence, is independently selected from the group consisting of alkyl, alkenyl, alkynyl, nitro, cyano, halogen, haloalkyl, oxo, —$OR_{eu}$, —O—$(CR_{ju}R_{ku})_x$—N($R_{wu}$)$_2$, —OC(O)$R_{eu}$, —$SR_{eu}$, —S(O)$R_{fu}$, —S(O)$_2R_{fu}$, —S(O)$_2$N($R_{wu}$)($R_{gu}$), —N($R_{wu}$)($R_{gu}$), —N($R_{wu}$)C(O)$R_{eu}$, —N($R^{wu}$)C(O)O$R_{eu}$, —N($R_{wu}$)S(O)$_2R_{fu}$, —N($R_{wu}$)C(O)N($R_{wu}$)($R_{gu}$), —N($R_{wu}$)S(O)$_2$N($R_{wu}$)($R_{gu}$), —C(O)$R_{eu}$, —C(O)O($R_{eu}$), —C(O)N($R_{wu}$)($R_{gu}$), haloalkyl, —$(CR_{ju}R_{ku})_x$—CN, —$(CR_{ju}R_{ku})_x$—$OR_{eu}$, —$(CR_{ju}R_{ku})_x$—OC(O)$R_{eu}$, —$(CR_{ju}R_{ku})_x$—$SR_{eu}$, —$(CR_{ju}R_{ku})_x$—S(O)$R_{fu}$, —$(CR_{ju}R_{ku})_x$—S(O)$_2R_{fu}$, —$(CR_{ju}R_{ku})_x$—N($R_{wu}$)($R_{gu}$), —$(CR_{ju}R_{ku})_x$—N($R_{wu}$)C(O)$R_{eu}$, —$(CR_{ju}R_{ku})_x$—N($R_{wu}$)S(O)$_2R_{fu}$, —$(CR_{ju}R_{ku})_x$—N($R_{wu}$)C(O)N($R_{wu}$)($R_{gu}$), —$(CR_{ju}R_{ku})_x$—N($R_{wu}$)S(O)$_2$N($R_{wu}$)($R_{gu}$), —$(CR_{ju}R_{ku})_x$—C(O)$R_{eu}$, —$(CR_{ju}R_{ku})_x$—C(O)O($R_{eu}$), —$(CR_{ju}R_{ku})_x$—C(O)N($R_{wu}$)($R_{gu}$), —C($R_{wu}$)═N—$OR_{wu}$, aryl, heteroaryl, cycloalkyl, and heterocycle;

$R_{wu}$, at each occurrence, is independently hydrogen, alkyl, or haloalkyl;

$R_{eu}$ and $R_{gu}$, at each occurrence, are each independently hydrogen, alkyl, alkoxyalkyl, cycloalkyl, cycloalkylalkyl, heterocycle, haloalkoxyalkyl, or haloalkyl; wherein the cycloalkyl, the heterocycle, and the cycloalkyl moiety of the cycloalkylalkyl are each independently unsubstituted or substituted with 1, 2, 3, 4, 5 or 6 substituents selected from the group consisting of alkyl, halogen, and haloalkyl;

$R_{fu}$, at each occurrence, is independently alkyl or haloalkyl;

$R_{ju}$ and $R_{ku}$, at each occurrence, are each independently hydrogen, halogen, alkyl, or haloalkyl;

x is 1, 2, 3, 4, or 5;

$R_5$ is hydrogen, alkyl, alkenyl, alkynyl, cyano, or halogen;

$L_2$ is a bond, —N($R_e$)— or —O—;

$R_a$ and $R_b$ are each independently selected from group consisting of hydrogen, alkyl, alkylcarbonyl, alkylsulfonyl, alkoxycarbonyl, aryl, arylalkyl, cycloalkyl, cycloalkylalkyl, heteroaryl, heteroarylalkyl, heterocycle, or heterocyclealkyl;

$R_c$ and $R_d$, at each occurrence, are each independently hydrogen, alkyl, or haloalkyl;

$R_e$, at each occurrence, is independently hydrogen, alkyl, alkenyl, alkoxyalkyl, alkynyl, cyanoalkyl, cycloalkyl, cycloalkylalkyl, haloalkyl, or hydroxyalkyl;

$R_f$ and $R_g$, are each independently hydrogen, alkyl, alkenyl, alkoxyalkyl, alkoxycarbonyl, alkynyl, arylalkyl, cyanoalkyl, cycloalkylalkyl, haloalkyl, heteroarylalkyl, heterocyclealkyl, hydroxyalkyl or nitroalkyl; or $R_f$ and $R_g$, together with the nitrogen atom to which they are attached, form a 5-, 6-, or 7-membered heterocycle ring;

$R_j$ and $R_k$, at each occurrence, are each independently hydrogen, alkyl, alkoxycarbonyl, alkylcarbonyl, alkylsulfonyl, arylalkyl, or —C(O)N($R^z$)$_2$;

$R_m$ and $R_n$ are each independently hydrogen, alkyl, or haloalkyl;

$R_p$, at each occurrence, is independently hydrogen, alkyl, alkenyl, alkoxyalkyl, alkynyl, cyanoalkyl, cycloalkylalkyl, haloalkyl, heterocyclealkyl, hydroxyalkyl, or nitroalkyl;

$R_r$ and $R_s$ are each independently hydrogen, alkyl, alkenyl, alkoxyalkyl, alkynyl, cyanoalkyl, cycloalkylalkyl, haloalkyl, heterocyclealkyl, hydroxyalkyl, or nitroalkyl; or $R_r$ and $R_s$, together with the nitrogen atom to which they are attached, form a 5-, 6-, or 7-membered heterocycle ring; and $R_z$, at each occurrence, is independently hydrogen, alkyl, or haloalkyl;

with the proviso that when A is —C($R_2$), $R_2$ is hydrogen or $C_1$-$C_5$ alkyl, $R_3$ is hydrogen or phenyl, E is C(O), $L_2$ is a bond, and $R_4$ is aryl, then $R_1$ is not $C_3$-$C_5$ alkyl, $C_2$-$C_5$ alkenyl, $C_2$-$C_5$ alkynyl, or 4-amino-2-methyl-5-pyrimidinyl)methyl.

In another embodiment, the present invention provides a method for treating pain (for example, neuropathic pain or nociceptive pain) in a mammal in need of such treatment. The method comprises administering to the mammal a therapeutically effective amount of a compound of formula (I) or a pharmaceutically acceptable salt thereof.

In yet another embodiment, the present invention provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of formula (I) or a pharmaceutically acceptable salt thereof.

Another embodiment of the present invention relates to a method for providing neuroprotection in a mammal in need of such treatment. This method comprises administering to the mammal a therapeutically effective amount of a compound of formula (I) or a pharmaceutically acceptable salt thereof.

Yet another embodiment of the present invention relates to a method of treating an autoimmune disease selected from the group consisting of multiple sclerosis, rheumatoid arthritis, systemic lupus, myasthenia gravis, type I diabetes, irritable bowel syndrome, psoriasis, psoriatic arthritis, and hepatitis, in a mammal in need of such treatment comprising administering to the mammal a therapeutically effective amount of a compound of formula (I) or a pharmaceutically acceptable salt thereof.

Yet another embodiment of the present invention relates to a method of treating an immune related disorder including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome in a mammal in need of such treatment comprising administering to the mammal a therapeutically effective amount of a compound of formula (I) or a pharmaceutically acceptable salt thereof.

Yet another embodiment of the present invention relates to a method of treating a disorder selected form the group consisting of Alzheimer's disease, encephalomyelitis, inflammatory bowel disease, hepatic fibrosis, cough, asthma, osteoporosis, arthrosclerosis, ischemia, myocardial infarction in a mammal in need of such treatment comprising administering to the mammal a therapeutically effective amount of a compound of Formula (I) or a pharmaceutically acceptable salt thereof.

In another embodiment, the present invention provides a pharmaceutical composition comprising a therapeutically effective amount of a compound of the invention or a pharmaceutically acceptable salt thereof in combination with one or more pharmaceutically acceptable carriers. The composition is preferably useful for the treatment of the disease conditions described above.

Further, the present invention provides the use of a compound of formula (I) or a pharmaceutically acceptable salt thereof, in the manufacture of a medicament for the treatment of the disease conditions described above.

Yet further, the present invention provides a method of treating a disorder wherein the disorder is ameliorated by modulating the cannabinoid receptor type 2 ($CB_2$) receptor in a host mammal in need of such treatment comprising administering a therapeutically effective amount of a compound of formula (I) or a pharmaceutically acceptable salt thereof.

These and other objects of the invention are described in the following paragraphs. These objects should not be deemed to narrow the scope of the invention.

DETAILED DESCRIPTION

Compounds of formula (I) are disclosed in this invention,

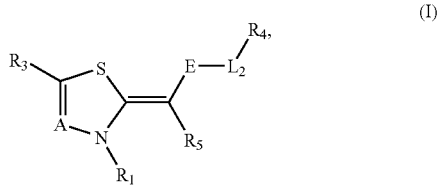

(I)

wherein $R_1$, A, $R_3$, $L_2$, E, $R_4$, and $R_5$ are as defined above in the Summary of the Invention and below in the Detailed Description. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. DEFINITIONS

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, isopropenyl, and 3-decenyl. The term "$C_2$-$C_5$ alkenyl" as used herein, means a straight or branched chain hydrocarbon containing from 2 to 5 carbons and containing at least one carbon-carbon double bond.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended to the parent molecular moiety through a sulfonyl group, as defined herein.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpropyl, 2,2-dimethylpentyl, 2,3-dimethylpentyl, n-heptyl, n-octyl, n-nonyl, and n-decyl. The term "$C_3$-$C_5$ alkyl" as used herein, means a straight or branched chain hydrocarbon containing from 3 to 5 carbon atoms. The term "$C_3$-$C_7$ alkyl" as used herein, means a straight or branched chain hydrocarbon containing from 3 to 7 carbon atoms. The term "$C_4$-$C_{10}$ alkyl" as used herein, means a straight or branched chain hydrocarbon containing from 4 to 10 carbon atoms.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkylene group, as defined herein. Representative examples of alkylcarbonylalkyl include, but are not limited to, 2-oxopropyl, 3,3-dimethyl-2-oxopropyl, 3-oxobutyl, 3,3-dimethyl-2-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, —$CH_2CH_2C(CH_3)(H)$—, —$C(C_2H_5)_2$—, and —$CH_2CH(CH_3)CH_2$—. The term "$C_2$-$C_6$ alkylene" means a divalent group derived from a straight or branched chain hydrocarbon of from 2 to 6 carbon atoms.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkylene group, as defined herein.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 3-methylbut-1-ynyl, 2-pentynyl, and 1-butynyl. The term "$C_2$-$C_5$ alkynyl" as used herein, means a straight or branched chain hydrocarbon containing from 2 to 5 carbons and containing at least one carbon-carbon triple bond.

The term "aryl," as used herein, means phenyl, a bicyclic aryl or a tricyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryls include, but are not limited to, anthracene, phenanthrene, dihydroanthracenyl, fluorenyl, 1,2-dihydroacenaphthylenyl, and tetrahydrophenanthrenyl. The phenyl, bicyclic and tricyclic aryls are attached to the parent molecular moiety through any carbon atom contained within the phenyl, bicyclic and tricyclic aryls respectively.

The term "arylalkenyl" as used herein, means an aryl group, as defined herein, appended to the parent molecular moiety through an alkenyl group, as defined herein.

The term "arylalkoxy" as used herein, refers to an arylalkyl group, as defined herein, appended to the parent molecular moiety through an oxygen atom.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "arylcarbonyl" as used herein, refers to an aryl group, as defined herein, appended to the parent molecular moiety through a carbonyl group.

The term "arylcarbonyloxy" as used herein, refers to an arylcarbonyl group, as defined herein, appended to the parent molecular moiety through an oxygen atom. Representative example of arylcarbonyloxy includes, but not limited to, phenylcarbonyloxy.

The term "aryloxy" as used herein, refers to an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "azido" as used herein, means a —$N_3$ group.

The term "azidoalkyl" as used herein, means an azido group, as defined herein, appended to the parent molecular moiety through an alkylene group, as defined herein.

The term "carbonyl" as used herein, means a —C(O)— group.

The term "carboxy" as used herein, means a —$CO_2H$ group.

The term "carboxyalkyl" as used herein, means a carboxy group, as defined herein, appended to the parent molecular moiety through an alkylene group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein, means a monocyclic or bicyclic ring system containing zero heteroatoms in the ring. The monocyclic cycloalkenyl has three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. Bicyclic cycloalkenyls are exemplified by a monocyclic cycloalkenyl fused to a monocyclic cycloalkyl, or a monocyclic cycloalkenyl fused to a monocyclic cycloalkenyl. Representative examples of bicyclic ring systems include, but are not limited to 3a,4,5,6,7,7a-hexahydro-1H-indenyl, 4,5,6,7-tetrahydro-3aH-indene, and octahydronaphthalenyl. The cycloalkenyl groups of the present invention are appended to the parent molecular moiety through any substitutable carbon atom within the groups, and may contain one or two alkylene bridges of 1, 2, 3, or 4 carbon atoms, wherein each bridge links two non-adjacent atoms within the groups.

The term "cycloalkenylalkyl" as used herein, means a cycloalkenyl group, as defined herein, appended to the parent molecular moiety through an alkylene group, as defined herein.

The term "cycloalkyl" as used herein, means a monocyclic, or a bicyclic cycloalkyl, or a spirocyclic cycloalkyl. The monocyclic cycloalkyl is a carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Representative examples of bicyclic cycloalkyls include, but are not limited to, bicyclo[4.1.0]heptane, bicyclo[6.1.0]nonane, octahydroindene, and decahydronaphthalene. The monocyclic and the bicyclic cycloalkyl groups of the present invention may contain one or two alkylene bridges of 1, 2, 3, or 4 carbon atoms, wherein each bridge links two non-adjacent atoms within the groups. Examples of such bridged cycloalkyls include, but are not limited to, bicyclo[2.2.1]heptane, bicyclo[3.1.1]heptane, bicyclo[2.2.2]octane, bicyclo[3.3.1]nonane, adamantane (tricyclo[3.3.1.1$^{3,7}$]decane), and noradamantane (octahydro-2,5-methanopentalene). Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The monocyclic, bicyclic, and spirocyclic cycloalkyl groups of the present invention can be appended to the parent molecular moiety through any substitutable carbon atom of the groups.

The term "cycloalkylalkyl," as used herein, means a cycloalkyl group appended to the parent molecular moiety through an alkylene group, as defined herein. Representative example of cycloalkylalkyl includes, but not limited to, bicyclo[2.2.1]heptylmethyl (including bicyclo[2.2.1]hept-2-ylmethyl).

The term "formyl" as used herein, means a —C(O)H group.

The term "formylalkyl" as used herein, means a formyl group, as defined herein, appended to the parent molecular moiety through an alkylene group, as defined herein. Representative examples of formylalkyl include, but are not limited to, formylmethyl and 2-formylethyl.

The term "halo" or "halogen" as used herein, means F, Cl, Br, or I.

The term "haloalkoxy" as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkyl" as used herein, means a haloalkoxy group, as defined herein, appended to the parent molecular moiety through an alkylene group, as defined herein.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2,2-difluoroethyl, trifluoromethyl, 4-fluorobutyl, 2,2,2-trifluoroethyl, 2,2,2-trifluoro-1,1-dimethylethyl, difluoromethyl, 3,3,3-trifluoropropyl, 2,2,2-trichloro-1,1-dimethylethyl, pentafluoroethyl, 2-chloro-3-fluoropentyl, and 2-iodoethyl.

The term "heteroaryl," as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, benzoxadiazolyl, 1,3-benzothiazolyl, benzimidazolyl, benzodioxolyl, benzothienyl, chromenyl, cinnolinyl, furopyridinyl, indolyl, indazolyl, isoindolyl, isoquinolinyl, naphthyridinyl, oxazolopyridinyl, quinolinyl, and thienopyridinyl. The monocyclic and the bicyclic heteroaryl groups are connected to the parent molecular moiety through any substitutable carbon atom or any substitutable nitrogen atom contained within the groups.

The term "heteroarylalkyl," as used herein, means a heteroaryl group appended to the parent molecular moiety through an alkylene group, as defined herein.

The term "heteroarylcarbonyl" as used herein, refers to an heteroaryl group, as defined herein, appended to the parent molecular moiety through a carbonyl group.

The term "heteroarylcarbonyloxy" as used herein, refers to an heteroarylcarbonyl group, as defined herein, appended to the parent molecular moiety through an oxygen atom.

The term "heteroaryloxy" as used herein, refers to an heteroaryl group, as defined herein, appended to the parent molecular moiety through an oxygen atom.

The term "heterocycle" or "heterocyclic" as used herein, means a monocyclic, bicyclic, or a spirocyclic ring system containing at least one heteroatom. The monocyclic heterocycle is a 3-, 4- 5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S. Representative examples of monocyclic heterocycles include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, dihydropyranyl (including 3,4-dihydropyran-6-yl, 2,3-dihydropyranyl), 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl (including tetrahydropyran-4-yl, tetrahydropyran-2-yl, tetrahydropyran-3-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle of the present invention is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Representative examples of bicyclic heterocycle include, but are not limited to, 1,3-benzodioxolyl (including 1,3-benzodioxol-4-yl and 1,3-benzodioxol-5-yl), 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 4-, 5-, or 6-membered monocyclic cycloalkyl. One example of a spiroheterocycle is 5-oxaspiro[3,4]octane. The heterocycle groups are connected to the parent molecular moiety through any substitutable carbon atom or any substitutable nitrogen atom contained within the group. The monocyclic or bicyclic heterocycle groups of the present invention may contain an alkenylene bridge of 2, 3, or 4 carbon atoms, or one or two alkylene bridges of 1, 2, 3, or 4 carbon atoms, wherein each bridge links two non-adjacent carbon atoms within the groups. Examples of such bridged heterocycles include, but are not limited to, bicyclo[2.2.1]heptyl, bicyclo[3.3.1]heptyl, bicyclo[2.2.2]octyl, bicyclo[3.3.1]nonyl, oxaadamantane (2-oxatricyclo[3.3.1.1$^{3,7}$]decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane.

The term "heterocyclealkyl," as used herein, means a heterocycle group appended to the parent molecular moiety through an alkylene group, as defined herein. Representative examples of heterocyclealkyl include, but are not limited to, tetrahydrofuran-2-ylmethyl, oxetan-3-ylmethyl, 3-methyloxetan-3-ylmethyl, 1,3-dioxolan-2-ylmethyl, 3-methyl-4,5-dihydroisoxazol-5-ylmethyl, 2,2-dimethyl-1,3-dioxolan-4-ylmethyl, 5-oxotetrahydrofuran-2-ylmethyl, (5-methyltetrahydrofuran-2-yl)methyl, tetrahydro-2H-pyran-4-ylmethyl, tetrahydro-2H-pyran-2-ylmethyl, tetrahydro-2H-pyran-3-ylmethyl, and 1,4-dioxan-2-ylmethyl.

The term "heterocycleoxy" as used herein, refers to a heterocycle group, as defined herein, appended to the parent molecular moiety through an oxygen atom.

The aryl, cycloalkyl, cycloalkenyl, heteroaryl, and the heterocycle moieties of this invention are optionally substituted with 1, 2, 3, 4, 5, or 6 substituents independently selected from the group as described herein below, unless otherwise noted. The optional substituents are independently selected from the group consisting of alkenyl, alkoxy, alkoxyalkoxy, alkoxyalkoxyalkyl, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfinyl, alkylsulfinylalkyl, alkyl-S(O)$_2$—, alkyl-S(O)$_2$-alkyl-, alkyl-S—, alkyl-5-alkyl-, alkynyl, carboxy, carboxyalkyl, cyano, cyanoalkyl, formyl, formylalkyl, halogen, haloalkyl, haloalkoxy, hydroxy, hydroxyalkyl, oxo, —SH, nitro, NZ$_1$Z$_2$-alkylene-O—, —NZ$_1$Z$_2$, and (NZ$_3$Z$_4$)carbonyl.

The term "hydroxy" or "hydroxyl" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, 1-hydroxy-1-methylethyl, 1-ethyl-1-hydroxypropyl, 1-hydroxy-1-methylpropyl, and 2-ethyl-4-hydroxyheptyl.

The term "hydroxyhaloalkyl" as used herein, means at least one hydroxy group, as defined herein, is appended to the parent molecular moiety through a haloalkyl group, as defined herein. Representative examples of hydroxyhaloalkyl include, but are not limited to, 2-fluoro-1-(fluoromethyl)-1-hydroxyethyl, 2,2,2-trifluoro-1-hydroxy-1-methylethyl, 2-fluoro-1-hydroxy-1-methylethyl, and 2,2-difluoro-1-hydroxy-1-methylethyl.

The term "hydroxyalkynyl" as used herein, means at least one hydroxy group, as defined herein, is appended to the parent molecular moiety through an alkynyl group, as defined herein. Representative example of hydroxyalkynyl includes, but is not limited to, 3-hydroxy-3-methylbut-1-ynyl.

The term "hydroxy-protecting group" or "O-protecting group" means a substituent that protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "mercapto" as used herein, means a —SH group.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl(trityl).

The term "nitro" as used herein, means a —NO$_2$ group.

The term "nitroalkyl" as used herein, means an nitro group, as defined herein, appended to the parent molecular moiety through an alkylene group, as defined herein.

The term "NZ$_1$Z$_2$" as used herein, means two groups, Z$_1$ and Z$_2$, which are appended to the parent molecular moiety through a nitrogen atom. Z$_1$ and Z$_2$ are each independently hydrogen, alkyl, alkylcarbonyl, aryl, arylalkyl, haloalkyl, and formyl. In certain instances within the present invention, Z$_1$ and Z$_2$ taken together with the nitrogen atom to which they are attached form a heterocyclic ring. Representative examples of NZ$_1$Z$_2$ include, but are not limited to, amino, methylamino, acetylamino, acetylmethylamino, phenylamino, benzylamino, azetidinyl, pyrrolidinyl and piperidinyl.

The term "NZ$_3$Z$_4$" as used herein, means two groups, Z$_3$ and Z$_4$, which are appended to the parent molecular moiety through a nitrogen atom. Z$_3$ and Z$_4$ are each independently hydrogen, alkyl, haloalkyl, aryl, and arylalkyl. Representative examples of NZ$_3$Z$_4$ include, but are not limited to, amino, methylamino, phenylamino and benzylamino.

The term "(NZ$_3$Z$_4$)carbonyl" as used herein, means a NZ$_3$Z$_4$ group, as defined herein, appended to the parent molecular moiety through a carbonyl group, as defined herein. Representative examples of (NZ$_3$Z$_4$)carbonyl include, but are not limited to, aminocarbonyl, (methylamino)carbonyl, (dimethylamino)carbonyl, and (ethylmethylamino)carbonyl.

The term "oxo" as used herein, means a =O moiety.

The term "sulfinyl" as used herein, means a —S(O)— group.

The term "sulfonyl" as used herein, means a —SO$_2$— group.

b. COMPOUNDS

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

In compounds of formula (I), $R_1$ is as described in the Summary section. One embodiment of the invention relates to compounds of formula (I) wherein $R_1$ is $C_3$-$C_7$ alkyl. Examples of $R_1$ as $C_3$-$C_7$ alkyl include, but are not limited to, isobutyl and n-butyl.

Other compounds of the invention include, but not limited to, those wherein $R_1$ is alkoxy-($C_2$-$C_6$ alkylene)- such as 2-methoxyethyl.

Yet other compounds of the invention include, but not limited to, those wherein
$R_1$ is alkylcarbonylalkyl, for example, 3,3-dimethyl-2-oxobutyl.

Yet other compounds of the invention include, but are not limited to, those wherein $R_1$ is arylcarbonyloxy-($C_2$-$C_6$ alkylene)- wherein the aryl moiety is optionally substituted as described in the Detailed Description section. For example, $R_1$ is phenylcarbonyloxyethyl wherein the phenyl moiety is optionally substituted, for example, the phenyl moiety is optionally substituted with substituents selected from alkyl, alkoxy, cyano, halogen, —NZ$_1$Z$_2$, haloalkyl, and haloalkoxy.

Further examples of compounds of the invention include, but are not limited to, those wherein $R_1$ is haloalkyl (for example, 4-fluorobutyl).

Yet further examples of compounds of the invention include, but are not limited to, those wherein $R_1$ is cycloalkylalkyl wherein the cycloalkyl moiety is optionally substituted as described in the Detailed Description. For example, $R_1$ includes, but is not limited to, cyclopropylmethyl and cyclobutylmethyl, wherein the cyclopropyl and the cyclobutyl moieties are optionally substituted.

Yet another embodiment of the invention provides compounds of formula (I) wherein $R_1$ is heterocyclealkyl wherein the heterocycle moiety is optionally substituted as described in the Detailed Description section. Examples of the heterocycle moiety of the heterocyclealkyl include, but are not limited to, morpholinyl, tetrahydrofuranyl, piperidinyl, aziridinyl, pyranyl, 1,3-dioxolanyl, and pyrrolidinyl, each of which is optionally substituted as described in the Detailed Description section. The alkyl moieties of the heterocyclealkyl include, but are not limited to, methyl and ethyl. Examples of the optional substituents of the heterocycle moiety of the heterocyclealkyl include, but are not limited to, alkyl, alkoxy, oxo, halogen, haloalkyl, haloalkoxy, hydroxy, and —NZ$_1$Z$_2$ wherein Z$_1$, Z$_2$ are, for example, independently hydrogen, alkyl, or haloalkyl. For example, $R_1$ includes, but is not limited to, morpholinylethyl (including 2-morpholin-4-ylethyl), piperidinylmethyl, piperidinylethyl (including 2-piperidin-1-ylethyl), pyrrolidinylmethyl (including pyrrolidin-2-ylmethyl), pyranylmethyl, 1,3-dioxolanylmethyl and tetrahydrofuranylmethyl (including tetrahydrofuran-2-ylmethyl and tetrahydrofuran-3-ylmethyl) wherein each of the morpholinyl, piperidinyl, pyrrolidinyl, pyranyl, 1,3-dioxolanyl, and tetrahydrofuranyl are optionally substituted as described hereinabove.

One embodiment of the invention pertains to compounds of formula (I) wherein A is N. Such compounds are represented by formula (Ia)

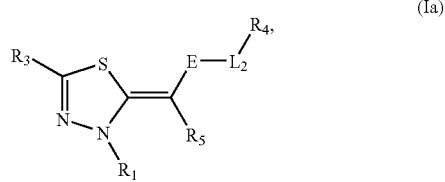

wherein $R_1$, $R_3$, $R_4$, $R_5$, E, and $L_2$ are as defined in the Summary and Detailed Description sections.

Yet another embodiment of the invention pertains to compounds of formula (I) wherein A is C($R_2$), as represented by formula (Ib)

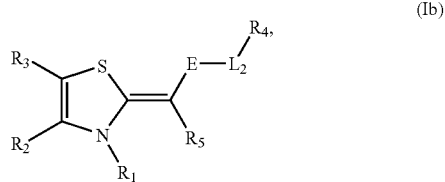

wherein $R_1$, $R_2$, $R_3$, $R_4$, $R_5$, E, and $L_2$ are as defined in the Summary and Detailed Description sections.

$R_2$ and $R_3$ are as disclosed in the Summary.

One embodiment of the invention describes compounds of formula (I) wherein A is C($R_2$), and $R_2$ and $R_3$ are independently hydrogen, alkenyl (for example, isopropenyl), alkoxycarbonyl (for example, ethoxycarbonyl), alkylcarbonyl (for example, methylcarbonyl), alkyl (for example, methyl, tert-butyl), aryl (for example, phenyl), cycloalkyl (for example, cyclopropyl), formyl, halogen (for example, Br), haloalkyl (for example, trifluoromethyl), heterocycle (for example, 1,3-dioxolanyl, including 1,3-dioxolan-2-yl), hydroxyalkyl (for example, 1-hydroxy-1-methylethyl, 1-hydroxy-1-methylpropyl, 1-ethyl-1-hydroxypropyl), hydroxyalkynyl (for example, 3-hydroxy-3-methylbut-1-ynyl), hydroxyhaloalkyl (for example, 2-fluoro-1-(fluoromethyl)-1-hydroxyethyl, 2,2-difluoro-1-hydroxy-1-methylethyl, 2-fluoro-1-hydroxy-1-methylethyl, 2,2,2-trifluoro-1-hydroxy-1-methylethyl), $R_jR_kN$— wherein $R_j$ and $R_k$ are as described in the Summary (for example, $R_j$ is hydrogen, $R_k$ is alkoxycarbonyl such as tert-butoxycarbonyl), $R_jR_kN$-alkylene- wherein $R_j$ and $R_k$ are as described in the Summary (for example, $R_jR_kN$-alkylene- is 1-amino-1-ethylpropyl, 1-amino-1-methylethyl), $R_mR_nN$—C(O)— wherein $R_m$ and $R_n$ are as described in the Summary (for example, $R_m$ and $R_n$ are independently hydrogen or alkyl), or $R_pO$—N=C($R^z$)— wherein $R_p$ and $R_z$ are as described in the Summary (for example, $R_p$ and $R_z$ are independently hydrogen or alkyl), wherein the aryl moiety, the cycloalkyl moiety, and the heterocycle moiety are optionally substituted as described in the Detailed Description. For example, the aryl and the cycloalkyl are optionally substituted with 1 or 2 substituents selected from the group consisting of alkyl (for example, methyl), halogen, and haloalkyl (for example, trifluoromethyl). For example, the heterocycle moiety is optionally substituted with 1 or 2 substituents selected from the group consisting of oxo, alkyl (for example, methyl), halogen, and haloalkyl (for example, trifluoromethyl).

Another embodiment of the invention include compounds of formula (I) wherein A is C($R_2$), and $R_2$ and $R_3$ together with the carbon atoms to which they are attached from a ring as described in the Summary, and $R_1$, $R_4$, $R_5$, E, $L_2$ have values as described in the Summary and the Detailed Description.

Thus, one embodiment of the invention includes those having formula (Ic)

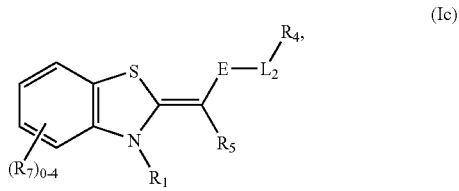

(Ic)

wherein $R_7$ represents optional substituents, selected from alkyl, halogen, and haloalkyl, and E, $R_1$, $R_4$, $R_5$, and $L_2$ are as disclosed in the Summary and the Detailed Description sections.

Another embodiment of the invention includes those having formula (Id)

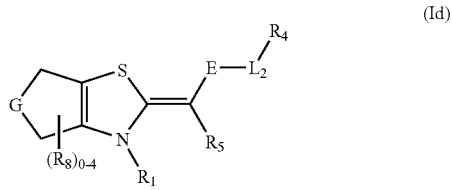

(Id)

wherein G is N(H), N(alkyl), O, $CH_2$, or $CH_2CH_2$, $R_8$ represents optional substituents selected from the group consisting of alkyl, halogen, and haloalkyl, two $R_8$ groups on the same carbon atom together with the carbon atom to which they are attached, optionally form a =O group, and E, $R_1$, $R_4$, $R_5$, and $L_2$ are as disclosed in the Summary and the Detailed Description sections.

$R_5$ is as described in the Summary section.

One embodiment of the invention is directed to compounds of formula (I) wherein $R_5$ is hydrogen.

Other embodiment includes, but not limited to, compounds of formula (I) wherein $R_5$ is halogen (for example, F).

Compounds of formula (I) include, but are not limited to, those wherein E is C(O).

Other compounds of the invention include, but are not limited to, those of formula (I) wherein E is C(S).

$L_2$ is a bond, O or N($R_e$) wherein $R_e$ is as described in the Summary section. For example, $R_e$ is hydrogen or alkyl. In one embodiment, $R_e$ is hydrogen.

$R_4$ is as described in the Summary section. One embodiment of the invention includes, but not limited to, those of formula (I) wherein $R_4$ is substituted phenyl or optionally substituted naphthyl, the substituents of phenyl and the optional substituents of naphthyl are represented by $R_6$, and $R_6$ is as described in the Summary section. $R_6$, for example, includes alkyl (for example, methyl, tert-butyl), cyano, halogen, haloalkyl (for example, trifluoromethyl), —$OR_{eu}$ wherein $R_{eu}$ is as disclosed in the Summary (for example, $R_{eu}$ is alkyl such as methyl, ethyl, or haloalkyl such as trifluoromethyl), —N($R_{wu}$)($R_{gu}$) wherein $R_{wu}$ and $R_{gu}$ are as disclosed in the Summary section (for example, $R_{wu}$ and $R_{gu}$ are independently hydrogen or alkyl such as methyl), —N($R_{wu}$)C(O)O$R_{eu}$ wherein $R_{wu}$ and $R_{eu}$ are as disclosed in the Summary section (for example, $R_{eu}$ is alkyl such as methyl, ethyl, and $R_{wu}$ is hydrogen or alkyl such as methyl), or —C(O)O$R_{eu}$ wherein $R_{eu}$ is as disclosed in the Summary section (for example, $R_{eu}$ is alkyl such as methyl, ethyl). In one embodiment, $R_4$ is phenyl, substituted with one or two $R_6$ groups wherein $R_6$ is as disclosed in the Summary and the Detailed Description.

In yet another embodiment, $R_4$ includes, but not limited to, $C_4$-$C_{10}$ alkyl such as 2,2-dimethylpropyl or haloalkyl (for example, 2,2,2-trichloro-1,1-dimethylethyl).

Another embodiment of the invention includes, but not limited to, those wherein $R_4$ is cycloalkyl, optionally substituted as described in the Summary. For example, $R_4$ is adamantyl, bicyclo[2.2.1]heptyl, cyclopropyl, cyclopentyl, or cyclohexyl, each of which is optionally substituted as described in the Summary. Examples of the optional substituents include, but are not limited to, alkyl such as methyl, unsubstituted phenyl, and oxo.

Yet another embodiment of the invention includes, but not limited to, those wherein $R_4$ is cycloalkylalkyl, and the cycloalkyl moiety of cycloalkylalkyl is optionally substituted as described in the Summary. For example, $R_4$ is cyclopentylmethyl or bicyclo[2.2.1]heptylmethyl, and the cyclopentyl and the bicyclo[2.2.1]heptyl are optionally substituted as described in the Summary. Examples of the optional substituents include, but are not limited to, alkyl such as methyl, and oxo.

A further embodiment of the invention includes, but not limited to, those wherein $R_4$ is arylalkyl such as benzyl.

Yet a further embodiment of the invention includes, but not limited to, those wherein $R_4$ is heterocycle, optionally substituted as described in the Summary. For example, the optionally substituted heterocycle includes, but not limited to, morpholinyl, 1,3-benzodioxolyl, tetrahydropyranyl, and 2,3-dihydropyranyl, wherein the optional substituents are as described in the Summary.

Yet another embodiment of the invention includes, but not limited to, those wherein $R_4$ is heteroaryl, optionally substituted as described in the Summary. For example, $R_4$ is pyridinyl, quinolinyl, thienyl, 1,3-thiazolyl, benzofuranyl, and benzothienyl, each of which is optionally substituted as described in the Summary. Examples of the optional substituents include, but are not limited to, alkyl (for example, methyl, tert-butyl), cyano, halogen, haloalkyl (for example, trifluoromethyl), —$OR_{eu}$ wherein $R_{eu}$ is as disclosed in the Summary (for example, $R_{eu}$ is alkyl such as methyl, ethyl, or haloalkyl such as trifluoromethyl), —N($R_{wu}$)($R_{gu}$) wherein $R_{wu}$ and $R_{gu}$ are as disclosed in the Summary section (for example, $R_{wu}$ and $R_{gu}$ are independently hydrogen or alkyl such as methyl), —N($R_{wu}$)C(O)O$R_{eu}$ wherein $R_{wu}$ and $R_{eu}$ are as disclosed in the Summary section (for example, $R_{eu}$ is alkyl such as methyl, ethyl, and $R_{wu}$ is hydrogen or alkyl such as methyl), or —C(O)O$R_{eu}$ wherein $R_{eu}$ is as disclosed in the Summary section (for example, $R_{eu}$ is alkyl such as methyl, ethyl).

It is appreciated that the present invention contemplates compounds of formula (I) with combinations of the above embodiments, including particular, more particular and preferred embodiments.

Accordingly, one aspect of the invention is directed to compounds of formula (Ia) wherein E is C(O), and $L_2$ is a bond.

Another aspect of the invention is directed to compounds of formula (Ia) wherein E is C(O), and $L_2$ is N($R_e$) and $R_e$ is as disclosed in the Summary and the Detailed Description sections. For example, $R_e$ is hydrogen or alkyl. In one embodiment, $R_e$ is hydrogen.

Another aspect of the invention is directed to compounds of formula (Ia) wherein E is C(O), and $L_2$ is O.

Yet another aspect of the invention is directed to compounds of formula (Ia) wherein E is C(S) and $L_2$ is a bond.

Another aspect of the invention is directed to compounds of formula (Ia) wherein E is C(S), $L_2$ is N($R_e$), and $R_e$ is as disclosed in the Summary and the Detailed Description sections. For example, $R_e$ is hydrogen or alkyl. In one embodiment, $R_e$ is hydrogen.

Another aspect of the invention is directed to compounds of formula (Ia) wherein E is C(S) and $L_2$ is O.

A further aspect of the invention is directed to compounds of formula (Ib) wherein E is C(O) and $L_2$ is a bond.

Yet a further aspect of the invention is directed to compounds of formula (Ib) wherein E is C(O), $L_2$ is N($R_e$), and $R_e$ is as disclosed in the Summary and the Detailed Description sections. For example, $R_e$ is hydrogen or alkyl. In one embodiment, $R_e$ is hydrogen.

Another aspect of the invention is directed to compounds of formula (Ib) wherein E is C(O) and $L_2$ is O.

Yet another aspect of the invention is directed to compounds of formula (Ib) wherein E is C(S) and $L_2$ is a bond.

Another aspect of the invention is directed to compounds of formula (Ib) wherein E is C(S), $L_2$ is N($R_e$), and $R_e$ is as disclosed in the Summary and the Detailed Description sections. For example, $R_e$ is hydrogen or alkyl. In one embodiment, $R_e$ is hydrogen.

Another aspect of the invention is directed to compounds of formula (Ib) wherein E is C(S) and $L_2$ is O.

Within each of the foregoing compounds of formula (Ia) and (Ib), $R_1$, $R_2$, $R_3$, $R_4$ and $R_5$ have meanings as described in the Summary and Detailed Description sections.

For example, within each of the foregoing compounds, examples of a group of compounds of formula (Ia) or (Ib) include those wherein $R_1$ is $C_3$-$C_7$ alkyl, alkoxy-($C_2$-$C_6$ alkylene)-, alkylcarbonylalkyl, arylcarbonyloxy-($C_2$-$C_6$ alkylene)-, haloalkyl, cycloalkylalkyl, or heterocyclealkyl.

Thus, one embodiment of the invention provides a group of foregoing compounds of formula (Ia) or (Ib) wherein $R_1$ is $C_3$-$C_7$ alkyl. Examples of $R_1$ as $C_3$-$C_7$ alkyl include, but are not limited to, isobutyl and n-butyl.

Examples of another group of compounds having formula (Ia) or (Ib) include, but not limited to, those wherein $R_1$ is alkoxy-($C_2$-$C_6$ alkylene)- such as 2-methoxyethyl.

Examples of yet another group of compounds having formula (Ia) or (Ib) include, but not limited to, those wherein $R_1$ is alkylcarbonylalkyl, for example, 3,3-dimethyl-2-oxobutyl.

Further examples of another group of compounds having formula (Ia) or (Ib) include, but are not limited to, those wherein $R_1$ is arylcarbonyloxy-($C_2$-$C_6$ alkylene)- wherein the aryl moiety is optionally substituted as described in the Detailed Description section. For example, $R_1$ is phenylcarbonyloxyethyl wherein the phenyl moiety is optionally substituted, for example, the phenyl moiety is optionally substituted with substituents selected from alkyl, alkoxy, cyano, halogen, —$NZ_1Z_2$, haloalkyl, and haloalkoxy.

Further examples of yet another group of compounds having formula (Ia) or (Ib) include, but are not limited to, those wherein $R_1$ is haloalkyl (for example, 4-fluorobutyl).

Yet other examples of a group of compounds having formula (Ia) or (Ib) include, but are not limited to, those wherein $R_1$ is cycloalkylalkyl wherein the cycloalkyl moiety is optionally substituted as described in the Detailed Description. For example, $R_1$ includes, but is not limited to, cyclopropylmethyl and cyclobutylmethyl, wherein the cyclopropyl and the cyclobutyl moieties are optionally substituted.

Yet other examples of another group of compounds of formula (Ia) or (Ib) include, but are not limited to, those wherein $R_1$ is heterocyclealkyl wherein the heterocycle moiety is optionally substituted as described in the Detailed Description section. Examples of the heterocycle moiety of the heterocyclealkyl include, but are not limited to, morpholinyl, tetrahydrofuranyl, piperidinyl, aziridinyl, pyranyl, 1,3-dioxolanyl, and pyrrolidinyl, each of which is optionally substituted as described in the Definition. The alkyl moieties of the heterocyclealkyl include, but are not limited to, methyl and ethyl. Examples of the optional substituents of the heterocycle moiety of the heterocyclealkyl include, but are not limited to, alkyl, alkoxy, oxo, halogen, haloalkyl, haloalkoxy, hydroxy, and —$NZ_1Z_2$ wherein $Z_1$, $Z_2$ are, for example, independently hydrogen, alkyl, or haloalkyl. For example, $R_1$ includes, but is not limited to, morpholinylethyl (including 2-morpholin-4-ylethyl), piperidinylmethyl, piperidinylethyl (including 2-piperidin-1-ylethyl), pyrrolidinylmethyl (including pyrrolidin-2-ylmethyl), pyranylmethyl, 1,3-dioxolanylmethyl, and tetrahydrofuranylmethyl (including tetrahydrofuran-2-ylmethyl and tetrahydrofuran-3-ylmethyl) wherein each of the morpholinyl, piperidinyl, pyrrolidinyl, pyranyl, 1,3-dioxolanyl, and tetrahydrofuranyl are optionally substituted as described hereinabove.

Within each group of compounds of formula (Ia) or (Ib) as described in the preceding paragraphs, $R_2$, $R_3$, $R_4$, and $R_5$, have values as defined in the Summary and the Detailed Description. $R_5$, for example, is hydrogen or halogen (for example, fluorine).

Thus, of each groups of compounds of formula (Ia) or (Ib) as described in the preceding paragraphs, examples of a subgroup include, but are not limited to, those wherein $R_5$ is hydrogen.

Examples of another subgroup of compounds of formula (Ia) or (Ib) include those wherein $R_5$ is halogen. In one embodiment, $R_5$ is fluorine.

Of all examples of the groups and subgroups of compounds of formula (Ia) or (Ib) as discussed herein-above, $R_2$, $R_3$, and $R_4$ have values as defined in the Summary and the DETAILED DESCRIPTION For example, for each of the foregoing groups and subgroups of compounds of formula (Ia) or (Ib), an example of $R_4$ is substituted phenyl or optionally substituted naphthyl, the substituents of phenyl and the optional substituents of naphthyl are represented by $R_6$, and $R_6$ is as described in the Summary section. $R_6$, for example, includes alkyl (for example, methyl, tert-butyl), cyano, halogen, haloalkyl (for example, trifluoromethyl), —$OR_{eu}$ wherein $R_{eu}$ is as disclosed in the Summary (for example, $R_{eu}$ is alkyl such as methyl, ethyl, or haloalkyl such as trifluoromethyl), —N($R_{wu}$)($R_{gu}$) wherein $R_{wu}$ and $R_{gu}$ are as disclosed in the Summary section (for example, $R_{wu}$ and $R_{gu}$ are independently hydrogen or alkyl such as methyl), —N($R_{wu}$)C(O)O$R_{eu}$ wherein $R_{wu}$ and $R_{eu}$ are as disclosed in the Summary section (for example, $R_{eu}$ is alkyl such as methyl, ethyl, and $R_{wu}$ is hydrogen or alkyl such as methyl), or —C(O)O$R_{eu}$ wherein $R_{eu}$ is as disclosed in the Summary section (for example, $R_{eu}$ is alkyl such as methyl, ethyl). In one embodiment, $R_4$ is phenyl, substituted with one or two $R_6$ groups wherein $R_6$ is as disclosed in the Summary and the Detailed Description sections.

Another example of $R_4$ for the foregoing groups and subgroups of compounds includes, but are not limited to, $C_4$-$C_{10}$ alkyl such as 2,2-dimethylpropyl or haloalkyl (for example, 2,2,2-trichloro-1,1-dimethylethyl).

Yet other example of $R_4$ for the foregoing groups and subgroups of compounds includes, but not limited to, cycloalkyl, optionally substituted as described in the Summary. For example, $R_4$ is adamantyl, bicyclo[2.2.1]heptyl, cyclopropyl, cyclopentyl, or cyclohexyl, each of which is optionally substituted as described in the Summary. Examples of the optional substituents include, but are not limited to, alkyl such as methyl, unsubstituted phenyl, and oxo.

Yet another example of $R_4$ for the foregoing groups and subgroups of compounds includes, but not limited to, cycloalkylalkyl, wherein the cycloalkyl moiety of cycloalkylalkyl is optionally substituted as described in the Summary. For example, $R_4$ is cyclopentylmethyl or bicyclo[2.2.1]heptylmethyl, wherein the cyclopentyl and the bicyclo[2.2.1]heptyl are each optionally substituted as described in the Summary. Examples of the optional substituents include, but are not limited to, alkyl such as methyl, and oxo.

Yet another example of $R_4$ for the foregoing groups and subgroups of compounds includes, but not limited to, arylalkyl (for example, benzyl).

Yet a further example of $R_4$ for the foregoing groups and subgroups of compounds includes, but not limited to, heterocycle, optionally substituted as described in the Summary. For example, the heterocycle includes, but not limited to, morpholinyl, 1,3-benzodioxolyl, tetrahydropyranyl, and 2,3-dihydropyranyl, each of which is optionally substituted as described in the Summary.

Yet a further example of $R_4$ for the foregoing groups and subgroups of compounds includes, but not limited to, heteroaryl, optionally substituted as described in the Summary. Examples of $R_4$ as heteroaryl include, but are not limited to, pyridinyl, quinolinyl, thienyl, 1,3-thiazolyl, benzofuranyl, and benzothienyl, each of which is optionally substituted as described in the Summary. Examples of the optional substituents include, but are not limited to, alkyl (for example, methyl, tert-butyl), cyano, halogen, haloalkyl (for example, trifluoromethyl), —$OR_{eu}$ wherein $R_{eu}$ is as disclosed in the Summary (for example, $R_{eu}$ is alkyl such as methyl, ethyl, or haloalkyl such as trifluoromethyl), —$N(R_{wu})(R_{gu})$ wherein $R^{wu}$ and $R_{gu}$ are as disclosed in the Summary section (for example, $R_u$ and $R_{gu}$ are independently hydrogen or alkyl such as methyl), —$N(R_{wu})C(O)OR_{eu}$ wherein $R_u$ and $R_{eu}$ are as disclosed in the Summary section (for example, $R_{eu}$ is alkyl such as methyl, ethyl, and $R_u$ is hydrogen or alkyl such as methyl), or —$C(O)OR_{eu}$ wherein $R_{eu}$ is as disclosed in the Summary section (for example, $R_{eu}$ is alkyl such as methyl, ethyl).

For each of the foregoing groups and subgroups of compounds of formula (Ia) or (Ib), examples of $R_3$ include, but are not limited to, hydrogen, alkenyl (for example, isopropenyl), alkoxycarbonyl (for example, ethoxycarbonyl), alkylcarbonyl (for example, methylcarbonyl), alkyl (for example, methyl, tert-butyl), aryl (for example, phenyl), cycloalkyl (for example, cyclopropyl), formyl, halogen (for example, Br), haloalkyl (for example, trifluoromethyl), heterocycle (for example, 1,3-dioxolanyl, including 1,3-dioxolan-2-yl), hydroxyalkyl (for example, 1-hydroxy-1-methylethyl, 1-hydroxy-1-methylpropyl, 1-ethyl-1-hydroxypropyl), hydroxyalkynyl (for example, 3-hydroxy-3-methylbut-1-ynyl), hydroxyhaloalkyl (for example, 2-fluoro-1-(fluoromethyl)-1-hydroxyethyl, 2,2-difluoro-1-hydroxy-1-methylethyl, 2-fluoro-1-hydroxy-1-methylethyl, 2,2,2-trifluoro-1-hydroxy-1-methylethyl), $R_jR_kN$— wherein $R_j$ and $R_k$ are as described in the Summary (for example, $R_j$ is hydrogen, $R_k$ is alkoxycarbonyl such as tert-butoxycarbonyl), $R_jR_kN$-alkylene- wherein $R_j$ and $R_k$ are as described in the Summary (for example, $R_jR_kN$-alkylene- is 1-amino-1-ethylpropyl, 1-amino-1-methylethyl), $R_mR_nN$—$C(O)$— wherein $R_m$ and $R_n$ are as described in the Summary (for example, $R_m$ and $R_n$ are independently hydrogen or alkyl), and $R_pO$—N=C($R_z$)— wherein $R_p$ and $R_z$ are as described in the Summary (for example, $R_p$ and $R_z$ are independently hydrogen or alkyl), wherein the aryl moiety, the cycloalkyl moiety, and the heterocycle moiety are optionally substituted as described in the Summary. For example, the aryl and the cycloalkyl are optionally substituted with 1 or 2 substituents selected from the group consisting of alkyl (for example, methyl), halogen, and haloalkyl (for example, trifluoromethyl). For example, the heterocycle moiety is optionally substituted with 1 or 2 substituents selected from the group consisting of oxo, alkyl (for example, methyl), halogen, and haloalkyl (for example, trifluoromethyl).

For each of the foregoing groups and subgroups of compounds of formula (Ib), $R_2$ has values as described in the Summary and Detailed Description (for example, $R_2$ has the values as described for $R_3$ in the preceding paragraph), with the proviso that when E is C(O), $L_2$ is a bond, $R_4$ is aryl, $R_1$ is $C_3$-$C_5$ alkyl, $C_2$-$C_5$ alkenyl, $C_2$-$C_5$ alkynyl, or 4-amino-2-methyl-5-pyrimidinyl)methyl, $R_3$ is hydrogen or phenyl, then $R_2$ is not hydrogen or $C_1$-$C_5$ alkyl.

Other examples of compounds of formula (Ib) include those groups and subgroups as described herein above wherein $R_2$ and $R_3$ together with the carbon atoms to which they are attached from a ring as described in the Summary.

Thus, one embodiment of the invention includes those groups and subgroups of compounds as described hereinabove, having formula (Ic)

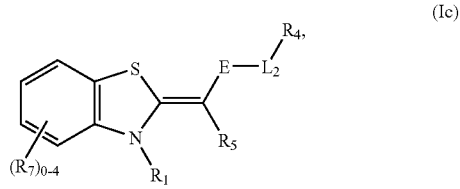

(Ic)

wherein $R_7$ represents optional substituents, independently selected the group consisting of from alkyl, halogen, and haloalkyl, and E, $R_1$, $R_4$, $R_5$, and $L_2$ are as in each of the foregoing groups and subgroups of compounds.

For example, one embodiment of the invention provides a group of compounds of formula (Ic) wherein E is C(O), $L_2$ is a bond, $R_5$ is hydrogen, and $R_1$ is $C_3$-$C_7$ alkyl (for example, n-butyl, isobutyl).

Other examples of a group of compounds of formula (Ic) include, but are not limited to, those wherein E is C(O), $L_2$ is a bond, $R_5$ is hydrogen, and $R_1$ is alkoxy-($C_2$-$C_6$ alkylene)- such as 2-methoxyethyl.

Further examples of a group of compounds having formula (Ic) include, but are not limited to, those wherein E is C(O), $L_2$ is a bond, $R_5$ is hydrogen, and $R_1$ is haloalkyl (for example, 4-fluorobutyl).

Yet other examples of a group of compounds of formula (Ic) include, but are not limited to, those wherein E is C(O), $L_2$ is a bond, $R_5$ is hydrogen, and $R_1$ is cycloalkylalkyl wherein the cycloalkyl moiety is optionally substituted as described in the Detailed Description. For example, $R_1$ includes, but is not limited to, cyclopropylmethyl and cyclobutylmethyl, wherein the cyclopropyl and the cyclobutyl moieties are optionally substituted as described in the Detailed Description.

Yet other examples of another group of compounds of formula (Ic) include, but are not limited to, those wherein E is C(O), $L_2$ is a bond, $R_5$ is hydrogen, and $R_1$ is heterocyclealkyl wherein the heterocycle moiety is optionally substituted as described in the Detailed Description section. Examples of the heterocycle moiety of the heterocyclealkyl include, but are not limited to, morpholinyl, tetrahydrofuranyl, piperidinyl, aziridinyl, pyranyl, 1,3-dioxolanyl, and pyrrolidinyl, each of which is optionally substituted as described in the Detailed Description section. The alkyl moieties of the heterocyclealkyl include, but are not limited to, methyl and ethyl. Examples of the optional substituents of the heterocycle moiety of the heterocyclealkyl include, but are not limited to, alkyl, alkoxy, oxo, halogen, haloalkyl, haloalkoxy, hydroxyl, and —$NZ_1Z_2$ wherein $Z_1$, $Z_2$ are, for example, independently hydrogen, alkyl, or haloalkyl. For example, $R_1$ includes, but is not limited to, morpholinylethyl (including 2-morpholin-4-ylethyl), piperidinylmethyl, piperidinylethyl (including 2-piperidin-1-ylethyl), pyrrolidinylmethyl (including pyrrolidin-2-ylmethyl), pyranylmethyl, 1,3-dioxolanylmethyl, and tetrahydrofuranylmethyl (including tetrahydrofuran-2-ylmethyl and tetrahydrofuran-3-ylmethyl) wherein each of the morpholinyl, piperidinyl, pyrrolidinyl, pyranyl, 1,3-dioxolanyl, and tetrahydrofuranyl are optionally substituted as described hereinabove.

Another embodiment of the invention includes those having formula (Id)

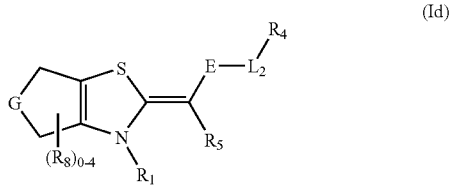

(Id)

wherein G is N(H), N(alkyl), O, $CH_2$, or $CH_2CH_2$, $R_8$ represents optional substituents independently selected from the group consisting of alkyl, halogen, and haloalkyl, two $R_8$ groups on the same carbon atom together with the carbon atom to which they are attached, optionally form a =O group, and E, $R_1$, $R_4$, $R_5$, and $L_2$ have values as disclosed in each of the foregoing groups and subgroups of compounds as described hereinabove.

For example, one embodiment of the invention provides a group of compounds of formula (Id) wherein E is C(O), $L_2$ is a bond, $R_5$ is hydrogen, and $R_1$ is $C_3$-$C_7$ alkyl (for example, n-butyl, isobutyl).

Other examples of a group of compounds of formula (Id) include, but are not limited to, those wherein E is C(O), $L_2$ is a bond, $R_5$ is hydrogen, and $R_1$ is alkoxy-($C_2$-$C_6$ alkylene)- such as 2-methoxyethyl.

Further examples of a group of compounds having formula (Id) include, but are not limited to, those wherein E is C(O), $L_2$ is a bond, $R_5$ is hydrogen, and $R_1$ is haloalkyl (for example, 4-fluorobutyl).

Yet other examples of a group of compounds of formula (Id) include, but are not limited to, those wherein E is C(O), $L_2$ is a bond, $R_5$ is hydrogen, and $R_1$ is cycloalkylalkyl wherein the cycloalkyl moiety is optionally substituted as described in the Detailed Description. For example, $R_1$ includes, but is not limited to, cyclopropylmethyl and cyclobutylmethyl, wherein the cyclopropyl and the cyclobutyl moieties are optionally substituted as described in the Detailed Description Yet other examples of another group of compounds of formula (Id) include, but are not limited to, those wherein E is C(O), $L_2$ is a bond, $R_5$ is hydrogen, and $R_1$ is heterocyclealkyl wherein the heterocycle moiety is optionally substituted as described in the Detailed Description section. Examples of the heterocycle moiety of the heterocyclealkyl include, but are not limited to, morpholinyl, tetrahydrofuranyl, piperidinyl, aziridinyl, pyranyl, 1,3-dioxolanyl, and pyrrolidinyl, each of which is optionally substituted as described in the Detailed Description. The alkyl moieties of the heterocyclealkyl include, but are not limited to, methyl and ethyl. Examples of the optional substituents of the heterocycle moiety of the heterocyclealkyl include, but are not limited to, alkyl, alkoxy, oxo, halogen, haloalkyl, haloalkoxy, hydroxyl, and —$NZ_1Z_2$ wherein $Z_1$, $Z_2$ are, for example, independently hydrogen, alkyl, or haloalkyl. For example, $R_1$ includes, but is not limited to, morpholinylethyl (including 2-morpholin-4-ylethyl), piperidinylmethyl, piperidinylethyl (including 2-piperidin-1-ylethyl), pyrrolidinylmethyl (including pyrrolidin-2-ylmethyl), pyranylmethyl, 1,3-dioxolanylmethyl, and tetrahydrofuranylmethyl (including tetrahydrofuran-2-ylmethyl and tetrahydrofuran-3-ylmethyl) wherein each of the morpholinyl, piperidinyl, pyrrolidinyl, pyranyl, 1,3-dioxolanyl, and tetrahydrofuranyl are optionally substituted as described hereinabove.

For each of the foregoing groups of compounds of formula (Ic) and (Id), $R_4$ has meanings as defined in the Summary.

For example, for each of the foregoing groups of compounds of formula (Ic) and (Id), examples of a subgroup include those wherein $R_4$ is substituted phenyl or optionally substituted naphthyl, wherein the substituents have values as described in the Summary and the Detailed Description.

Exemplary compounds of the invention having formula (I) include, but are not limited to:

(2Z)-2-(3-butyl-4,5-dimethyl-1,3-thiazol-2(3H)-ylidene)-1-(5-chloro-2-methoxyphenyl)ethanone;

(2Z)-1-(1-adamantyl)-2-(3-butyl-4,5-dimethyl-1,3-thiazol-2 (3H)-ylidene)ethanone;

tert-butyl (2Z)-(3-butyl-4,5-dimethyl-1,3-thiazol-2(3H)-ylidene)acetate;

(2Z)-1-(5-chloro-2-methoxyphenyl)-2-[3-(2-methoxyethyl)-4,5-dimethyl-1,3-thiazol-2(3H)-ylidene]ethanone;

(2Z)-2-(3-butyl-5-methyl-1,3-thiazol-2(3H)-ylidene)-1-(5-chloro-2-methoxyphenyl)ethanone;

(2Z)-2-(3-butyl-4,5-dimethyl-1,3-thiazol-2(3H)-ylidene)-1-cyclohexylethanone;

(2Z)-2-(3-butyl-4,5-dimethyl-1,3-thiazol-2(3H)-ylidene)-N-cyclohexylacetamide;

4-[(2Z)-2-(3-butyl-4,5-dimethyl-1,3-thiazol-2(3H)-ylidene) ethanoyl]morpholine;

(2Z)-2-(3-butyl-4,5-dimethyl-1,3-thiazol-2(3H)-ylidene)-N-(5-chloro-2-methoxyphenyl)acetamide;

(2Z)-1-(5-chloro-2-methoxyphenyl)-2-(3-propyl-1,3-benzothiazol-2(3H)-ylidene)ethanone;

(2Z)-2-(5-bromo-3-butyl-4-methyl-1,3-thiazol-2(3H)-ylidene)-1-(5-chloro-2-methoxyphenyl)ethanone;

(Z)-2-(5-acetyl-3-butyl-4-methylthiazol-2(3H)-ylidene)-1-(5-chloro-2-methoxyphenyl)ethanone;

(Z)-2-(3-butyl-5-(1-(hydroxyimino)ethyl)-4-methylthiazol-2(3H)-ylidene)-1-(5-chloro-2-methoxyphenyl)ethanone;

(2Z)-3-butyl-2-[2-(5-chloro-2-methoxyphenyl)-2-oxoethylidene]-2,3-dihydro-1,3-thiazole-5-carbaldehyde;
(2Z)-3-butyl-2-[2-(5-chloro-2-methoxyphenyl)-2-oxoethylidene]-2,3-dihydro-1,3-thiazole-5-carbaldehyde oxime;
(2Z)-1-(5-chloro-2-methoxyphenyl)-2-[4,5-dimethyl-3-(2-morpholin-4-ylethyl)-1,3-thiazol-2(3H)-ylidene]ethanone;
(2Z)-3-butyl-2-(2-oxo-2-pyridin-2-ylethylidene)-2,3-dihydro-1,3-thiazole-5-carbaldehyde;
(2Z)-3-butyl-2-[2-(3,5-difluorophenyl)-2-oxoethylidene]-2,3-dihydro-1,3-thiazole-5-carbaldehyde;
(2Z)-3-butyl-2-[2-(2-fluorophenyl)-2-oxoethylidene]-2,3-dihydro-1,3-thiazole-5-carbaldehyde;
(2Z)-3-butyl-2-[2-(2,4-difluorophenyl)-2-oxoethylidene]-2,3-dihydro-1,3-thiazole-5-carbaldehyde;
(2Z)-2-(3-butyl-4,5-dimethyl-1,3-thiazol-2(3H)-ylidene)-1-(2-fluorophenyl)ethanone;
(2Z)-2-(3-butyl-4,5-dimethyl-1,3-thiazol-2(3H)-ylidene)-1-pyridin-2-ylethanone;
(2Z)-2-(3-butyl-4,5-dimethyl-1,3-thiazol-2(3H)-ylidene)-1-(3,5-difluorophenyl)ethanone;
(2Z)-2-(3-butyl-3,4,5,6-tetrahydro-2H-cyclopenta[d][1,3]thiazol-2-ylidene)-1-(5-chloro-2-methoxyphenyl)ethanone;
(Z)-2-(5-acetyl-4-methyl-3-((tetrahydrofuran-2-yl)methyl)thiazol-2(3H)-ylidene)-1-(5-chloro-2-methoxyphenyl)ethanone;
(Z)-2-(5-acetyl-3-butyl-4-methylthiazole-2(3H)-ylidene-1-(pyridine-2-yl)ethanone;
(2Z)-2-(3-butyl-5-tert-butyl-4-methyl-1,3-thiazol-2(3H)-ylidene)-1-(3-chlorothien-2-yl)ethanone;
(2Z)-2-(3-butyl-5-tert-butyl-4-methyl-1,3-thiazol-2(3H)-ylidene)-1-(2-chloropyridin-3-yl)ethanone;
(2Z)-2-(3-butyl-5-tert-butyl-4-methyl-1,3-thiazol-2(3H)-ylidene)-1-cyclopentylethanone;
(2Z)-2-(3-butyl-5-tert-butyl-4-methyl-1,3-thiazol-2(3H)-ylidene)-1-cyclohexylethanone;
(2Z)-2-(3-butyl-5-tert-butyl-4-methyl-1,3-thiazol-2(3H)-ylidene)-1-(5-chloro-2-methoxyphenyl)ethanone;
6-[(2Z)-2-(3-butyl-5-tert-butyl-4-methyl-1,3-thiazol-2(3H)-ylidene)ethanoyl]-2,2-dimethyl-2,3-dihydro-4H-pyran-4-one;
(2Z)-1-(1-benzofuran-5-yl)-2-(3-butyl-5-tert-butyl-4-methyl-1,3-thiazol-2(3H)-ylidene)ethanone;
(2Z)-2-(3-butyl-5-tert-butyl-4-methyl-1,3-thiazol-2(3H)-ylidene)-1-(2,2-dimethyltetrahydro-2H-pyran-4-yl)ethanone;
(2Z)-2-(3-butyl-5-tert-butyl-4-methyl-1,3-thiazol-2(3H)-ylidene)-1-(5-fluoro-2-methoxyphenyl)ethanone;
(2Z)-2-(3-butyl-4-phenyl-1,3-thiazol-2(3H)-ylidene)-1-(5-chloro-2-methoxyphenyl)ethanone;
ethyl (2Z)-3-butyl-2-[2-(5-chloro-2-methoxyphenyl)-2-oxoethylidene]-2,3-dihydro-1,3-thiazole-4-carboxylate;
(2Z)-2-(3-butyl-5-methyl-1,3,4-thiadiazol-2(3H)-ylidene)-1-(5-chloro-2-methoxyphenyl)ethanone;
(2Z)-2-(3-butyl-5-methyl-1,3,4-thiadiazol-2(3H)-ylidene)-N-(5-chloro-2-methoxyphenyl)acetamide;
(2Z)-2-(3-butyl-5-tert-butyl-1,3,4-thiadiazol-2(3H)-ylidene)-1-(5-chloro-2-methoxyphenyl)ethanone;
(2Z)-2-(3-butyl-5-tert-butyl-4-methyl-1,3-thiazol-2(3H)-ylidene)-N-(5-chloro-2-methoxyphenyl)acetamide;
(2Z)-2-(3-butyl-4-methyl-1,3-thiazol-2(3H)-ylidene)-1-cyclohexylethanone;
(2Z)-2-(3-butyl-4-methyl-1,3-thiazol-2(3H)-ylidene)-1-(3-chloro-1-benzothien-2-yl)ethanone;
(2Z)-1-(1-adamantyl)-2-(3-butyl-4-methyl-1,3-thiazol-2(3H)-ylidene)ethanone;
(1Z)-1-(3-butyl-5-methyl-1,3,4-thiadiazol-2(3H)-ylidene)-3-cyclopentylacetone;
(2Z)-2-(3-butyl-5-methyl-1,3,4-thiadiazol-2(3H)-ylidene)-1-cyclohexylethanone;
(3Z)-1-[bicyclo[2.2.1]hept-2-yl]-3-(3-butyl-5-methyl-1,3,4-thiadiazol-2(3H)-ylidene)acetone;
(1Z)-1-(3-butyl-5-methyl-1,3,4-thiadiazol-2(3H)-ylidene)-3-(2-chlorophenyl)acetone;
(2Z)-2-(3-butyl-5-methyl-1,3,4-thiadiazol-2(3H)-ylidene)-1-(3-methylthien-2-yl)ethanone;
(2Z)-2-(3-butyl-5-methyl-1,3,4-thiadiazol-2(3H)-ylidene)-1-(1,3-thiazol-4-yl)ethanone;
(2Z)-2-(3-butyl-5-methyl-1,3,4-thiadiazol-2(3H)-ylidene)-1-(2-methylphenyl)ethanone;
(2Z)-2-(3-butyl-5-methyl-1,3,4-thiadiazol-2(3H)-ylidene)-1-(2-chlorophenyl)ethanone;
(2Z)-2-(3-butyl-5-methyl-1,3,4-thiadiazol-2(3H)-ylidene)-1-(3-chlorophenyl)ethanone;
(2Z)-1-(2-bromophenyl)-2-(3-butyl-5-methyl-1,3,4-thiadiazol-2(3H)-ylidene)ethanone;
(2Z)-1-(3-bromophenyl)-2-(3-butyl-5-methyl-1,3,4-thiadiazol-2(3H)-ylidene)ethanone;
(2Z)-1-(4-bromophenyl)-2-(3-butyl-5-methyl-1,3,4-thiadiazol-2(3H)-ylidene)ethanone;
(2Z)-2-(3-butyl-5-methyl-1,3,4-thiadiazol-2(3H)-ylidene)-1-[3-(trifluoromethyl)phenyl]ethanone;
(2Z)-2-(3-butyl-5-methyl-1,3,4-thiadiazol-2(3H)-ylidene)-1-[3-(trifluoromethoxy)phenyl]ethanone;
(2Z)-2-(3-butyl-5-methyl-1,3,4-thiadiazol-2(3H)-ylidene)-1-(2,3-dimethylphenyl)ethanone;
(2Z)-2-(3-butyl-5-methyl-1,3,4-thiadiazol-2(3H)-ylidene)-1-(2,5-dimethylphenyl)ethanone;
(2Z)-2-(3-butyl-5-methyl-1,3,4-thiadiazol-2(3H)-ylidene)-1-(3,4-dimethylphenyl)ethanone;
(2Z)-2-(3-butyl-5-methyl-1,3,4-thiadiazol-2(3H)-ylidene)-1-(3,5-dimethylphenyl)ethanone;
(2Z)-2-(3-butyl-5-methyl-1,3,4-thiadiazol-2(3H)-ylidene)-1-(2,3-dimethoxyphenyl)ethanone;
(2Z)-2-(3-butyl-5-methyl-1,3,4-thiadiazol-2(3H)-ylidene)-1-(2,5-dimethoxyphenyl)ethanone;
(2Z)-2-(3-butyl-5-methyl-1,3,4-thiadiazol-2(3H)-ylidene)-1-(3,5-dimethoxyphenyl)ethanone;
(2Z)-2-(3-butyl-5-methyl-1,3,4-thiadiazol-2(3H)-ylidene)-1-(2,3-dichlorophenyl)ethanone;
(2Z)-2-(3-butyl-5-methyl-1,3,4-thiadiazol-2(3H)-ylidene)-1-(2,4-dichlorophenyl)ethanone;
(2Z)-2-(3-butyl-5-methyl-1,3,4-thiadiazol-2(3H)-ylidene)-1-(2,5-dichlorophenyl)ethanone;
(2Z)-2-(3-butyl-5-methyl-1,3,4-thiadiazol-2(3H)-ylidene)-1-(3,4-dichlorophenyl)ethanone;
(2Z)-2-(3-butyl-5-methyl-1,3,4-thiadiazol-2(3H)-ylidene)-1-(3,5-dichlorophenyl)ethanone;
(2Z)-2-(3-butyl-5-methyl-1,3,4-thiadiazol-2(3H)-ylidene)-1-(5-fluoro-2-methylphenyl)ethanone;
(2Z)-2-(3-butyl-5-methyl-1,3,4-thiadiazol-2(3H)-ylidene)-1-(3-methoxy-4-methylphenyl)ethanone;
(2Z)-2-(3-butyl-5-methyl-1,3,4-thiadiazol-2(3H)-ylidene)-1-(1-naphthyl)ethanone;
(2Z)-2-(3-butyl-5-methyl-1,3,4-thiadiazol-2(3H)-ylidene)-1-(2-naphthyl)ethanone;
(2Z)-2-(3-butyl-5-methyl-1,3,4-thiadiazol-2(3H)-ylidene)-1-(4-tert-butylphenyl)ethanone;
(2Z)-2-(3-butyl-5-methyl-1,3,4-thiadiazol-2(3H)-ylidene)-1-[2-fluoro-5-(trifluoromethyl)phenyl]ethanone;
(2Z)-2-(3-butyl-5-methyl-1,3,4-thiadiazol-2(3H)-ylidene)-1-[2-chloro-5-(trifluoromethyl)phenyl]ethanone;

(2Z)-1-(5-bromo-2-chlorophenyl)-2-(3-butyl-5-methyl-1,3,4-thiadiazol-2(3H)-ylidene)ethanone;

(2Z)-2-(3-butyl-4,5-dimethyl-1,3-thiazol-2(3H)-ylidene)-1-(2,6-difluorophenyl)ethanone;

(2Z)-2-(3-butyl-4,5-dimethyl-1,3-thiazol-2(3H)-ylidene)-1-(2,4-dichlorophenyl)ethanone;

(2Z)-2-(3-butyl-4,5-dimethyl-1,3-thiazol-2(3H)-ylidene)-1-[2-(trifluoromethyl)phenyl]ethanone;

(2Z)-2-(3-butyl-4,5-dimethyl-1,3-thiazol-2(3H)-ylidene)-1-[3-(trifluoromethyl)phenyl]ethanone;

(2Z)-2-(3-butyl-4,5-dimethyl-1,3-thiazol-2(3H)-ylidene)-1-cyclopentylethanone;

4-[(2Z)-2-(3-butyl-4,5-dimethyl-1,3-thiazol-2(3H)-ylidene)ethanoyl]benzonitrile;

(2Z)-2-(3-butyl-4,5-dimethyl-1,3-thiazol-2(3H)-ylidene)-1-(1-naphthyl)ethanone;

(2Z)-2-(3-butyl-4,5-dimethyl-1,3-thiazol-2(3H)-ylidene)-1-(2,5-difluorophenyl)ethanone;

(2Z)-2-(3-butyl-4,5-dimethyl-1,3-thiazol-2(3H)-ylidene)-1-pyridin-3-ylethanone;

(2Z)-1-(1,3-benzodioxol-5-yl)-2-(3-butyl-4,5-dimethyl-1,3-thiazol-2(3H)-ylidene)ethanone;

(2Z)-2-(3-butyl-4,5-dimethyl-1,3-thiazol-2(3H)-ylidene)-1-(2-chloropyridin-3-yl)ethanone;

(2Z)-1-[2,5-bis(trifluoromethyl)phenyl]-2-(3-butyl-4,5-dimethyl-1,3-thiazol-2(3H)-ylidene)ethanone;

(2Z)-2-(3-butyl-4,5-dimethyl-1,3-thiazol-2(3H)-ylidene)-1-[5-fluoro-2-(trifluoromethyl)phenyl]ethanone;

(2Z)-2-(3-butyl-4,5-dimethyl-1,3-thiazol-2(3H)-ylidene)-1-(3-methylthien-2-yl)ethanone;

(2Z)-2-(3-butyl-4,5-dimethyl-1,3-thiazol-2(3H)-ylidene)-1-(5-fluoro-2-methylphenyl)ethanone;

(2Z)-2-(3-butyl-4,5-dimethyl-1,3-thiazol-2(3H)-ylidene)-1-(5-chloro-2-fluorophenyl)ethanone;

(Z)-2-(3-butyl-5-((E)-1-(methoxyimino)ethyl)-4-methylthiazol-2(3H)-ylidene)-1-(5-chloro-2-methoxyphenyl)ethanone;

(Z)-2-(3-butyl-5-((Z)-1-(methoxyimino)ethyl)-4-methylthiazol-2(3H)-ylidene)-1-(5-chloro-2-methoxyphenyl)ethanone;

(2Z)-2-[3-butyl-4-(trifluoromethyl)-1,3-thiazol-2(3H)-ylidene]-1-(5-chloro-2-methoxyphenyl)ethanone;

(2Z)-2-[3-butyl-5-methyl-4-(trifluoromethyl)-1,3-thiazol-2(3H)-ylidene]-1-(5-chloro-2-methoxyphenyl)ethanone;

(Z)-1-(5-chloro-2-methoxyphenyl)-2-(5-((E)-1-(methoxyimino)ethyl)-4-methyl-3-((tetrahydrofuran-2-yl)methyl)thiazol-2(3H)-ylidene)ethanone;

(Z)-1-(5-chloro-2-methoxyphenyl)-2-(5-((Z)-1-(methoxyimino)ethyl)-4-methyl-3-((tetrahydrofuran-2-yl)methyl)thiazol-2(3H)-ylidene)ethanone;

(2Z)-3-butyl-2-[2-(5-chloro-2-methoxyphenyl)-2-oxoethylidene]-5,5-dimethyl-2,3,5,6-tetrahydro-1,3-benzothiazol-7(4H)-one;

(2Z)-2-(3-butyl-5-tert-butyl-1,3-thiazol-2(3H)-ylidene)-1-(5-chloro-2-methoxyphenyl)ethanone;

(2Z)-2-(5-tert-butyl-3-isobutyl-1,3-thiazol-2(3H)-ylidene)-1-(5-chloro-2-methoxyphenyl)ethanone;

(2Z)-2-[3-butyl-4-methyl-5-(2,2,2-trifluoro-1-hydroxy-1-methylethyl)-1,3-thiazol-2(3H)-ylidene]-1-(5-chloro-2-methoxyphenyl)ethanone;

(2Z)-2-[5-tert-butyl-3-(tetrahydrofuran-2-ylmethyl)-1,3-thiazol-2(3H)-ylidene]-1-(5-chloro-2-methoxyphenyl)ethanone;

(2Z)-1-(5-chloro-2-methoxyphenyl)-2-[3-isobutyl-5-methyl-4-(trifluoromethyl)-1,3-thiazol-2(3H)-ylidene]ethanone;

(2E)-2-(3-butyl-4-tert-butyl-1,3-thiazol-2(3H)-ylidene)-1-(5-chloro-2-methoxyphenyl)-2-fluoroethanone;

(2E)-2-(3-butyl-5-tert-butyl-1,3-thiazol-2(3H)-ylidene)-1-(5-chloro-2-methoxyphenyl)-2-fluoroethanone;

(2Z)-2-(3-butyl-5-isopropenyl-1,3-thiazol-2(3H)-ylidene)-1-(5-chloro-2-methoxyphenyl)ethanone;

(1Z)-1-(3-butyl-4,5-dimethyl-1,3-thiazol-2(3H)-ylidene)-4,4-dimethylpentan-2-one;

1-[(2Z)-2-[2-(5-chloro-2-methoxyphenyl)-2-oxoethylidene]-4,5-dimethyl-1,3-thiazol-3(2H)-yl]-3,3-dimethylbutan-2-one;

1-adamantyl (2Z)-(3-butyl-4,5-dimethyl-1,3-thiazol-2(3H)-ylidene)acetate;

(2Z)-2-[3-butyl-5-(3-hydroxy-3-methylbut-1-ynyl)-4-methyl-1,3-thiazol-2(3H)-ylidene]-1-(5-chloro-2-methoxyphenyl)ethanone;

(1Z)-1-[3-(3,3-dimethyl-2-oxobutyl)-4,5-dimethyl-1,3-thiazol-2(3H)-ylidene]-4,4-dimethylpentan-2-one;

(2E)-2-(3-butyl-4,5-dimethyl-1,3-thiazol-2(3H)-ylidene)-1-(5-chloro-2-methoxyphenyl)-2-fluoroethanone;

2-[(2Z)-2-[2-(5-chloro-2-methoxyphenyl)-2-oxoethylidene]-4,5-dimethyl-1,3-thiazol-3(2H)-yl]ethyl 5-chloro-2-methoxybenzoate;

(2Z)-2-(3-butyl-4,5-dimethyl-1,3-thiazol-2(3H)-ylidene)-1-[2-(methylamino)phenyl]ethanone;

(2Z)-1-(5-chloro-2-methoxyphenyl)-2-[3-(4-fluorobutyl)-4,5-dimethyl-1,3-thiazol-2(3H)-ylidene]ethanone;

(2Z)-1-(2-amino-5-chlorophenyl)-2-(3-butyl-4,5-dimethyl-1,3-thiazol-2(3H)-ylidene)ethanone;

ethyl 2-[(2Z)-2-(3-butyl-4,5-dimethyl-1,3-thiazol-2(3H)-ylidene)ethanoyl]-4-chlorophenylcarbamate;

(2E)-2-(3-butyl-4,5-dimethyl-1,3-thiazol-2(3H)-ylidene)-1-(2-chloropyridin-3-yl)-2-fluoroethanone;

ethyl 2-[(2Z)-2-(3-butyl-4,5-dimethyl-1,3-thiazol-2(3H)-ylidene)ethanoyl]-4-chlorophenyl(methyl)carbamate;

methyl 2-[(2Z)-2-(3-butyl-4,5-dimethyl-1,3-thiazol-2(3H)-ylidene)ethanoyl]-4-chlorobenzoate;

(2Z)-2-[3-butyl-4-methyl-5-(2-methyl-1,3-dioxolan-2-yl)-1,3-thiazol-2(3H)-ylidene]-1-(5-chloro-2-methoxyphenyl)ethanone;

2,2,2-trichloro-1,1-dimethylethyl (2Z)-(3-butyl-4,5-dimethyl-1,3-thiazol-2(3H)-ylidene)acetate;

2,2,2-trichloro-1,1-dimethylethyl (2Z)-(3-butyl-5-methyl-1,3,4-thiadiazol-2(3H)-ylidene)acetate;

(2Z)-2-[4-tert-butyl-3-(2-methoxyethyl)-1,3-thiazol-2(3H)-ylidene]-1-(5-chloro-2-methoxyphenyl)ethanone;

(2Z)-2-[4-tert-butyl-3-(tetrahydrofuran-2-ylmethyl)-1,3-thiazol-2(3H)-ylidene]-1-(5-chloro-2-methoxyphenyl)ethanone;

(2Z)-2-[4-tert-butyl-3-(2-piperidin-1-ylethyl)-1,3-thiazol-2(3H)-ylidene]-1-(5-chloro-2-methoxyphenyl)ethanone;

(2Z)-3-butyl-2-[2-(5-chloro-2-methoxyphenyl)-2-oxoethylidene]-N-methyl-2,3-dihydro-1,3-thiazole-4-carboxamide;

(Z)-2-(5-acetyl-3-butylthiazol-2(3H)-ylidene)-1-(5-chloro-2-methoxyphenyl)ethanone;

6-[(2Z)-2-(3-butyl-5-tert-butyl-1,3,4-thiadiazol-2(3H)-ylidene)ethanoyl]-2,2-dimethyl-2,3-dihydro-4H-pyran-4-one;

(2Z)-2-(3-butyl-5-tert-butyl-1,3-thiazol-2(3H)-ylidene)-1-(2-chloropyridin-3-yl)ethanone;

(2Z)-2-(3-butyl-5-tert-butyl-1,3-thiazol-2(3H)-ylidene)-1-(5-fluoro-2-methoxyphenyl)ethanone;

(2Z)-2-(3-butyl-5-tert-butyl-1,3-thiazol-2(3H)-ylidene)-1-(3-chlorothien-2-yl)ethanone;

6-[(2Z)-2-(3-butyl-5-tert-butyl-1,3-thiazol-2(3H)-ylidene)ethanoyl]-2,2-dimethyl-2,3-dihydro-4H-pyran-4-one;

(2Z)-2-(3-butyl-5-tert-butyl-1,3-thiazol-2(3H)-ylidene)-1-(5-iodo-2-methoxyphenyl)ethanone;
(2Z)-1-(1-benzofuran-5-yl)-2-(3-butyl-5-tert-butyl-1,3-thiazol-2(3H)-ylidene)ethanone;
(2Z)-2-(3-butyl-5-tert-butyl-1,3-thiazol-2(3H)-ylidene)-1-(2-ethoxypyridin-3-yl)ethanone;
(2Z)-1-(1-benzofuran-5-yl)-2-(3-butyl-5-isopropenyl-1,3-thiazol-2(3H)-ylidene)ethanone;
(2Z)-2-(3-butyl-5-isopropenyl-1,3-thiazol-2(3H)-ylidene)-1-(2-ethoxypyridin-3-yl)ethanone;
(2Z)-2-[5-tert-butyl-3-(2-methoxyethyl)-1,3,4-thiadiazol-2(3H)-ylidene]-1-(5-chloro-2-methoxyphenyl)ethanone;
(2Z)-2-[5-tert-butyl-3-(2-methoxyethyl)-1,3,4-thiadiazol-2(3H)-ylidene]-1-(2,3-dichlorophenyl)ethanone;
(2Z)-2-(3-butyl-4-methyl-1,3-thiazol-2(3H)-ylidene)-1-[trans-2-phenylcyclopropyl]ethanone;
(2Z)-2-[5-tert-butyl-3-(cyclobutylmethyl)-1,3,4-thiadiazol-2(3H)-ylidene]-1-(5-chloro-2-methoxyphenyl)ethanone;
(2Z)-2-[5-tert-butyl-3-(cyclobutylmethyl)-1,3,4-thiadiazol-2(3H)-ylidene]-1-(2,3-dichlorophenyl)ethanone;
(2Z)-1-(5-chloro-2-methoxyphenyl)-2-[3-(cyclobutylmethyl)-4-methyl-1,3-thiazol-2(3H)-ylidene]ethanone;
(2Z)-1-(5-chloro-2-methoxyphenyl)-2-[3-(cyclobutylmethyl)-5-(1-hydroxy-1-methylethyl)-4-methyl-1,3-thiazol-2(3H)-ylidene]ethanone;
(2Z)-2-[5-bromo-3-(cyclobutylmethyl)-4-methyl-1,3-thiazol-2(3H)-ylidene]-1-(5-chloro-2-methoxyphenyl)ethanone;
(2Z)-1-(5-chloro-2-methoxyphenyl)-2-[3-(cyclobutylmethyl)-1,3-thiazol-2(3H)-ylidene]ethanone;
(2Z)-1-(5-chloro-2-methoxyphenyl)-2-[3-(cyclobutylmethyl)-4-methyl-5-(2,2,2-trifluoro-1-hydroxy-1-methylethyl)-1,3-thiazol-2(3H)-ylidene]ethanone;
(2Z)-2-[3-butyl-5-(1-hydroxy-1-methylethyl)-1,3-thiazol-2(3H)-ylidene]-1-(5-chloro-2-methoxyphenyl)ethanone;
(2Z)-1-(5-chloro-2-methoxyphenyl)-2-[3-(cyclobutylmethyl)-5-(1-hydroxy-1-methylethyl)-1,3-thiazol-2(3H)-ylidene]ethanone;
(2Z)-2-[5-tert-butyl-3-(cyclobutylmethyl)-1,3,4-thiadiazol-2(3H)-ylidene]-1-(2-chloropyridin-3-yl)ethanone;
(2Z)-2-[5-tert-butyl-3-(cyclobutylmethyl)-1,3,4-thiadiazol-2(3H)-ylidene]-1-(2-ethoxypyridin-3-yl)ethanone;
(2Z)-2-[5-tert-butyl-3-(cyclobutylmethyl)-1,3,4-thiadiazol-2(3H)-ylidene]-1-[4-(trifluoromethyl)pyridin-3-yl]ethanone;
(2Z)-2-(3-butyl-5-tert-butyl-1,3,4-thiadiazol-2(3H)-ylidene)-1-(2,3-dichlorophenyl)ethanone;
(2Z)-1-(5-chloro-2-methoxyphenyl)-2-[3-(cyclobutylmethyl)-5-(1-hydroxy-1-methylpropyl)-4-methyl-1,3-thiazol-2(3H)-ylidene]ethanone;
(2Z)-1-(5-chloro-2-methoxyphenyl)-2-[3-(cyclobutylmethyl)-5-(1-ethyl-1-hydroxypropyl)-4-methyl-1,3-thiazol-2(3H)-ylidene]ethanone;
(2Z)-1-(5-chloro-2-methoxyphenyl)-2-[3-(cyclobutylmethyl)-5-(2-fluoro-1-hydroxy-1-methylethyl)-4-methyl-1,3-thiazol-2(3H)-ylidene]ethanone;
(2Z)-1-(5-chloro-2-methoxyphenyl)-2-[3-(cyclobutylmethyl)-5-(2,2-difluoro-1-hydroxy-1-methylethyl)-4-methyl-1,3-thiazol-2(3H)-ylidene]ethanone;
(2Z)-2-(3-butyl-5-tert-butyl-1,3-thiazol-2(3H)-ylidene)-1-[2-(trifluoromethyl)phenyl]ethanone;
(2Z)-1-(5-chloro-2-methoxyphenyl)-2-[3-(cyclobutylmethyl)-1,3,4-thiadiazol-2(3H)-ylidene]ethanone;
ethyl (2Z)-3-butyl-2-[2-(5-chloro-2-methoxyphenyl)-2-oxoethylidene]-5-(1-hydroxy-1-methylethyl)-2,3-dihydro-1,3-thiazole-4-carboxylate;
(2Z)-3-butyl-2-[2-(5-chloro-2-methoxyphenyl)-2-oxoethylidene]-6,6-dimethyl-3,6-dihydrofuro[3,4-d][1,3]thiazol-4(2H)-one;
(2Z)-2-(3-butyl-4,5-dimethyl-1,3-thiazol-2(3H)-ylidene)-1-(5-chloro-2-hydroxyphenyl)ethanone;
tert-butyl (2Z)-3-butyl-2-[2-(5-chloro-2-methoxyphenyl)-2-oxoethylidene]-2,3-dihydro-1,3-thiazol-4-ylcarbamate;
(2Z)-2-(3-butyl-4,5-dimethyl-1,3-thiazol-2(3H)-ylidene)-1-[5-chloro-2-(dimethylamino)phenyl]ethanone;
(2Z)-1-(5-chloro-2-methoxyphenyl)-2-[3-(cyclobutylmethyl)-5-(1-ethyl-1-hydroxypropyl)-1,3-thiazol-2(3H)-ylidene]ethanone;
(2Z)-2-[5-(1-amino-1-ethylpropyl)-3-(cyclobutylmethyl)-1,3-thiazol-2(3H)-ylidene]-1-(5-chloro-2-methoxyphenyl)ethanone;
(2Z)-2-(3-butyl-5-tert-butyl-1,3-thiazol-2(3H)-ylidene)-1-[6-chloro-4-(trifluoromethyl)pyridin-3-yl]ethanone;
(2Z)-3-butyl-2-[2-(5-chloro-2-methoxyphenyl)-2-oxoethylidene]-6,6-diethyl-2,3,5,6-tetrahydro-4H-pyrrolo[3,4-d][1,3]thiazol-4-one;
(2Z)-2-[3-butyl-5-[2-fluoro-1-(fluoromethyl)-1-hydroxyethyl]-1,3-thiazol-2(3H)-ylidene]-1-(5-chloro-2-methoxyphenyl)ethanone;
(2Z)-2-(3-butyl-5-isopropenyl-1,3-thiazol-2(3H)-ylidene)-1-[6-chloro-4-(trifluoromethyl)pyridin-3-yl]ethanone;
(2Z)-2-[3-butyl-4-(1-hydroxy-1-methylethyl)-1,3-thiazol-2(3H)-ylidene]-1-(5-chloro-2-methoxyphenyl)ethanone;
(Z)-2-(4-acetyl-3-butylthiazol-2(3H)-ylidene)-1-(5-chloro-2-methoxyphenyl)ethanone;
(2Z)-1-(5-chloro-2-methoxyphenyl)-2-[3-(cyclobutylmethyl)-5-[2-fluoro-1-(fluoromethyl)-1-hydroxyethyl]-4-methyl-1,3-thiazol-2(3H)-ylidene]ethanone;
ethyl (2Z)-5-(1-amino-1-methylethyl)-3-butyl-2-[2-(5-chloro-2-methoxyphenyl)-2-oxoethylidene]-2,3-dihydro-1,3-thiazole-4-carboxylate;
(2Z)-3-butyl-2-[2-(5-chloro-2-methoxyphenyl)-2-oxoethylidene]-6,6-dimethyl-2,3,5,6-tetrahydro-4H-pyrrolo[3,4-d][1,3]thiazol-4-one; and
(Z)-2-(3-butyl-4,5-dimethylthiazol-2(3H)-ylidene)-1-(5-chloro-2-methoxyphenyl)ethanethione.

Compounds of the present invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

For example, compounds of formula (I) wherein $R_1$ is tetrahydrofuran-2-ylmethyl can have stereoisomers including, but not limited to, those shown below:

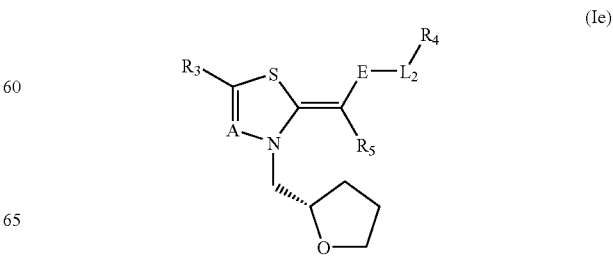

-continued

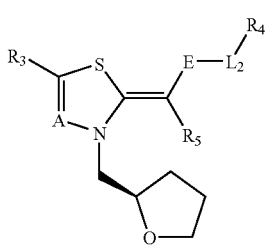

(If)

wherein A, $R_3$, $R_4$, $R_5$, E, and $L_2$ are as disclosed in the Summary and the Detailed Description sections. It is understood that embodiments for A, $R_3$, $R_4$, $R_5$, E, and $L_2$, and combinations of embodiments, including particular, and more particular embodiments as described for formula (I) are also contemplated for compounds of formulae (Ie), and (If).

The present invention contemplates various stereoisomers (including enantiomers and diastereomers) and mixtures thereof. Individual stereoisomers of compounds of the present invention may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

c. BIOLOGICAL DATA (i) In Vitro Methods—$CB_2$ and $CB_1$ Radioligand Binding Assays:

The $CB_1$ and $CB_2$ radioligand binding assays described herein are utilized to ascertain the selectivity of compounds of the present invention for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 µg/well for human $CB_2$) into wells of a deep well plate containing [$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 µl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 µM. The addition of 10 µM unlabeled CP-55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 µg/well for rat $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 µl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H] CP-55,940 and five concentrations of displacing ligands selected from the range of 0.01 nM to 10 µM. The addition of 10 µM unlabeled CP-55,940 (Tocris, Ellisville, Mo.) was used to assess nonspecific binding.

Representative compounds of the present invention bound to $CB_2$ receptors with a $K_i$ of less than about 1,000 nM, preferably less than 400 nM, more preferably less than 200 nM and, most preferably lower than 100 nM.

HEK293 human $CB_1$ membranes were purchased from Perkin Elmer. Binding was initiated by the addition of membranes (8-12 µg per well) into wells (Scienceware 96-well DeepWell plate, VWR, West Chester, Pa.) containing [$^3$H] CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 µL. After incubation (30° C. for 90 minutes), binding was terminated by the addition of 300 µL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20

(both from Perkin Elmer, Boston, Mass.). Competition experiments were conducted with 1 nM [$^3$H]CP-55,940 and five concentrations (1 nM to 10 μM) of displacing ligands. The addition of 10 μM unlabeled CP-55,940 (Tocris, Ellisville, Mo.) was used to assess nonspecific binding.

Representative compounds of the present invention bound to $CB_1$ receptors with $K_i$ of about 10 fold to about 1000 fold higher than that for $CB_2$ receptors. These results show that the compounds of the present invention preferably bind to $CB_2$ receptors, therefore are selective ligands for the $CB_2$ receptor.

(ii) In Vivo Data:

Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Incisional Model of Postoperative Pain

A skin incision model of postoperative pain was produced using the procedures as described in Brennan et al., 1996, Pain, 64, 493. All rats were anesthetized with isoflurane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as described in Chaplan, S. R., F. W. Bach, J. W. Pogrel, J. M. Chung and T. L. Yaksh, 1994, Quantitative Assessment of Tactile Allodynia in the Rat Paw, J. Neurosci. Methods, 53, 55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol. 20, 441).

Representative compounds of the present invention showed a statistically significant change in paw withdrawal latency versus a saline vehicle at less than about 300 micromoles/kg in the incisional model of postoperative pain. In a more preferred embodiment, compounds of the present invention showed efficacy at less than about 50 micromoles/kg in the incisional model of postoperative pain.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) can be used to test the compounds of the present invention The left L5 and L6 spinal nerves of the rat are isolated adjacent to the vertebral column and tightly ligated with a 5-0 silk suture distal to the DRG, and care is taken to avoid injury of the L4 spinal nerve. Sham rats undergo the same procedure, but without nerve ligation. All animals are allowed to recover for at least one week and not more than three weeks prior to assessment of tactile allodynia.

Tactile allodynia is measured using calibrated von Frey filaments (Stoelting, Wood Dale, Ill.) as described in Chaplan, S. R., F. W. Bach, J. W. Pogrel, J. M. Chung and T. L. Yaksh, 1994, Quantitative Assessment of Tactile Allodynia in the Rat Paw, J. Neurosci. Methods, 53, 55. Rats are placed into inverted individual plastic containers (20×12.5×20 cm) on top of a suspended wire mesh grid, and acclimated to the test chambers for 20 minutes. The von Frey filaments are presented perpendicularly to the plantar surface of the selected hind paw, and then hold in this position for approximately 8 sec with enough force to cause a slight bend in the filament. Positive responses include an abrupt withdrawal of the hind paw from the stimulus, or flinching behavior immediately following removal of the stimulus. A 50% withdrawal threshold is determined using an up-down procedure (Dixon, W. J., 1980, Efficient analysis of experimental observations, Ann. Rev. Pharmacol. Toxicol. 20, 441). Only rats with a baseline threshold score of less that 4.25 g are used in this study, and animals demonstrating motor deficit are excluded. Tactile allodynia thresholds are also assessed in several control groups, including naive, sham-operated, and saline infused animals as well as in the contralateral paws of nerve-injured rats.

Capsaicin-Induced Secondary Mechanical Hypersensitivity:

Rats were allowed to acclimate to the study room for 1 hour. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds are injected (i.p.) 30 min before testing (150 min post-capsaicin).

Tactile allodynia was measured as described above.

Certain compounds of the present invention showed a statistically significant change in paw withdrawal latency versus a saline vehicle at less than about 300 micromoles/kg. In a more preferred embodiment, compounds of the present invention showed efficacy of less than about 50 micromoles/kg.

d. METHODS OF USING THE COMPOUNDS

One embodiment of the present invention provides a method for treating pain (for example, neuropathic pain or nociceptive pain) in a mammal in need of such treatment. The method comprises administering to the mammal a therapeutically effective amount of a compound of formula (I) or a pharmaceutically acceptable salt thereof.

Another embodiment of the present invention provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of formula (I) or a pharmaceutically acceptable salt thereof.

Yet another embodiment of the present invention relates to a method for providing neuroprotection in a mammal in need of such treatment. This method comprises administering to the mammal a therapeutically effective amount of a compound of formula (I) or a pharmaceutically acceptable salt thereof.

In addition to the data contained herein, several lines of evidence support the assertion that $CB_2$ receptors play a role in analgesia. For example, Zimmer et al. have reported that the nonselective cannabinoid agonist $\Delta^9$-THC retains some analgesic efficacy in $CB_1$ receptor knockout mice (Zimmer, A., et al., Proc. Nat. Acad. Sci., 1999, 96, 5780-5785). HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260). The analgesic effects induced by these $CB_2$-selective ligands are blocked by $CB_2$ and not by $CB_1$ receptor antagonists. Furthermore, at fully efficacious doses, AM-1241 and GW405833 are devoid of typical $CB_1$ receptor-mediated CNS side effects, providing evidence that modulation of $CB_2$ receptors can produce broad-spectrum pain relief with reduced side-effect liability.

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators are useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. They are quiescent and resting having a ramified morphology as long as the CNS is healthy. Microglia express a variety of receptors enabling them to survey the CNS and respond to pathological events. Insult or injury to the CNS leads to microglial cell activation, which is characterized by various morphological changes allowing response to the lesion. Ramifications are retracted and microglia are transformed into amoeboid-like cells with phagocytic function. They can proliferate, rapidly migrate to the site of injury, and produce and release cytokines, chemokines and complement components (Watkins L. R., et al., Trends in Neuroscience, 2001, 24(8), 450; Kreutzberg, G. W., Trends Neurosci., 1996, 19, 312-318). $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. It is conceivable that $CB_2$ receptors may be more susceptible to pharmacological effects during neuroinflammation (Walter, L., Stella, N., Br. J. Pharmacol. 2004, 141, 775-785). Neuroinflammation occurs in several neurodegenerative diseases, and induction of microglial $CB_2$ receptors has been observed (Carrier, E. J., et al., Current Drug Targets—CNS & Neurological Disorders, 2005, 4, 657-665). Thus, $CB_2$ ligands may be clinically useful for the treatment of neuroinflammation.

$CB_2$ receptor expression has been detected in perivascular microglial cells within normal, healthy human cerebellum (Nunez, E., et al., Synapse, 2004, 58, 208-213). Perivascular cells are immunoregulatory cells located adjacent to CNS blood vessels and, along with parenchymal microglia and astrocytes, they play a pivotal role in maintaining CNS homeostasis and blood-brain barrier functionality (Williams, K., et al., Glia, 2001, 36, 156-164). $CB_2$ receptor expression has also been detected on cerebromicrovascular endothelial cells, which represent a main component of the blood-brain barrier (Golech, S. A., et al., Mol. Brain. Res., 2004, 132, 87-92). A recent report demonstrated that $CB_2$ receptor expression is up-regulated in the brains of macaques with simian immunodeficiency virus-induced encephalitis (Benito, C., et al., J. Neurosci. 2005, 25(10), 2530-2536). Thus, compounds that affect $CB_2$ signaling may protect the blood-brain barrier and be clinically useful in the treatment of neuroinflammation and a variety of neuroinflammatory disorders including retroviral encephalitis, which occurs with human immunodeficiency virus (HIV) infection in the CNS.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators represents a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators represents a unique approach for the treatment of liver fibrosis.

$CB_2$ receptors are involved in the neuroprotective and anti-inflammatory mechanisms induced by the interleukin-1 receptor antagonist (IL-Ira) (Molina-Holgado, F., et al., J. Neurosci., 2003, 23(16), 6470-6474). IL-Ira is an important anti-inflammatory cytokine that protects against ischemic, excitotoxic, and traumatic brain insults. $CB_2$ receptors play a role in mediating these neuroprotective effects indicating that $CB_2$ ligands are useful in the treatment of traumatic brain injury, stroke, and in mitigating brain damage.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators have utility as antitussive agents for the treatment of pulmonary inflammation, chronic cough, and a variety of airway inflammatory diseases including but not limited to asthma, chronic obstructive pulmonary disease, and pulmonary fibrosis.

Osteoporosis is a disease characterized by reduced bone mass, which leads to deterioration of bone microstructure and increased susceptibility to fracture. Age is associated with bone loss and it is estimated that 50% of all Caucasian women will have osteoporosis by the age of 80 (Ralston, S. H., Curr. Opin. Pharmacol., 2003, 3, 286-290). There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators are useful for the treatment and prevention of osteoporosis, osteoarthritis, and bone disorders.

Arthrosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor are clinically useful for the treatment of atherosclerosis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-

459). Thus, $CB_2$ modulators have utility for the treatment or prophylaxis of cardiovascular disease and the development of myocardial infarction.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or animal range from about 0.1 mg/kg body weight to about 100 mg/kg body weight. More preferable doses can be in the range of from about 0.3 to 30 mg/kg body weight. If desired, the effective daily dose can be divided into multiple doses for purposes of administration. Consequently, single dose compositions may contain such amounts or submultiples thereof to make up the daily dose.

e. PHARMACEUTICAL COMPOSITIONS

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising a compound of formula (I), or a pharmaceutically acceptable salt thereof, and one or more pharmaceutically acceptable carriers, alone or in combination with one or more nonsteroidal anti-inflammatory drug (NSAID).

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled.

Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. GENERAL SYNTHESIS

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups E, $R_1$, $R_2$, $R_3$, $R_4$, $R_5$, A, $L_2$, $R_e$, $R_p$, and $R^z$ have the meanings as set forth in the summary section unless otherwise noted, can be synthesized as shown in Schemes 1-7.

As used in the descriptions of the schemes and the examples, certain abbreviations are intended to have the following meanings: DCC for 1,3-dicyclohexylcarbodiimide, DIEA for diisopropylethyl amine, DMA for N,N-dimethylacetamide, DMAP for 4-dimethylaminopyridine, DMF for N,N-dimethylformamide, DMSO for dimethyl sulfonamide, EtOAc for ethyl acetate, $CHCl_3$ for chloroform, $CH_2Cl_2$ for dichloromethane, $CH_3CN$ for acetonitrile, DBU for 1,8-diazabicyclo[5.4.0]undec-7-ene, HATU for O-(7-azabenzotriazol-1-yl)-N,N,N',N'-tetramethyluronium hexafluorophosphate, HPLC for high performance liquid chromatography, THF for tetrahydrofuran, MeOH for methanol, TEA for triethyl amine, Ph for phenyl, TBAF for tetrabutyl ammonium fluoride.

Compounds of general formula (I) wherein $R_5$ is hydrogen, E is C(O), and $L_2$ is $N(R_e)$ can be prepared using, for example, using the general procedures as outlined in Scheme 1.

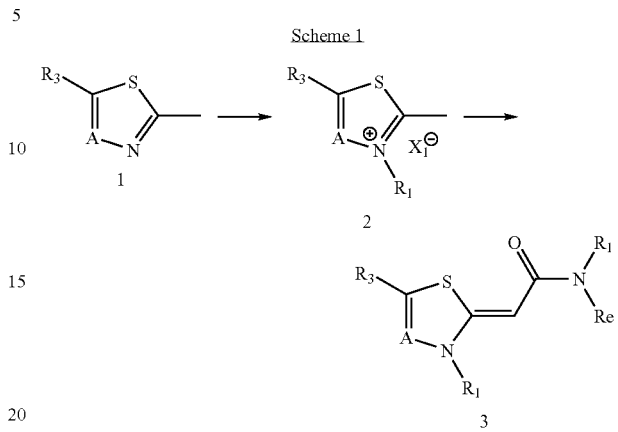

Scheme 1

Compounds of formula 1 when heated in the presence of halides of formula $R_1$—$X_1$, wherein $X_1$ is halogen, in a solvent such as, but not limited to, acetonitrile, provides compounds of formula 2. For example, the reaction conditions may be heated for 72-96 hours to effect complete consumption of starting material. Compounds of formula 2 when treated with isocyanates of formula $R_4R_eNCO$ in the presence of a base such as 1,8-diazabicyclo[5.4.0]undec-7-ene, and in a solvent such as, but not limited to, dichloromethane provides compounds of formula 3.

Compounds of general formula (I) wherein $R_5$ is hydrogen can be prepared using general procedure as shown in Scheme 2.

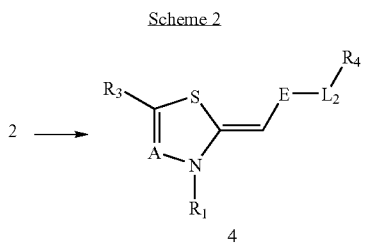

Scheme 2

Compounds of formula 2, when treated with compounds of formula $R_4L_2ECl$, in the presence of 4-dimethylaminopyridine, and in a solvent such as, but not limited to, dichloromethane, provides compounds of formula 4.

Compounds of general formula (I) wherein E is C(O) and $R_5$ is hydrogen can be synthesized using general procedures as outlined below:

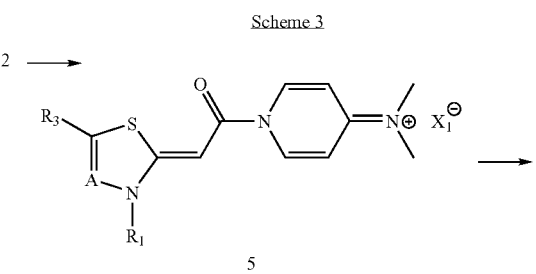

Scheme 3

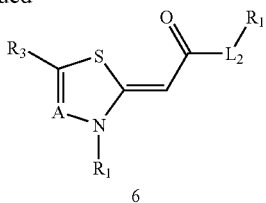

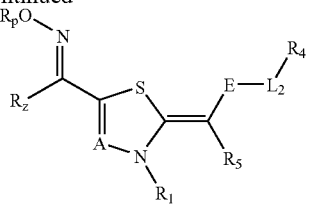

Compounds of formula 2 when treated with a reagent that can provide an electrophilic carbonyl group such as, but not limited to, di-tert butyl dicarbonyl or carbonyl diimidazole, provide intermediates of formula 5. The reaction is generally conducted in the presence of 4-dimethylaminopyridine and in a solvent such as DMF. Compounds of formula 5 when treated with appropriate reagents provide compounds of formula 6. For example, compounds of formula 5 when treated with primary amines, secondary amines, alcohols, or a heterocycle containing a secondary nitrogen atom, under heated conditions, provides compounds of formula 6 wherein $L_2$ is $N(R_e)$ or O, or provides compounds wherein $L_2$ is a bond and $R_4$ is a heterocycle containing a secondary amine having the nitrogen atom of the heterocyclic ring attached to the carbonyl functional group. For example, the transformation can be effected by heating compounds of formula 5 with an appropriate reagent such as $R_4OH$, $R_4$—$N(R_e)(H)$ or a heterocycle containing a secondary nitrogen, in the presence of a non-nucleophilic base such as diisopropylethylamine or triethylamine, and in a solvent such as but not limited to acetonitrile or THF.

Compounds of general formula (I) wherein E is C(O) and A is $C(R_2)$ can be prepared using general procedure as shown in Scheme 4.

Scheme 4

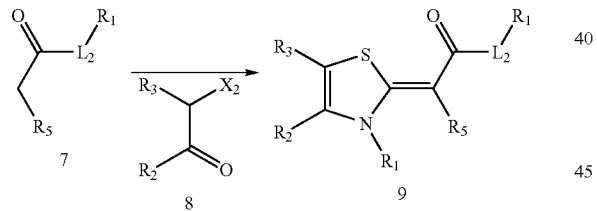

Compounds of formula 7 when treated with sodium hydride in DMF and $R_1$—N=C=S at about 0° C., followed by the addition of compounds of formula 8 wherein $X_2$ is halogen and then heating, provide compounds of formula 9.

Compounds of general formula (I) wherein $R_3$ is $R_pON=C(R^z)$— can be prepared using general procedures as shown in Scheme 5.

Scheme 5

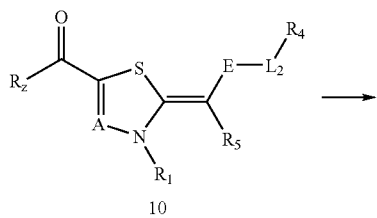

Compounds of formula 10 when treated with compounds of formula $H_2N$—$OR_p$ provide compounds of formula 11. Typical conditions for this reaction include stirring the reagents in a solvent such as pyridine or mixtures of pyridine and ethanol at ambient temperature for about 16-24 hours.

Compounds of general formula (I) wherein E is C(O) and $R_5$ is fluorine can be prepared, for example, by heating compounds of formula 6 with about equimolar amounts of Selectfluor™, in a suitable solvent such as, acetonitrile, toluene, dioxane, chloroform, and the like, as shown in Scheme 6.

Scheme 6

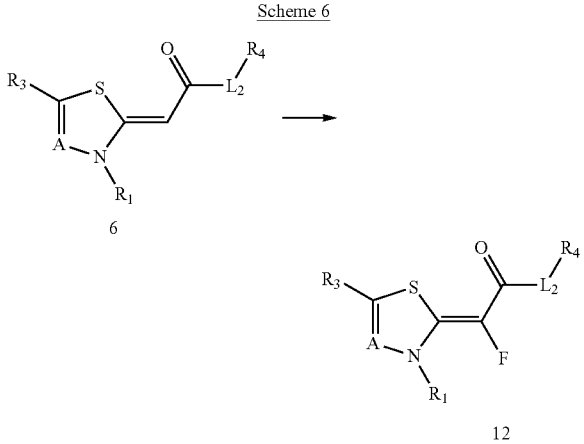

Compounds of general formula (I) wherein E is C(S) and $L_2$ is a bond can be obtained, for example, by heating compounds of formula 13 with phosphorus pentasulfide in pyridine or THF, as shown in Scheme 7.

Scheme 7

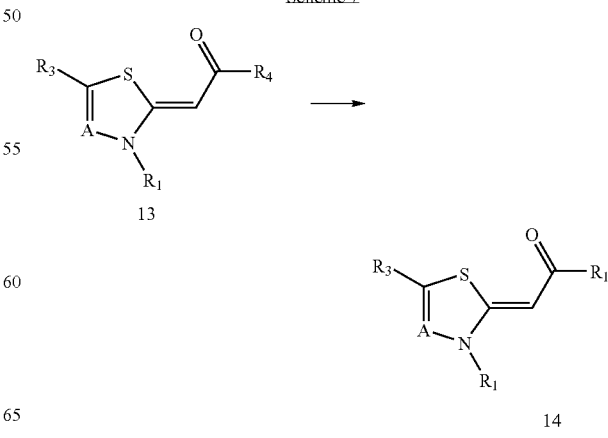

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

g. EXAMPLES

Example 1

(2Z)-2-(3-butyl-4,5-dimethyl-1,3-thiazol-2(3H)-ylidene)-1-(5-chloro-2-methoxyphenyl)ethanone Example 1A 3-butyl-2,4,5-trimethyl-1,3-thiazol-3-ium iodide A mixture of 2,4,5-trimethylthiazole (1.3 g, 10 mmol) and n-butyl iodide (7.4 g, 40 mmol) in anhydrous acetonitrile (30 mL) was refluxed for 72 hours and then concentrated under reduced pressure to provide the crude thiazolium salt. $^1$H NMR (300 MHz, DMSO-d$_6$) δ 0.95 (t, J=7 Hz, 3H), 1.39 (sextet, J=7 Hz, 2H), 1.65 (m, 2H), 2.43 (s, 6H), 2.96 (s, 3H), 4.25 (m, 2H).

Example 1B (Procedure A)

(2Z)-2-(3-butyl-4,5-dimethyl-1,3-thiazol-2(3H)-ylidene)-1-(5-chloro-2-methoxyphenyl)ethanone To a solution of Example 1A (780 mg, 2.5 mmol) and 5-chloro-2-methoxy-benzoyl chloride (515 mg, 2.5 mmol) in CH$_2$Cl$_2$ (25 mL) under N$_2$ atmosphere at 0° C. was added 4-dimethylaminopyridine (DMAP) (1.22 g. 10 mmol) and the mixture was allowed to warm to room temperature. The mixture was stirred for 20 hours, washed sequentially with saturated sodium bicarbonate and brine. The methylene chloride solution was dried (anhydrous MgSO$_4$), filtered and concentrated under reduced pressure. The residue was purified by chromatography over silica gel (hexane-EtOAc 1:1 as eluent) to provide the title compound. $^1$H NMR (300 MHz, DMSO-d$_6$) δ 0.96 (t, J=7 Hz, 3H), 1.39 (sextet, J=7 Hz, 2H), 1.66 (quintet, J=7 Hz, 2H), 2.15 (s, 3H), 2.20 (s, 3H), 3.85 (s, 3H), 3.90 (t, J=7 Hz, 2H), 6.54 (s, 1H), 7.10 (d, J=9 Hz, 1H), 7.40 (dd, J=9 Hz, 3 Hz, 1H), 7.65 (d, J=3 Hz, 1H); MS (ESI) m/z 352 (M+H)$^+$. Anal calcd for C$_{18}$H$_{22}$ClNO$_2$S: C, 61.44; H, 6.30; N, 3.98. Found: C, 61.34; H, 6.17; N, 3.86.

Example 1C (Procedure B)

(2Z)-2-(3-butyl-4,5-dimethyl-1,3-thiazol-2(3H)-ylidene)-1-(5-chloro-2-methoxyphenyl)ethanone A mixture of Example 1A (155 mg (0.5 mmol) and 5-chloro-2-methoxy-benzoic acid N-hydroxysuccinimide ester (142 mg, 0.5 mmol) in anhydrous DMF (5 mL) at 0° C. was treated with a solution of DBU (0.076 mL, 0.5 mmol) in DMF (5 mL) and then allowed to warm to ambient temperature and stirred for 16 hours. The mixture was partitioned between water and EtOAc. The EtOAc layer was washed with water, brine, dried (anhydrous MgSO$_4$), filtered and concentrated under reduced pressure. The residue was purified by column chromatography (Hexane-EtOAc 1:1) to provide the title compound.

Example 2

(2Z)-1-(1-adamantyl)-2-(3-butyl-4,5-dimethyl-1,3-thiazol-2(3H)-ylidene)ethanone

The title compound was prepared as described in Example 1B by replacing 5-chloro-2-methoxy-benzoyl chloride with 1-adamantanecarbonyl chloride. $^1$H NMR (300 MHz, DMSO-d$_6$) δ 0.93 (t, J=7 Hz, 3H), 1.35 (sextet, J=7 Hz, 2H), 1.58 (quintet, J=7 Hz, 2H), 1.65 (m, 6H), 1.76 (m, 6H), 1.97 (m, 3H), 2.08 (s, 3H), 2.12 (s, 3H), 3.84 (m, 2H), 5.81 (s, 1H); MS (ESI) m/z 346 (M+H)$^+$. Anal calcd for C$_{21}$H$_{31}$NOS.0.2H$_2$O: C, 72.24; H, 9.06; N, 4.01. Found: C, 72.35; H, 9.04; N, 3.68.

Example 3 tert-butyl (2Z)-(3-butyl-4,5-dimethyl-1,3-thiazol-2 (3H)-ylidene)acetate

DMAP (200 mg, 1.6 mmol) was added at 0° C. to a solution of Example 1A (440 mg, 1.4 mmol) and di-t-butyl-dicarbonate (352 mg, 1.6 mmol) in DMF (15 mL). The mixture was stirred for 18 hours at room temperature and then purified by column chromatography over silica gel (Hexane-EtOAc 1:1 as eluent) to provide the title compound. $^1$H NMR (300 MHz, DMSO-d$_6$) δ 0.91 (t, J=7 Hz, 3H), 1.36 (sextet, J=7 Hz, 2H), 1.40 (s, 9H), 1.50 (m, 2H), 2.03 (s, 3H), 2.06 (s, 3H), 3.66 (m, 2H), 4.87 (s, 1H); MS (ESI) m/z 284 (M+H)$^+$. Anal calcd for C$_{15}$H$_{25}$NO$_2$S.0.5H$_2$O: C, 61.61; H, 8.96; N, 4.79. Found: C, 61.25; H, 8.80; N, 4.75.

Example 4

N-[1-[(2Z)-2-(3-butyl-4,5-dimethyl-1,3-thiazol-2 (3H)-ylidene)ethanoyl]pyridin-4(1H)-ylidene]-N-methylmethanaminium iodide From the chromatographic purification of Example 3 was obtained the title compound after changing the elution solvent to (9:1) CH$_2$Cl$_2$-MeOH. $^1$H NMR (300 MHz, DMSO-d$_6$) δ 1.00 (t, J=7 Hz, 3H), 1.38 (sextet, J=7 Hz, 2H), 1.64 (m, 2H), 2.03 (s, 3H), 2.06 (s, 3H), 3.31 (s, 6H), 4.14 (t, J=7 Hz, 2H), 6.23 (s, 1H), 7.07 (d, J=8 Hz, 2H), 8.83 (d, J=8 Hz, 2H); MS (ESI) m/z 332 (M)$^+$. Anal calcd for C$_{18}$H$_{26}$IN$_3$OS: C, 47.06; H, 5.70; N, 9.15. Found: C, 47.08; H, 5.85; N, 9.02.

Example 5

(2Z)-1-(5-chloro-2-methoxyphenyl)-2-1,3-(2-methoxyethyl)-4,5-dimethyl-[3-thiazol-2(3H)-ylidene]ethanone Example 5A 3-(2-methoxyethyl)-2,4,5-trimethyl-1,3-thiazol-3-ium bromide The title compound was prepared as described in Example 1A by substituting 2-bromoethyl methyl ether for n-butyl iodide.

Example 5B (2Z)-1-(5-chloro-2-methoxyphenyl)-2-1,3-(2-methoxyethyl)-4,5-dimethyl-[3-thiazol-2(3H)-ylidene]ethanone The title compound was prepared as described in Example 1B by substituting Example 5A for Example 1A. $^1$H NMR (300 MHz, DMSO-d$_6$) δ 2.14 (s, 3H), 2.18 (s, 3H), 3.24 (s, 2H), 3.63 (t, J=6 Hz, 2H), 3.84 (s, 3H), 4.11 (t, J=6 Hz, 2H), 6.48 (s, 1H), 7.10 (d, J=9 Hz, 1H), 7.39 (d-d, J=9 Hz, 3 Hz, 1H), 7.61 (d, J=3 Hz, 1H); MS (ESI) m/z 354 (M+H)$^+$. Anal calcd for C$_{17}$H$_{20}$ClNO$_3$S: C, 57.70; H, 5.70; N, 3.96. Found: C, 57.66; H, 5.73; N, 3.85.

Example 6

(2Z)-2-(3-butyl-5-methyl-1,3-thiazol-2(3H)-ylidene)-1-(5-chloro-2-methoxyphenyl)ethanone The title compound was prepared as described in Example 1B by substituting 3-butyl-2,4,5-trimethylthiazol-3-ium iodide for Example 1A. $^1$H NMR (300 MHz, DMSO-d$_6$) δ 0.96 (t, J=7 Hz, 3H), 1.39 (sextet, J=7 Hz, 2H), 1.66 (quintet, J=7 Hz, 2H), 2.21 (d, J=1.5 Hz, 3H), 3.85 (s, 3H), 3.93 (t, J=7 Hz, 2H), 6.50 (s, 1H), 7.10 (d, J=9 Hz, 1H), 7.13 (d, J=1.5 Hz, 1H), 7.40 (d-d, J=9 Hz, 3 Hz, 1H), 7.64 (d, J=3 Hz, 1H); MS (ESI) m/z 338 (M+H).

Example 7

(2Z)-2-(3-butyl-4,5-dimethyl-1,3-thiazol-2(3H)-ylidene)-1-cyclohexylethanone

The title compound was prepared as described in Example 1B by replacing 5-chloro-2-methoxy-benzoyl chloride with cyclohexanecarbonyl chloride. $^1$H NMR (300 MHz, DMSO-d$_6$) δ 0.96 (t, J=7 Hz, 3H), 1.25 (m, 8H), 1.66 (m, 6H), 2.07 (s, 3H), 2.12 (s, 3H), 2.18 (m, 1H), 3.81 (t, J=7 Hz, 2H), 5.74 (s, 1H); MS (ESI) m/z 294 (M+H)$^+$.

Example 8

(2Z)-2-(3-butyl-4,5-dimethyl-1,3-thiazol-2(3H)-ylidene)-N-cyclohexylacetamide

To a solution of Example 1A (123 mg, 0.4 mmol) and cyclohexyl isocyanate (63 mg, 0.5 mmol) in CH$_2$Cl$_2$ (20 mL) at 0° C. was added dropwise a solution of DBU (0.076 mL, 0.5 mmol) in CH$_2$Cl$_2$ (5 mL). The mixture was allowed to warm to room temperature and stirred for 14 hours. The mixture was washed sequentially with water, brine and dried over anhydrous MgSO$_4$, filtered and concentrated under reduced pressure. The residue was purified by column chromatography over silica gel (CH$_2$Cl$_2$-MeOH 9:1) to provide the title compound. $^1$H NMR (300 MHz, DMSO-d$_6$) δ 0.96 (t, J=7 Hz, 3H), 1.10 (m, 3H), 1.29 (m, 4H), 1.51 (m, 3H), 1.70 (m, 4H), 1.95 (s, 3H), 2.02 (s, 3H), 3.33 (m, 3H), 5.02 (s, 1H), 6.74 (br d, J=7 Hz, 1H); MS (ESI) m/z 309 (M+H)$^+$. Anal calcd for C$_{17}$H$_{28}$N$_2$OS.0.25H$_2$O: C, 65.24; H, 9.18; N, 8.95. Found: C, 65.49; H, 9.30; N, 8.93.

Example 9

4-[(2Z)-2-(3-butyl-4,5-dimethyl-1,3-thiazol-2(3H)-ylidene)ethanoyl]morpholine

A mixture of product from Example 4 (46 mg, 0.1 mmol) and morpholine (175 mg, 2 mmol) in dioxane (10 mL) was heated to 80° C. for 2 hours then concentrated in vacuo. Column chromatography over silica gel (CH$_2$Cl$_2$-MeOH 4:1) provided the title compound. $^1$H NMR (300 MHz, DMSO-d$_6$) δ 0.96 (t, J=7 Hz, 3H), 1.32 (sextet, J=7 Hz, 2H), 1.53 (quintet, J=7 Hz, 2H), 2.00 (s, 3H), 2.05 (s, 3H), 3.29 (t, J=6 Hz, 4H), 3.55 9t, J=6 Hz, 4H), 3.72 (t, J=7 Hz, 2H), 5.30 (s, 1H); MS (ESI) m/z 297 (M+H).

Example 10

(2Z)-2-(3-butyl-4,5-dimethyl-1,3-thiazol-2(3H)-ylidene)-N-(5-chloro-2-methoxyphenyl)acetamide The title compound was prepared as described in Example 8 by substituting 5-chloro-2-methoxy-phenyl isocyanate for cyclohexyl isocyanate. $^1$H NMR (300 MHz, DMSO-d$_6$) δ 0.95 (t, J=7 Hz, 3H), 1.37 (sextet, J=7 Hz, 2H), 1.58 (quintet, J=7 Hz, 2H), 2.03 (s, 3H), 2.07 (s, 3H), 3.68 (t, J=7 Hz, 2H), 3.85 (s, 3H), 5.69 (s, 1H), 6.87 (d-d, J=9 Hz, 3 Hz, 1H), 6.95 (d, J=9 Hz, 1H), 8.33 (s, 1H), 8.41 (d, J=3 Hz, 1H); MS (ESI) m/z 367 (M+H)$^+$. Anal calcd for C$_{18}$H$_{23}$ClN$_2$O$_2$S: C, 58.92; H, 6.32; N, 7.63. Found: C, 58.75; H, 6.58; N, 7.52.

Example 11

(2Z)-1-(5-chloro-2-methoxyphenyl)-2-(3-propyl-1,3-benzothiazol-2(3H)-ylidene)ethanone The title compound was prepared as described in Example 1B by substituting 2-methyl-3-propylbenzo[d]thiazol-3-ium iodide for Example 1A. $^1$H NMR (300 MHz, DMSO-d$_6$) δ 0.98 (t, J=7 Hz, 3H), 1.79 (sextet, J=7 Hz, 2H), 3.90 (s, 3H), 4.19 (t, J=7 Hz, 2H), 6.72 (s, 1H), 7.16 (d, J=9 Hz, 1H), 7.25 (m, 1H), 7.45 (m, 2H), 7.58 (d, J=8 Hz, 1H), 7.65 (d, J=3 Hz, 1H), 7.83 (d-d, J=8 Hz, 1.5 Hz, 1H); MS (ESI) m/z 360 (M+H)$^+$. Anal calcd for C$_{19}$H$_{18}$ClNO$_2$S: C, 63.41; H, 5.04; N, 3.89. Found: C, 63.09; H, 5.17; N, 3.93.

Example 12

(2Z)-1-(5-chloro-2-methoxyphenyl)-2-1,3-(2,4-difluorobenzyl)-4,5-dimethyl-[3-thiazol-2(3H)-ylidene]ethanone The title compound was prepared as described in Example 1B by substituting 3-(2,4-difluorobenzyl)-2,4,5-trimethylthiazol-3-ium iodide for Example 1A. $^1$H NMR (300 MHz, DMSO-d$_6$) δ 2.18 (s, 3H), 2.21 (s, 3H), 3.67 (s, 3H), 5.12 (s, 2H), 6.44 (s, 1H), 6.94 (m, 1H), 7.04 (d, J=9 Hz, 1H), 7.29 (m, 1H), 7.37 (m, 2H), 7.58 (d, J=1.5 Hz, 1H); MS (ESI) m/z 422 (M+H). Anal calcd for C$_{21}$H$_{18}$F$_2$ClNO$_2$S: C, 59.79; H, 4.30; N, 3.32. Found: C, 59.35; H, 4.14; N, 3.25.

Example 13

(2Z)-2-(5-bromo-3-butyl-4-methyl-1,3-thiazol-2(3H)-ylidene)-1-(5-chloro-2-methoxyphenyl)ethanone The title compound was prepared as described in Example 1B by substituting 5-bromo-3-butyl-2,4-dimethylthiazol-3-ium iodide for Example. $^1$H NMR (300 MHz, DMSO-d$_6$) δ 0.96 (t, J=7 Hz, 3H), 1.39 (sextet, J=7 Hz, 2H), 1.66 (quintet, J=7 Hz, 2H), 2.29 (s, 3H), 3.86 (s, 3H), 3.99 (t, J=7 Hz, 2H), 6.76 (s, 1H), 7.14 (d, J=9 Hz, 1H), 7.44 (d-d, J=9 Hz, 3 Hz, 1H), 7.64 (d, J=3 Hz, 1H); MS (ESI) m/z 416 (M+H)$^+$. Anal calcd for C$_{17}$H$_{19}$BrClNO$_2$S: C, 48.99; H, 4.60; N, 3.36. Found: C, 49.22; H, 4.45; N, 3.33.

Example 14

(2Z)-2-(3-butyl-4-methyl-1,3-thiazol-2(3H)-ylidene)-1-(5-chloro-2-methoxyphenyl)ethanone The title compound was isolated from the chromatographic purification of Example 13. $^1$H NMR (300 MHz, DMSO-d$_6$) δ 0.96 (t, J=7 Hz, 3H), 1.39 (sextet, J=7 Hz, 2H), 1.66 (quintet, J=7 Hz, 2H), 2.28 (d, J=1 Hz, 3H), 3.86 (s, 3H), 3.93 (t, J=7 Hz, 2H), 6.48 (s, 1H), 6.57 (d, J=1 Hz, 1H), 7.12 (d, J=9 Hz, 1H), 7.40 (d-d, J=9 Hz, 3 Hz, 1H), 7.65 (d, J=3 Hz, 1H); MS (ESI) m/z 338 (M+H)$^+$. Anal calcd for C$_{17}$H$_{20}$ClNO$_2$S.0.1H$_2$O: C, 60.11; H, 5.99; N, 4.12. Found: C, 59.95; H, 5.68; N, 3.96.

Example 15

(2Z)-1-(1-adamantyl)-2-(3-ethyl-1,3-benzothiazol-2(3H)-ylidene)ethanone

The title compound was prepared as described in Example 1B by substituting 3-ethyl-2-methylbenzo[d]thiazol-3-ium iodide for Example 1A and 1-adamantanecarbonyl chloride for 5-chloro-2-methoxy-benzoyl chloride. $^1$H NMR (300 MHz, DMSO-d$_6$) δ 1.25 (t, J=7 Hz, 3H), 1.70 (m, 6H), 1.83 (m, 6H), 2.00 (m, 3H), 4.22 (t, J=7 Hz, 2H), 6.19 (s, 1H), 7.18 (m, 1H), 7.40 (m, 2H), 7.71 (d, J=7 Hz, 1H); MS (ESI) m/z 340 (M+H)$^+$. Anal calcd for C$_{21}$H$_{25}$NOS.0.2H$_2$O: C, 73.51; H, 7.46; N, 4.08. Found: C, 73.59; H, 7.29; N, 3.88.

Example 16

(Z)-2-(5-acetyl-3-butyl-4-methylthiazol-2(3H)-ylidene)-1-(5-chloro-2-methoxyphenyl)ethanone To a stirred suspension of NaH (60% in mineral oil, 0.08 g, 2 mmol) in anhydrous DMF (3 mL) at 0° C. was added 5-chloro-2-methoxyacetophenone (0.37 g, 2 mmol) followed by subsequent addition of n-butylisothiocyanate (0.24 mL, 2 mmol) in DMF (3 mL). The mixture was stirred at 0° C. for 2 hours after which 3-chloropentane-2,4-dione (0.23 mL, 2 mmol) was added drop-wise. The mixture was stirred at 0° C. for 2 hours and then heated to 90° C. for 5 hours. The mixture was cooled to ambient temperature, diluted with water (30 mL) and extracted with ethyl acetate (3×35 mL). The combined organic layers were washed sequentially with water, brine, dried with MgSO$_4$, filtered and concentrated in vacuo. The residue was purified by flash chromatography eluting with 50% ethyl acetate in hexane to provide the title compound as a yellow solid. $^1$H NMR (300 MHz, DMSO-d$_6$) δ ppm 0.96 (t, J=7.3 Hz, 3 H), 1.27-1.55 (m, 2 H), 1.58-1.80 (m, 2 H), 2.45 (s, 3 H), 2.65 (s, 3 H), 3.88 (s, 3 H), 3.94-4.10 (m, 2 H), 6.78 (s, 1 H), 7.16 (d, J=8.8 Hz, 1 H), 7.47 (dd, J=8.8, 2.7 Hz, 1 H), 7.65 (d, J=2.7 Hz, 1 H). MS (DCI) m/z 380 (M+H).$^+$ Anal calcd for C$_{19}$H$_{22}$ClNO$_3$S: C, 60.07; H, 5.84; N, 3.69. Found: C, 59.56; H, 5.95; N, 3.68.

Example 17

(Z)-2-(3-butyl-5-((Z)-1-(hydroxyimino)ethyl)-4-methylthiazol-2(3H)-ylidene)-1-(5-chloro-2-methoxyphenyl)ethanone Example 16 (38 mg, 0.1 mmol) in pyridine (2 mL) was treated with NH$_2$OH_HCl (10 mg, 0.15 mmol) and stirred at 50° C. for 14 hours. The mixture was then poured into water and extracted with ethyl acetate (2×15 mL). The organic layers were combined, washed sequentially with water, brine, dried with MgSO$_4$, filtered and concentrated in vacuo. The residue was purified by flash chromatography eluting with ethyl acetate to provide the title compounds as a mixture of E and Z isomers. $^1$H NMR (300 MHz, DMSO-d$_6$), δ ppm 0.97 (t, J=7.3 Hz, 3 H), 1.31-1.51 (m, 2 H), 1.58-1.79 (m, 2 H), 2.07-2.27 (m, 3 H), 2.43 (s, 3 H), 3.79-3.93 (m, 3 H), 3.91-4.07 (m, 2 H), 6.61 (d, J=3.7 Hz, 1 H), 7.13 (d, J=8.8 Hz, 1 H), 7.42 (dd, J=8.8, 2.7 Hz, 1 H), 7.65 (d, J=2.7 Hz, 1 H), 11.11 (s, 0.4 H), 11.33 (s, 0.6 H). MS (DCI) m/z 395 (M+H)$^+$, 379 (M+H-16)$^+$.

Example 19

(2Z)-3-butyl-2-[2-(5-chloro-2-methoxyphenyl)-2-oxoethylidene]-2,3-dihydro-1,3-thiazole-5-carbaldehyde The title compound was prepared as described in Example 16 by substituting 2-bromomalonaldehyde for 3-chloropentane-2-4-dione. $^1$H NMR (300 MHz, DMSO-$d_6$), δ ppm 0.95 (t, J=7.3 Hz, 3 H), 1.23-1.51 (m, 2 H), 1.65-1.90 (m, 2 H), 3.88 (s, 3 H), 4.10 (t, J=7.3 Hz, 2 H), 6.82 (s, 1 H), 7.17 (d, J=8.8 Hz, 1 H), 7.49 (dd, J=8.8, 3.1 Hz, 1 H), 7.64 (d, J=2.7 Hz, 1 H), 8.51 (s, 1 H), 9.77 (s, 1 H). MS (DCI) m/z 352 (M+H).$^+$ Anal calcd for $C_{17}H_{18}ClNO_3S \cdot 0.5H_2O$: C, 56.58; H, 5.31; N, 3.88. Found: C, 56.69; H, 5.11; N, 3.68.

Example 20

(2Z)-3-butyl-2-[2-(5-chloro-2-methoxyphenyl)-2-oxoethylidene]-2,3-dihydro-1,3-thiazole-5-carbaldehyde oxime A mixture of Example 19 (35 mg, 0.1 mmol) and NH$_2$OH_HCl (10 mg, 0.15 mmol) in pyridine (2 mL) was stirred at room temperature for 14 hours. The mixture was poured into water and extracted with ethyl acetate (2×15 mL). The combined organic extracts were washed sequentially with water and brine, dried over MgSO$_4$, Filtered, and concentrated in vacuo. The residue was purified by flash chromatography using ethyl acetate as an eluent to provide the title compounds as a mixture of E and Z isomers. $^1$H NMR (300 MHz, DMSO-$d_6$) δ ppm 0.90 (t, J=7.3 Hz, 3 H), 1.25-1.42 (m, 2 H), 1.73 (m, 2 H), 3.86 (s, 3 H), 4.01 (m, 2 H), 6.58 (s, 0.6 H), 6.64 (s, 0.4 H), 7.04-7.20 (m, 1H), 7.35-7.49 (m, 1 H), 7.57 (s, 1 H), 7.61-7.70 (m, 1 H), 7.88 (s, 0.6 H), 8.19 (s, 0.4H), 11.26 (s, 0.4 H), 11.72 (s, 0.6 H), MS (DCI) m/z 368 (M+H)$^+$, 352 (M+H-16)$^+$.

Example 21

(2Z)-1-(5-chloro-2-methoxyphenyl)-2-[4,5-dimethyl-3-(2-morpholin-4-ylethyl)-1,3-thiazol-2(3H)-ylidene]ethanone The title compound was prepared as described in Example 16 by substituting with 2-(4-morpholino)-ethylisothiocyanate for n-butylisothiocyanate and 3-chloro-2-butanone for 3-chloropentane-2,4-dione. $^1$H NMR (300 MHz, CDCl$_3$) δ ppm 2.19 (s, 3 H), 2.21 (s, 3 H), 2.47-2.59 (m, 4 H), 2.69 (t, 2 H), 3.67-3.77 (m, 4 H), 3.87 (s, 3 H), 3.99 (t, J=13.9 Hz, 2 H), 6.49 (s, 1 H), 6.81-6.91 (m, 1 H), 7.13-7.37 (m, 1 H), 7.86 (d, J=2.7 Hz, 1 H). MS (DCI) m/z 409 (M+H)$^+$ Anal calcd for $C_{20}H_{25}ClN_2O_3S \cdot H_2O$: C, 56.26; H, 6.37; N, 6.56. Found: C, 56.38; H, 6.31; N, 6.18.

Example 23

(2Z)-3-butyl-2-(2-oxo-2-pyridin-2-ylethylidene)-2,3-dihydro-1,3-thiazole-5-carbaldehyde The title compound was prepared as described in Example 16 by substituting 2-acetylpyridine for 5-chloro-2-methoxyacetophenone and 2-bromomalonaldehyde for 3-chloropentane-2,4-dione. $^1$H NMR (300 MHz, CDCl$_3$) δ ppm 1.02 (t, J=7.3 Hz, 3 H), 1.47 (dd, J=15.3, 7.5 Hz, 2 H), 1.81-2.07 (m, 2 H), 4.09 (t, J=7.3 Hz, 2 H), 7.30-7.43 (m, 2 H), 7.60 (s, 1 H), 7.74-7.94 (m, 1 H), 8.23 (d, J=7.8 Hz, 1 H), 8.53-8.77 (m, 1H), 9.80 (s, 1 H). MS (DCI) m/z 289 (M+H)$^+$.

Example 25

(2Z)-3-butyl-2-[2-(3,5-difluorophenyl)-2-oxoethylidene]-2,3-dihydro-1,3-thiazole-5-carbaldehyde The title compound was prepared as described in Example 16 by substituting 3,5-difluoroacetophenone for 5-chloro-2-methoxyacetophenone and 2-bromomalonaldehyde for 3-chloropentane-2,4-dione. $^1$H NMR (300 MHz, CDCl$_3$) δ ppm 0.91-1.14 (m, 3 H), 1.40-1.53 (m, 2 H), 1.78-2.04 (m, 2 H), 3.95-4.13 (m, 2 H), 6.38-6.57 (m, 1 H), 6.83-7.04 (m, 1 H), 7.33-7.49 (m, 2 H), 7.55-7.67 (m, 1 H), 9.73-9.89 (m, 1 H). MS (DCI) m/z 324 (M+H)$^+$ Anal calcd for $C_{16}H_{15}NO_2SF_2$: C, 59.43; H, 4.68; N, 4.33. Found: C, 59.33; H, 4.60; N, 4.32.

Example 26

(2Z)-3-butyl-2-[2-(2-fluorophenyl)-2-oxoethylidene]-2,3-dihydro-1,3-thiazole-5-carbaldehyde The title compound was prepared as described in Example 16 by substituting 2-fluoroacetophenone for 5-chloro-2-methoxyacetophenone and 2-bromomalonaldehyde for 3-chloropentane-2,4-dione. $^1$H NMR (300 MHz, CDCl$_3$) δ ppm 0.85-1.14 (m, 3 H), 1.35-1.53 (m, 2 H), 1.82-2.01 (m, 2 H), 3.85-4.13 (m, 2 H), 6.60-6.77 (m, 1 H), 7.02-7.16 (m, 1 H), 7.17-7.29 (m, 1 H), 7.35-7.47 (m, 1 H), 7.54-7.67 (m, 1 H), 7.91-8.20 (m, 1 H), 9.73-9.89 (m, 1 H).). MS (DCI) m/z 306 (M+H)$^+$. Anal calcd for $C_{16}H_{16}NO_2SF$: C, 62.93; H, 5.28; N, 4.59. Found: C, 62.31; H, 5.03; N, 4.48.

Example 27

(2Z)-3-butyl-2-[2-(2,4-difluorophenyl)-2-oxoethylidene]-2,3-dihydro-1,3-thiazole-5-carbaldehyde The title compound was prepared as described in Example 16 by substituting 2,4-difluoroacetophenone for 5-chloro-2-methoxyacetophenone and 2-bromomalonaldehyde for 3-chloropentane-2,4-dione. $^1$H NMR (300 MHz, CDCl$_3$) δ ppm 1.02 (t, J=7.3 Hz, 3H), 1.31-1.52 (m, 2 H), 1.76-2.01 (m, 2 H), 4.00 (t, J=7.5 Hz, 2 H), 6.63 (s, 1 H), 6.76-6.90 (m, 1 H), 6.90-7.07 (m, 1 H), 7.58 (s, 1 H), 7.98-8.22 (m, 1 H), 9.79 (s, 1 H). MS (DCI) m/z 324 (M+H)$^+$. Anal clad for $C_{16}H_{15}NO_2SF_2$: C, 59.43; H, 4.68; N, 4.33. Found: C, 59.31; H, 4.58; N, 4.12.

Example 28

(2Z)-2-(3-butyl-4,5-dimethyl-1,3-thiazol-2(3H)-ylidene)-1-(2-fluorophenyl)ethanone The title compound was prepared as described in Example 16 by substituting 2-fluoroacetophenone for 5-chloro-2-methoxyacetophenone and 3-chloro-2-butanone for 3-chloropentane-2,4-dione. $^1$H NMR (300 MHz, DMSO-$d_6$) δ ppm 0.94 (t, J=7.3 Hz, 3 H), 1.24-1.45 (m, 2 H), 1.56-1.75 (m, 2 H), 2.17 (s, 3 H), 2.20 (s, 3 H), 3.75-4.09 (m, 2H), 6.34 (s, 1 H), 7.12-7.31 (m, 2 H), 7.33-7.53 (m, 1 H), 7.66-7.90 (m, 1 H). MS (DCI) m/z 306 (M+H).$^+$. Anal calcd for $C_{17}H_{20}FNOS$: C, 66.85; H, 6.60; N, 4.59. Found: C, 66.99; H, 6.83; N, 4.51.

Example 29

(2Z)-2-(3-butyl-4,5-dimethyl-1,3-thiazol-2(3H)-ylidene)-1-pyridin-2-ylethanone

The title compound was prepared as described in Example 16 by substituting 2-acetylpyridine for 5-chloro-2-methoxyacetophenone and 3-chloro-2-butanone for 3-chloropentane-2,4-dione. $^1$H NMR (300 MHz, DMSO-$d_6$) δ ppm 0.95 (t, J=7.3 Hz, 3 H), 1.24-1.48 (m, 2 H), 1.56-1.72 (m, 2 H), 2.09-2.32 (m, J=8.5 Hz, 3 H), 2.18 (s, 3 H), 3.89-4.10 (m, 2 H), 7.07 (s, 1 H), 7.32-7.53 (m, 1 H), 7.81-7.95 (m, 1 H), 7.95-8.09 (m, 1 H), 8.62 (d, J=3.7 Hz, 1 H). MS (DCI) m/z 288 (M+H)$^+$. Anal calcd for $C_{21}H_{24}ClNO_3S$ 0.2$H_2O$: C, 65.81; H, 7.04; N, 9.59. Found: C, 65.93; H, 7.25; N, 9.28

Example 30

(2Z)-2-(3-butyl-4,5-dimethyl-1,3-thiazol-2(3H)-ylidene)-1-(3,5-difluorophenyl)ethanone The title compound was prepared as described in Example 16 by substituting 3,5-difluoroacetophenone for 5-chloro-2-methoxyacetophenone and 3-chloro-2-butanone for 3-chloropentane-2,4-dione. $^1$H NMR (300 MHz, DMSO-$d_6$) δ ppm 0.93 (t, J=7.3 Hz, 3H), 1.39 (dd, J=15.1, 7.3 Hz, 2 H), 1.62 (d, J=6.4 Hz, 2 H), 2.17 (s, 3 H), 2.21 (s, 3 H), 3.89-4.33 (m, 2 H), 6.61 (s, 1 H), 7.18-7.37 (m, 1 H), 7.63 (dd, J=8.8, 2.4 Hz, 2 H). MS (DCI) m/z 324 (M+H).$^+$

Example 31

(2Z)-2-(3-butyl-3,4,5,6-tetrahydro-2H-cyclopenta[d][1,3]thiazol-2-ylidene)-1-(5-chloro-2-methoxyphenyl)ethanone The title compound was prepared as described in Example 16 by replacing 2-chlorocyclopentanone for 3-chloropentane-2,4-dione. $^1$H NMR (300 MHz, DMSO-$d_6$) δ ppm 0.93 (t, J=7.3 Hz, 3 H), 1.34 (dd, J=15.1, 7.6 Hz, 2 H), 1.50-1.82 (m, 2 H), 2.33-2.49 (m, 2 H), 2.74 (q, J=7.0 Hz, 4 H), 3.68-3.94 (m, 5 H), 6.55 (s, 1 H), 7.11 (d, J=8.8 Hz, 1 H), 7.36-7.44 (m, 1 H), 7.65 (d, J=2.7 Hz, 1 H). MS (DCI) m/z 364 (M+H)$^+$. Anal calcd for $C_{19}H_{22}ClNO_2S$: C, 62.71; H, 6.09; N, 3.85. Found: C, 62.33; H, 6.28; N, 3.77.

Example 32

(Z)-2-(5-acetyl-4-methyl-3-((tetrahydrofuran-2-yl)methyl)thiazol-2(3H)-ylidene)-1-(5-chloro-2-methoxyphenyl)ethanone The title compound was prepared as described in Example 16 by substituting tetrahydrofuran-2-(ylmethyl)isothiocyanate for n-butylisothiocyanate. $^1$H NMR (300 MHz, DMSO-$d_6$) δ ppm 1.56-1.76 (m, 1 H), 1.77-1.99 (m, 2 H), 2.01-2.19 (m, 1 H), 2.46 (s, 3 H), 2.64 (s, 3 H), 3.57-3.72 (m, 1 H), 3.74-3.86 (m, 1 H), 3.87 (s, 3 H), 4.08-4.19 (m, 2 H), 4.18-4.33 (m, 1 H), 6.76 (s, 1 H), 7.15 (d, J=8.8 Hz, 1 H), 7.46 (dd, J=8.8, 2.7 Hz, 1 H), 7.62 (d, J=2.7 Hz, 1 H). MS (DCI) m/z 408 (M+H)$^+$. Anal calcd for $C_{21}H_{20}ClNO_3S$: C, 58.89; H, 5.44; N, 3.43. Found: C, 58.61; H, 5.35; N, 3.38.

Example 34

(Z)-2-(5-acetyl-3-butyl-4-methylthiazole-2(3H)-ylidene-1-(pyridine-2-yl)ethanone The title compound was prepared as described in Example 16 by substituting 2-acetylpyridine for 5-chloro-2-methoxyacetophenone. $^1$H NMR (300 MHz, DMSO-$d_6$) δ ppm 0.96 (t, J=7.3 Hz, 3 H), 1.29-1.52 (m, 2 H), 1.58-1.84 (m, 2 H), 2.47 (s, 3 H), 2.66 (s, 3 H), 3.98-4.18 (m, 2 H), 7.29 (s, 1 H), 7.44-7.58 (m, 1 H), 7.96 (td, J=7.6, 1.7 Hz, 1 H), 8.04 (dt, 1 H), 8.67 (d, J=4.1 Hz, 1 H). MS (DCI) m/z 317 (M+H)$^+$. Anal calcd for $C_{21}H_{20}ClNO_3S$: C, 64.53; H, 6.37; N, 8.85. Found: C, 64.46; H, 6.43; N, 8.83.

Example 35

(2Z)-2-(3-butyl-5-tert-butyl-4-methyl-1,3-thiazol-2(3H)-ylidene)-1-(3-chlorothien-2-yl)ethanone

Example 35A 5-tert-butyl-2,4-dimethyl-1,3-thiazole

Dimethyl zinc (2 M in toluene, 60 mL, 120 mmol) was added to a solution of titanium(IV) chloride (13.1 mL, 120 mmol) in dichloroethane (60 mL) at 0° C. and the mixture was stirred for 15 minutes after which a solution of 5-acetyl-2,4-dimethyl thiazole (3.11 g, 20 mmol) in dichloroethane (20 mL) was added dropwise. The mixture was stirred overnight and diluted carefully with saturated ammonium hydroxide at 0° C. (30 mL). The mixture was filtered through silica gel and washed thoroughly with ethyl acetate. The filtrate was concentrated in vacuo to provide the title compound. $^1$H NMR (300 MHz, CDCl$_3$) δ ppm 1.39 (s, 9 H) 2.44 (s, 3 H) 2.57 (s, 3 H); MS (ESI) m/z 170 (M+H)$^+$.

Example 35B 3-butyl-5-tert-butyl-2,4-dimethyl-1,3-thiazol-3-ium iodide

The title compound was prepared as described in Example 1A, substituting Example 35A for 2,5-dimethyl thiadiazole. $^1$H NMR (300 MHz, DMSO-$d_6$) δ ppm 0.91-0.98 (m, 3 H) 1.35-1.46 (m, 11 H) 1.64-1.76 (m, 2 H) 2.59 (s, 3 H) 2.96 (s, 3 H) 4.26-4.34 (m, 2 H); MS (ESI) m/z 229 (M)$^+$.

Example 35C (2Z)-2-(3-butyl-5-tert-butyl-4-methyl-1,3-thiazol-2(3H)-ylidene)-1-(3-chlorothien-2-yl)ethanone To a solution of Example 35B (51 mg, 0.15 mmol) and 4-dimethylamino pyridine (61 mg, 0.5 mmol) in dichloromethane (3 mL) was added 3-chlorothiophene-2-carbonyl chloride (27 mg, 0.15 mmol) and the mixture was stirred overnight. The mixture was washed with water, concentrated in vacuo and the residue was purified by preparative HPLC on a Waters Symmetry C8 column (25 mm×100 mm, 7 μm particle size) using a gradient of 10% to 100% acetonitrile: 0.1% aqueous trifluoroacetic acid over 8 minutes (10 min run time) at a flow rate of 40 mL/min to provide the title compound. $^1$H NMR (300 MHz, DMSO-$d_6$) δ ppm 0.95 (t, J=7.3 Hz, 3 H), 1.32-1.46 (m, 12 H), 1.63-1.73 (m, 2 H), 2.36 (s, 3 H), 3.90-3.97 (m, 2 H), 6.58 (s, 1 H), 7.10 (d, J=5.4 Hz, 1 H), 7.72 (d, J=5.42 Hz, 1 H); MS (DCI/NH$_3$) m/z 370 (M+H)$^+$. Anal. Calcd for $C_{18}H_{24}ClNOS_2.0.1\ C_2HF_3O_2$: C, 57.32; H, 6.37; N, 3.67. Found: C, 57.47; H, 6.37; N, 3.83.

Example 36

(2Z)-2-(3-butyl-5-tert-butyl-4-methyl-1,3-thiazol-2(3H)-ylidene)-1-(2-chloropyridin-3-yl)ethanone The title compound was prepared as described in Example 35C, substituting 2-chloronicotinyl chloride for 3-chlorothiophene carbonyl chloride. $^1$H NMR (300 MHz, DMSO-$d_6$) δ ppm 0.91 (t, J=7.3 Hz, 3 H), 1.32-1.45 (m, 11 H), 1.55-1.67 (m, 2 H), 2.36 (s, 3 H), 3.90-3.97 (m, 2 H), 6.07 (s, 1 H), 7.47 (dd, J=7.8, 4.8 Hz, 1 H), 7.91 (dd, J=7.5, 2.0 Hz, 1 H), 8.40 (dd, J=4.8, 2.0 Hz, 1 H); MS (DCI/NH$_3$) m/z 365 (M+H)$^+$. Anal. Calcd for $C_{19}H_{25}ClN_2S$.0.1 $C_2HF_3O_2$: C, 54.93; H, 5.82; N, 6.30. Found: C, 54.93; H, 5.77; N, 6.30.

Example 37

(2Z)-2-(3-butyl-5-tert-butyl-4-methyl-1,3-thiazol-2(3H)-ylidene)-1-cyclopentylethanone The title compound was prepared as described in Example 35C, substituting cyclopentane carbonyl chloride for 3-chlorothiophene carbonyl chloride. $^1$H NMR (300 MHz, DMSO-$d_6$) δ ppm 0.93 (t, J=7.3 Hz, 3 H), 1.23-1.95 (m, 21 H), 2.27-2.45 (m, 3H), 2.66-2.93 (m, 1 H), 3.86-4.11 (m, 2 H), 5.84 (s, 1 H); MS (DCI/NH$_3$) m/z 322 (M+H)$^+$. Anal. Calcd for $C_{19}H_{31}NOS$.1.2 $C_2HF_3O_2$: C, 55.23; H, 6.93; N, 3.28. Found: C, 55.52; H, 7.28; N, 3.14.

Example 38

(2Z)-2-(3-butyl-5-tert-butyl-4-methyl-1,3-thiazol-2(3H)-ylidene)-1-cyclohexylethanone The title compound was prepared as described in Example 35C, substituting cyclohexane carbonyl chloride for 3-chlorothiophene carbonyl chloride. $^1$H NMR (300 MHz, DMSO-$d_6$) δ ppm 0.88-0.98 (m, 3 H), 1.10-1.49 (m, 15 H), 1.50-1.85 (m, 8 H), 2.21-2.31 (m, 1 H), 2.36 (s, 3 H), 3.99 (s, 2 H), 5.81 (s, 1 H); MS (DCI/NH$_3$) m/z 336 (M+H)$^+$. Anal. Calcd for $C_{20}H_{33}NOS$.1.2 $C_2HF_3O_2$: C, 56.96; H, 7.30; N, 2.97. Found: C, 56.526; H, 7.29; N, 3.04.

Example 39

(2Z)-2-(3-butyl-5-tert-butyl-4-methyl-1,3-thiazol-2(3H)-ylidene)-1-(5-chloro-2-methoxyphenyl)ethanone The title compound was prepared as described in Example 35C, substituting 5-chloro-2-methoxybenzoyl chloride for 3-chlorothiophene carbonyl chloride and the product was purified by flash chromatography (silica gel, 80:20 hexanes:ethyl acetate) to provide the title compound. $^1$H NMR (300 MHz, DMSO-$d_6$) δ ppm 0.96 (t, J=7.3, Hz, 3 H), 1.31-1.46 (m, 11 H), 1.57-1.71 (m, J=7.71, Hz, 2 H), 2.34 (s, 3 H), 3.82-3.93 (m, 5H), 6.47 (s, 1 H), 7.10 (d, J=8.8 Hz, 1 H), 7.39 (dd, J=8.7, 2.9 Hz, 1 H), 7.63 (d, J=2.7 Hz, 1 H); MS (DCI/NH$_3$) m/z 394 (M+H)$^+$. Anal. Calcd for $C_{21}H_{28}ClNO_2$.0.3 H$_2$O: C, 63.16; H, 7.22; N, 3.46. Found: C, 63.29; H, 7.00; N, 3.46.

Example 40

6-[(2Z)-2-(3-butyl-5-tert-butyl-4-methyl-1,3-thiazol-2(3H)-ylidene)ethanoyl]-2,2-dimethyl-2,3-dihydro-4H-pyran-4-one The title compound was prepared and purified as described in Example 35C, substituting 2,2-dimethyl-4-oxo-3,4-dihydro-2H-pyran-6-carbonyl chloride for 3-chlorothiophene carbonyl chloride. $^1$H NMR (300 MHz, DMSO-$d_6$) δ ppm 0.99 (t, J=7.3 Hz, 3 H), 1.35-1.47 (m, 17 H), 1.56-1.69 (m, 2 H), 2.38 (s, 3 H), 2.53 (s, 2 H), 3.90-4.03 (m, 2 H), 5.88 (s, 1 H), 6.33 (s, 1 H); MS (DCI/NH$_3$) m/z 378 (M+H)$^+$. Anal. Calcd for $C_{19}H_{31}NOS$.0.2 $C_2HF_3O_2$.0.2 $CH_2Cl_2$: C, 62.16; H, 7.63; N, 3.36. Found: C, 62.31; H, 7.58; N, 3.51.

Example 41

(2Z)-1-(1-benzofuran-5-yl)-2-(3-butyl-5-tert-butyl-4-methyl-1,3-thiazol-2(3H)-ylidene)ethanone The title compound was prepared and purified as described in Example 35C, substituting benzofuran-5-carbonyl chloride for 3-chlorothiophene carbonyl chloride. $^1$H NMR (300 MHz, DMSO-$d_6$) δ ppm 0.96 (t, J=7.3 Hz, 3 H), 1.30-1.78 (m, 13 H), 2.35 (s, 3 H), 3.97-4.12 (m, 2 H), 6.53 (s, 1 H), 7.00-7.06 (m, J=2.4 Hz, 1 H), 7.61 (d, J=8.5 Hz, 1 H), 7.88-7.95 (m, 1 H), 8.01-8.06 (m, J=2.0 Hz, 1 H), 8.22 (d, J=1.4 Hz, 1H); MS (DCI/NH$_3$) m/z 370 (M+H)$^+$. Anal. Calcd for $C_{22}H_{27}NO_2S$.110 $C_2HF_3O_2$.0.2 $CH_2Cl_2$: C, 57.34; H, 5.66; N, 2.75. Found: C, 57.20; H, 6.01; N, 3.06.

Example 42

(2Z)-2-(3-butyl-5-tert-butyl-4-methyl-1,3-thiazol-2(3H)-ylidene)-1-(2,2-dimethyltetrahydro-2H-pyran-4-yl)ethanone The title compound was prepared and purified as described in Example 35C, substituting 2,2-dimethyltetrahydro-2H-pyran-4-carbonyl chloride for 3-chlorothiophene carbonyl chloride. $^1$H NMR (300 MHz, DMSO-$d_6$) δ ppm 0.93 (t, J=7.3 Hz, 3 H), 1.14 (s, 3 H), 1.18 (s, 3 H), 1.30-1.46 (m, 13 H), 1.51-1.65 (m, 4 H), 2.36 (s, 3 H), 2.63-2.78 (m, 1 H), 3.49-3.71 (m, 2 H), 3.99 (s, 2 H), 5.83 (s, 1 H); MS (DCI/NH$_3$) m/z 366 (M+H)$^+$. Anal. Calcd for $C_{21}H_{35}NO_2S$.1.0 $C_2HF_3O_2$.0.9 $CH_2Cl_2$: C, 51.63; H, 6.85; N, 2.52. Found: C, 51.91; H, 6.75; N, 2.70.

Example 43

(2Z)-2-(3-butyl-5-tert-butyl-4-methyl-1,3-thiazol-2(3H)-ylidene)-1-(5-fluoro-2-methoxyphenyl)ethanone The title compound was prepared and purified as described in Example 35C, substituting 5-fluoro-2-methoxybenzoyl chloride for 3-chlorothiophene carbonyl chloride. $^1$H NMR (300 MHz, DMSO-$d_6$) δ ppm 0.96 (t, J=7.3 Hz, 3 H), 1.32-1.48 (m, 11 H), 1.58-1.73 (m, 2 H), 2.37 (s, 3 H), 3.83 (s, 3 H), 3.90-3.98 (m, 2 H), 6.51 (s, 1H), 7.05-7.14 (m, 1 H), 7.16-7.26 (m, 1 H), 7.39-7.46 (m, J=9.5, 3.4 Hz, 1 H); MS (DCI/NH$_3$) m/z 378 (M+H)$^+$. Anal. Calcd for $C_{21}H_{35}FNO_2S$.1.0 $C_2HF_3O_2$.0.2 $CH_2Cl_2$: C, 54.83; H, 5.80; N, 2.75. Found: C, 54.98; H, 5.92; N, 3.04.

Example 44

(2Z)-2-(3-butyl-4-phenyl-1,3-thiazol-2(3H)-ylidene)-1-(5-chloro-2-methoxyphenyl)ethanone The title compound was prepared and purified as described in Example 16, substituting 2-bromoacetophenone for 3-chloropentane-2,4-dione. $^1$H NMR (300 MHz, DMSO-$d_6$) δ ppm 0.73 (t, J=7.3 Hz, 3 H), 1.07-1.19 (m, 2 H), 1.56-1.67 (m, 2 H), 3.82-3.89 (m, 5 H), 6.66 (d, J=1.4 Hz, 1 H), 6.79 (s, 1 H), 7.14 (d, J=9.2 Hz, 1 H), 7.43 (dd, J=8.8, 3.1 Hz, 1 H), 7.46-7.56 (m, 5 H), 7.68 (d, J=2.7 Hz, 1 H); MS (DCI/NH$_3$)

m/z 400(M+H)$^+$. Anal. Calcd for $C_{22}H_{22}ClNO_2S \cdot 0.1$ $C_2HF_3O_2$: C, 64.82; H, 5.42; N, 3.41. Found: C, 64.55; H, 5.48; N, 3.44.

Example 45 ethyl (2Z)-3-butyl-2-[2-(5-chloro-2-methoxyphenyl)-2-oxoethylidene]-2,3-dihydro-1,3-thiazole-4-carboxylate The title compound was prepared and purified as described in Example 16, substituting ethyl 2-bromopyruvate for 3-chloropentane-2,4-dione. $^1$H NMR (300 MHz, DMSO-d$_6$) δ ppm 0.92-0.98 (m, 3 H), 1.35 (td, J=14.8, 7.3 Hz, 5 H), 1.67-1.79 (m, 2H), 3.87 (s, 3 H), 4.31 (q, J=7.12 Hz, 4 H), 6.69 (s, 1 H), 7.15 (d, J=8.8 Hz, 1 H), 7.45 (dd, J=8.8, 2.71 Hz, 1 H), 7.66 (d, J=3.1 Hz, 1 H), 7.78 (s, 1 H); MS (DCI/NH$_3$) m/z 400(M+H)$^+$. Anal. Calcd for $C_{19}H_{22}ClNO_4S$: C, 57.64; H, 5.60; N, 3.56. Found: C, 57.34; H, 5.61; N, 3.44.

Example 46

(2Z)-2-(3-butyl-4-tert-butyl-1,3-thiazol-2(3H)-ylidene)-1-(5-chloro-2-methoxyphenyl)ethanone The title compound was prepared and purified as described in Example 16, substituting 1-bromopinacolone for 3-chloropentane-2,4-dione. $^1$H NMR (300 MHz, DMSO-d$_6$) δ ppm 0.96-1.03 (m, 3 H), 1.35-1.42 (m, 9 H), 1.42-1.54 (m, 2 H), 1.68-1.82 (m, 2 H), 3.87 (s, 3 H), 4.03-4.15 (m, 2 H), 6.54 (d, J=14.9 Hz, 2 H), 7.13 (d, J=8.8 Hz, 1 H), 7.41 (dd, J=8.7, 2.9 Hz, 1 H), 7.66 (d, J=2.7 Hz, 1 H); MS (DCI/NH$_3$) m/z 380 (M+H)$^+$. Anal. Calcd for $C_{20}H_{26}ClNO_2S \cdot 0.2$ $C_2HF_3O_2$: C, 60.84; H, 6.56; N, 3.69. Found: C, 61.18; H, 6.78; N, 3.62.

Example 47

(2Z)-2-(3-butyl-5-methyl-1,3,4-thiadiazol-2(3H)-ylidene)-1-(5-chloro-2-methoxyphenyl)ethanone

Example 47A 3-butyl-2,5-dimethyl-1,3,4-thiadiazol-3-ium iodide

A mixture of 2,5-dimethyl thiadiazole (570 mg, 5 mmol) and 1-iodobutane (2.27 mL, 20 mmol) in acetonitrile (8 mL) was heated at 90° C. for 4 days. The mixture was concentrated to give the title compound which was used without further purification. $^1$H NMR (300 MHz, DMSO-d$_6$) δ ppm 0.91 (q, J=6.9 Hz, 3 H) 1.36 (dd, J=15.3, 7.5 Hz, 2H) 1.82-1.92 (m, 2 H) 2.82 (s, 3 H) 3.06 (s, 3 H) 4.49 (t, J=7.5 Hz, 2 H); MS (DCI/NH$_3$) m/z 184 (M+H)$^+$.

Example 47B (2Z)-2-(3-butyl-5-methyl-1,3,4-thiadiazol-2(3H)-ylidene)-1-(5-chloro-2-methoxyphenyl)ethanone A solution of the product from Example 47A (298 mg, 1 mmol), 5-chloro-2-methoxy benzoic acid, 1-(3-dimethylaminopropyl)-3-ethylcarbodiimide hydrochloride (280 mg, 1.4 mmol) and 4-dimethylamino pyridine (121 mg, 1 mmol) in dichloromethane (4 mL) was stirred overnight. The solution was diluted with water (10 mL) and extracted with dichloromethane (3×5 mL). The organic layers were combined, washed with brine, dried with sodium sulfate and concentrated in vacuo. The residue was purified by preparative HPLC on a Waters Symmetry C8 column (25 mm×100 mm, 7 μm particle size) using a gradient of 10% to 100% acetonitrile:0.1% aqueous trifluoroacetic acid over 8 minutes (10 minutes run time) at a flow rate of 40 mL/minute to provide the title compound. $^1$H NMR (300 MHz, DMSO-d$_6$) δ ppm 0.92 (t, J=7.3 Hz, 3 H), 1.33 (m, J=14.9, 7.4 Hz, 2 H), 1.75 (dq, J=7.5, 7.2 Hz, 2 H), 2.47 (s, 3 H), 3.86 (s, 3 H), 4.12 (t, J=7.1 Hz, 2 H), 6.56 (s, 1 H), 7.14 (d, J=8.8 Hz, 1 H), 7.45 (dd, J=8.8, 3.1 Hz, 1 H), 7.62 (d, J=2.7 Hz, 1 H); MS (DCI/NH$_3$) m/z 339 (M+H)$^+$.

Example 48

(2Z)-2-(3-butyl-5-methyl-1,3,4-thiadiazol-2(3H)-ylidene)-N-(5-chloro-2-methoxyphenyl)acetamide A solution of the product from Example 47A (149 mg, 0.5 mmol), DBU (105 μL, 0.75 mmol) and 5-chloro-2-methoxy phenyl isocyanate (91 mg, 0.5 mmol) was stirred overnight. The solution was diluted with water (10 mL), extracted with dichloromethane (3×5 mL). The organic layers were combined, washed with brine, dried with sodium sulfate and concentrated in vacuo. The residue was purified by the HPLC procedure specified in Example 47B to obtain the title compound. $^1$H NMR (300 MHz, DMSO-d$_6$) δ ppm 0.93 (t, J=7.5 Hz, 3 H), 1.27-1.39 (m, 2 H), 1.64-1.75 (m, 2 H), 2.36 (s, 3 H), 3.82-3.91 (m, 5 H), 5.81 (s, 1 H), 6.92-7.01 (m, 2 H), 8.36 (d, J=2.4 Hz, 1 H), 8.68 (s, 1 H); MS (ESI) m/z 354 (M+H)$^+$. Anal. Calcd for $C_{16}H_{20}ClN_3O_2S \cdot 0.5$ $C_2HF_3O_2$: C, 48.92; H, 4.92; N, 9.99. Found: C, 49.28; H, 5.09; N, 10.07.

Example 49

2-(3-butyl-5-methyl-1,3,4-thiadiazol-2(3H)-ylidene)-N,N'-bis(5-chloro-2,4-dimethoxyphenyl)malonamide A solution of the product from Example 47A (116 mg, 0.4 mmol), DBU (130 μL, 0.88 mmol) and 5-chloro-2,4-dimethoxy phenyl isocyanate (170 mg, 0.8 mmol) was stirred overnight. The residue was purified by flash chromatography (silica gel, 80:20 hexanes:ethyl acetate) to obtain the title compound. $^1$H NMR (300 MHz, DMSO-d$_6$) δ ppm 0.74 (t, J=7.3 Hz, 2 H), 1.02-1.14 (m, 1 H), 1.38-1.49 (m, 1 H), 2.44 (s, 2 H), 3.67 (t, J=7.1 Hz, 2 H), 3.80 (s, 2 H), 3.84-3.89 (m, 3 H), 3.96 (d, J=1.7 Hz, 5 H), 4.60 (s, 1 H), 6.91 (d, J=11.5 Hz, 2 H), 7.37 (s, 1 H), 8.11 (s, 1 H), 11.99 (s, 1 H); MS (DCI/NH$_3$) m/z 597 (M+H)$^+$. Anal. Calcd for $C_{26}H_{30}Cl_2N_4O_6S$: C, 52.26; H, 9.06; N, 5.38. Found: C, 52.10; H, 5.06; N, 938.

Example 50

(2Z)-2-(3-butyl-5-tert-butyl-1,3,4-thiadiazol-2(3H)-ylidene)-1-(5-chloro-2-methoxyphenyl)ethanone

Example 50A

N'-acetyl-2,2-dimethylpropanohydrazide

To a mixture of 2,2-dimethyl-propionic acid hydrazide (2.32 g, 20 mmol), sodium bicarbonate (1.68 g, 20 mmol) in tetrahydrofuran and water (1:1, 40 mL) was added acetyl chloride (1.56 g, 20 mmol) dropwise. The mixture was stirred overnight and concentrated in vacuo. The residue was extracted with dichloromethane and isopropyl alcohol (10:1) (3×10 mL). The organic extracts were combined, dried over MgSO$_4$ and concentrated to give a white solid. The solid was recrystallized from tetrahydrofuran and hexane (1:8) to provide the title compound. $^1$H NMR (300 MHz, DMSO-d$_6$) δ ppm 1.11-1.14 (m, 9 H) 1.83 (s, 3 H) 9.28 (br s, 1 H) 9.53 (br s, 1 H); MS (ESI) m/z 159 (M+H)$^+$.

Example 50B 2-tert-butyl-5-methyl-1,3,4-thiadiazole

A mixture of the product from Example 50A (158 mg, 1 mmol) and Lawesson's reagent (808 mg, 2 mmol) in tetrahydrofuran (4 mL) was heated at reflux for 2 hours. The solution was concentrated, dissolved in dichloromethane (15 mL) and washed with saturated sodium bicarbonate solution (10 mL). The resulting organic layer was passed through a silica pad and washed with dichloromethane and ethyl acetate (10:1). The solvent was evaporated to provide the title compound. $^1$H NMR (300 MHz, DMSO-d$_6$) δ ppm 1.39 (s, 9 H) 2.67 (s, 3 H); MS (ESI) m/z 157 (M+H)$^+$.

Example 50C 3-butyl-5-tert-butyl-2-methyl-1,3,4-thiadiazol-3-ium iodide

The procedure in Example 47A was followed, substituting the product from Example 50B for 2,5-dimethyl thiadiazole. The product was obtained as a brownish liquid in 90% yield and was used without further purification. $^1$H NMR (300 MHz, DMSO-d$_6$) δ ppm 0.93 (t, J=7.3 Hz, 3 H) 1.33-1.48 (m, 11 H) 1.83-1.95 (m, 2 H) 3.07 (s, 3 H) 4.51 (t, J=7.3 Hz, 2 H); MS (ESI) m/z 213 (M+H)$^+$.

Example 50D (2Z)-2-(3-butyl-5-tert-butyl-1,3,4-thiadiazol-2(3H)-ylidene)-1-(5-chloro-2-methoxyphenyl)ethanone The procedure in Example 47B was followed, substituting the product from Example 50C for the product from Example 47A to afford the title compound. $^1$H NMR (300 MHz, DMSO-d$_6$) δ ppm 0.92 (t, J=7.5 Hz, 3 H), 1.27-1.43 (m, 11 H), 1.69-1.80 (m, 2 H), 3.85 (s, 3 H), 4.13 (t, J=7.12 Hz, 2 H), 6.54 (s, 1 H), 7.14 (d, J=8.8 Hz, 1 H), 7.45 (dd, J=8.8, 2.7 Hz, 1 H), 7.60 (d, J=3.1 Hz, 1 H); MS (DCI/NH$_3$) m/z 381 (M+H)$^+$.

Example 51

(2Z)-2-(3-butyl-5-tert-butyl-1,3,4-thiadiazol-2(3H)-ylidene)-N-(5-chloro-2-methoxyphenyl)acetamide The title compound was prepared and purified as described in Example 48 substituting the product from Example 50C for the product from Example 47A. $^1$H NMR (300 MHz, DMSO-d$_6$): δ ppm 0.93 (t, J=7.3 Hz, 3 H), 1.27-1.37 (m, 12 H), 1.64-1.75 (m, 2 H), 3.85 (s, 3 H), 3.89 (t, J=7.1 Hz, 2 H), 6.92-7.01 (m, 2 H), 8.39 (d, J=2.4 Hz, 1 H), 8.68 (s, 1 H); MS (DCI/NH$_3$) m/z 396 (M+H)$^+$. Anal. Calcd for C$_{19}$H$_{26}$ClN$_3$O$_2$S.0.1 C$_2$HF$_3$O$_2$: C, 48.17; H, 5.14; N, 4.60. Found: C, 48.03; H, 4.91; N, 4.96.

Example 52

(2Z)-2-(3-butyl-5-tert-butyl-4-methyl-1,3-thiazol-2(3H)-ylidene)-N-(5-chloro-2-methoxyphenyl)acetamide The title compound was prepared and purified as described in Example 48, substituting Example 35B for Example 47A.

$^1$H NMR (300 MHz, DMSO-d$_6$) δ ppm 0.94 (t, J=7.29 Hz, 3 H), 1.37-1.50 (m, 11 H), 1.62-1.77 (m, 2 H), 2.63 (s, 3 H), 3.89 (s, 3H), 4.26-4.38 (m, 2 H), 4.79 (s, 1 H), 7.11-7.23 (m, 2 H), 8.10 (d, J=2.71 Hz, 1 H), 10.05 (s, 1 H); MS (ESI) m/z 409 (M+H)$^+$. Anal. Calcd for C$_{21}$H$_{29}$ClN$_2$O$_2$S.1.6 C$_2$HF$_3$O$_2$.0.2 CH$_2$Cl$_2$: C, 48.92; H, 4.92; N, 9.99. Found: C, 49.28; H, 5.09; N, 10.07.

Example 53

(2Z)-2-(3-butyl-4-methyl-1,3-thiazol-2(3H)-ylidene)-1-[2-(trifluoromethyl)phenyl]ethanone In a 20 mL vial a solution of 3-butyl-2,4-dimethylthiazol-3-ium iodide (47.92 mg, 0.16 mmol) dissolved in CH$_2$Cl$_2$ (0.5 mL) was added, followed by the addition of DMAP (49.24 mg, 0.40 mmol) dissolved in CH$_2$Cl$_2$ (0.8 mL). Then, to the solution was added 2-(trifluoromethyl)benzoyl chloride (33.4 mg, 0.16 mmol) dissolved in CH$_2$Cl$_2$ (0.5 mL). The vial was capped and shaken overnight at room temperature. The residue was dissolved in 1:1 DMSO/MeOH and purified by reverse phase HPLC using a Waters Sunfire C8 column (30× 75 mm) eluting with a gradient of acetonitrile and 0.1% trifluoroacetic acid in water at a flow rate of 50 mL/min. Fractions selected by mass spectrometry to provide the title compound. $^1$H NMR (500 MHz, DMSO-D$_6$/D$_2$O) δ ppm 0.90 (t, 3 H) 1.27-1.38 (m, 2 H) 1.57-1.67 (m, 2 H) 2.27-2.32 (m, 3 H) 3.90-3.97 (m, 2 H) 5.99-6.02 (m, 1 H) 6.56-6.60 (m, 1 H) 7.53-7.62 (m, 2 H) 7.66-7.77 (m, 2 H); MS (ESI) positive ion 342 (M+H).

Example 54

(2Z)-2-(3-butyl-4-methyl-1,3-thiazol-2(3H)-ylidene)-1-[3-(trifluoromethyl)phenyl]ethanone In a 20 mL vial a solution of 3-butyl-2,4-dimethylthiazol-3-ium iodide (47.92 mg, 0.16 mmol) dissolved in CH$_2$Cl$_2$ (0.5 mL) was added, followed by the addition of DMAP (49.24 mg, 0.40 mmol) dissolved in CH$_2$Cl$_2$ (0.8 mL). Then, to the solution was added 3-(trifluoromethyl)benzoyl chloride (33.4 mg, 0.16 mmol) dissolved in CH$_2$Cl$_2$ (0.5 mL). The vial was capped and shaken overnight at room temperature. The residue was dissolved in 1:1 DMSO/MeOH and purified by reverse phase HPLC using a method analogous to that described in Example 53 to provide the title compound. $^1$H NMR, MS and LC/MS. $^1$H NMR (500 MHz, DMSO-D$_6$/D$_2$O) δ ppm 0.91-0.98 (m, 3 H) 1.34-1.47 (m, 2 H) 1.61-1.72 (m, 2 H) 2.30-2.33 (m, 3 H) 4.07-4.16 (m, 2 H) 6.56-6.60 (m, 1 H) 6.66-6.72 (m, 1 H) 7.69 (t, 1 H) 7.80 (d, 1 H) 8.17-8.23 (m, 1 H) 8.27 (d, 1H); MS (ESI) positive ion 342 (M+H).

Example 55

(2Z)-2-(3-butyl-4-methyl-1,3-thiazol-2(3H)-ylidene)-1-cyclohexylethanone

In a 20 mL vial a solution of 3-butyl-2,4-dimethylthiazol-3-ium iodide (47.92 mg, 0.16 mmol) dissolved in CH$_2$Cl$_2$ (0.5 mL) was added, followed by the addition of DMAP (49.24 mg, 0.40 mmol) dissolved in CH$_2$Cl$_2$ (0.8 mL). Then, to the solution was added cyclohexanecarbonyl chloride (23.5 mg, 0.16 mmol) dissolved in CH$_2$Cl$_2$ (0.5 mL). The vial was capped and shaken overnight at room temperature. The residue was dissolved in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.92 (t, 3 H) 1.09-1.44 (m, 7 H) 1.51-1.70 (m, 3 H) 1.69-1.88 (m, 4 H) 2.21-2.36 (m, 4 H) 3.95-4.01 (m, 2 H) 5.79-5.91 (m, 1 H) 6.57-6.73 (m, 1 H) MS (ESI) positive ion 280 (M+H).

Example 56

(2Z)-2-(3-butyl-4-methyl-1,3-thiazol-2(3H)-ylidene)-1-(3-chloro-1-benzothien-2-yl)ethanone In a 20 mL vial a solution of 3-butyl-2,4-dimethylthiazol-3-ium iodide (47.92 mg, 0.16 mmol) dissolved in CH$_2$Cl$_2$ (0.5 mL) was added, followed by the addition of DMAP (49.24 mg, 0.40 mmol) dissolved in CH$_2$Cl$_2$ (0.8 mL). Then, to the solution was added 3-chlorobenzo[b]thiophene-2-carbonyl chloride (37.0 mg, 0.16 mmol) dissolved in CH$_2$Cl$_2$ (0.5 mL). The vial was capped and shaken overnight at room temperature. The residue was dissolved in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.98 (t, 3 H) 1.39-1.48 (m, 2 H) 1.70-1.80 (m, 2 H) 2.31-2.37 (m, 3 H) 4.00-4.09 (m, 2 H) 6.67-6.70 (m, 1 H) 6.85-6.89 (m, 1 H) 7.49-7.56 (m, 2 H) 7.85-7.92 (m, 1 H) 8.01-8.07 (m, 1 H); MS (ESI) positive ion 364 (M+H).

Example 57

(2Z)-1-(1-adamantyl)-2-(3-butyl-4-methyl-1,3-thiazol-2(3H)-ylidene)ethanone

In a 20 mL vial a solution of 3-butyl-2,4-dimethylthiazol-3-ium iodide (47.92 mg, 0.16 mmol) dissolved in CH$_2$Cl$_2$ (0.5 mL) was added, followed by the addition of DMAP (49.24 mg, 0.40 mmol) dissolved in CH$_2$Cl$_2$ (0.8 mL). Then, to the solution was added 1-adamantyl carbonylchloride (31.8 mg, 0.16 mmol) dissolved in CH$_2$Cl$_2$ (0.5 mL). The vial was capped and shaken overnight at room temperature. The residue was dissolved in 1:1 DMSO/MeOH and purified by reverse phase HPLC using a method analogous to that described in Example 53 to provide the title compound. $^1$H NMR, MS and LC/MS. MS (ESI) positive ion 332 (M+H).

Example 58

(2Z)-2-(3-butyl-4-methyl-1,3-thiazol-2(3H)-ylidene)-1-[5-fluoro-2-(trifluoromethyl)phenyl]ethanone In a 20 mL vial a solution of 3-butyl-2,4-dimethylthiazol-3-ium iodide (47.92 mg, 0.16 mmol) dissolved in CH$_2$Cl$_2$ (0.5 mL) was added, followed by the addition of DMAP (49.24 mg, 0.40 mmol) dissolved in CH$_2$Cl$_2$ (0.8 mL). Then, to the solution was added 5-fluoro-2-(trifluoromethyl)benzoyl chloride (36.2 mg, 0.16 mmol) dissolved in CH$_2$Cl$_2$ (0.5 mL). The vial was capped and shaken overnight at room temperature. The residue was dissolved in 1:1 DMSO/MeOH and purified by reverse phase HPLC using a method analogous to that described in Example 53 to provide the title compound. $^1$H NMR, MS and LC/MS. $^1$H NMR (500 MHz, DMSO-d$_6$/D$_2$O) δ ppm 0.90 (t, 3 H) 1.29-1.38 (m, 2H) 1.56-1.69 (m, 2 H) 2.28-2.32 (m, 3 H) 3.91-4.00 (m, 2 H) 6.00-6.05 (m, 1 H) 6.58-6.62 (m, 1 H) 7.37-7.45 (m, 2 H) 7.77-7.86 (m, 1 H); MS (ESI) positive ion 360 (M+H).

Example 59

(2Z)-2-(3-butyl-4-methyl-1,3-thiazol-2(3H)-ylidene)-1-(5-fluoro-2-methylphenyl)ethanone In a 20 mL vial a solution of 3-butyl-2,4-dimethylthiazol-3-ium iodide (47.92 mg, 0.16 mmol) dissolved in CH$_2$Cl$_2$ (0.5 mL) was added, followed by the addition of DMAP (49.24 mg, 0.40 mmol) dissolved in CH$_2$Cl$_2$ (0.8 mL). Then, to the solution was added 5-fluoro-2-methylbenzoyl chloride (27.6 mg, 0.16 mmol) dissolved in CH$_2$Cl$_2$ (0.5 mL). The vial was capped and shaken overnight at room temperature. The residue was dissolved in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.92 (t, 3 H) 1.28-1.41 (m, 2 H) 1.57-1.68 (m, 2 H) 2.28-2.31 (m, 3 H) 2.33-2.36 (m, 3 H) 3.92-4.03 (m, 2 H) 6.09-6.15 (m, 1 H) 6.54-6.59 (m, 1 H) 7.05-7.14 (m, 1 H) 7.19-7.27 (m, 2 H);); MS (ESI) positive ion 306 (M+H).

Example 60

(2Z)-2-(3-butyl-4-methyl-1,3-thiazol-2(3H)-ylidene)-1-(5-chloro-2-fluorophenyl)ethanone In a 20 mL vial a solution of 3-butyl-2,4-dimethylthiazol-3-ium iodide (47.92 mg, 0.16 mmol) dissolved in CH$_2$Cl$_2$ (0.5 mL) was added, followed by the addition of DMAP (49.24 mg, 0.40 mmol) dissolved in CH$_2$Cl$_2$ (0.8 mL). Then, to the solution was added 5-chloro-2-fluorobenzoyl chloride (30.9 mg, 0.16 mmol) dissolved in CH$_2$Cl$_2$ (0.5 mL). The vial was capped and shaken overnight at room temperature. The residue was dissolved in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.95 (t, 3 H) 1.31-1.41 (m, 2 H) 1.57-1.77 (m, 2 H) 2.28-2.34 (m, 3 H) 3.95-4.02 (m, 2 H) 6.37-6.41 (m, 1 H) 6.55-6.68 (m, 1 H) 7.28-7.35 (m, 1 H) 7.48-7.54 (m, 1 H) 7.76-7.80 (m, 1 H); MS (ESI) positive ion 326 (M+H).

Example 61

(1Z)-1-(3-butyl-5-methyl-1,3,4-thiadiazol-2(3H)-ylidene)-3-cyclopentylacetone

In a 20 mL vial 2-cyclopentylacetic acid (0.9 mL of 0.2 M in DMA, 1.10 equiv) was added followed by the addition of HATU (77 mg in 0.7 mL of DMA, 0.2 mmol, 1.20 equiv.), DIEA (53 mg in 0.7 mL of DMA, 0.4 mmol, 2.40 equiv.), and finally 3-butyl-2,5-dimethyl-1,3,4-thiadiazol-3-ium iodide (50 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.89 (t, 3 H) 1.06-1.16 (m, 2 H) 1.24-1.34 (m, 2 H) 1.43-1.54 (m, 2 H) 1.53-1.61 (m, 2 H) 1.63-1.73 (m, 4 H) 2.14-2.23 (m, 1 H) 2.30-2.34 (m, 2 H) 2.39-2.43 (m, 3 H) 4.03 (t, 2 H) 5.90 (s, 1 H); MS (ESI) m/z 281 (M+H)$^+$.

Example 62

(2Z)-2-(3-butyl-5-methyl-1,3,4-thiadiazol-2(3H)-ylidene)-1-cyclohexylethanone

In a 20 mL vial cyclohexanecarboxylic acid (0.9 mL of 0.2 M in DMA, 1.10 equiv) was added followed by the addition of HATU (77 mg in 0.7 mL of DMA, 0.2 mmol, 1.20 equiv.), DIEA (53 mg in 0.7 mL of DMA, 0.4 mmol, 2.40 equiv.), and finally 3-butyl-2,5-dimethyl-1,3,4-thiadiazol-3-ium iodide (50 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2O$) δ ppm 0.87-0.92 (m, 3 H) 1.10-1.39 (m, 8 H) 1.58-1.76 (m, 8 H) 2.23-2.31 (m, 1 H) 2.38-2.41 (s, 3 H) 4.04 (t, 2 H) 5.90 (s, 1 H); MS (ESI) m/z 281 (M+H)$^+$.

Example 63

(3Z)-1-[bicyclo[2.2.1]hept-2-yl]-3-(3-butyl-5-methyl-1,3,4-thiadiazol-2(3H)-ylidene)acetone In a 20 mL vial 2-(bicyclo[2.2.1]heptan-2-yl)acetic acid (0.9 mL of 0.2 M in DMA, 1.10 equiv) was added followed by the addition of HATU (77 mg in 0.7 mL of DMA, 0.2 mmol, 1.20 equiv.), DIEA (53 mg in 0.7 mL of DMA, 0.4 mmol, 2.40 equiv.), and finally 3-butyl-2,5-dimethyl-1,3,4-thiadiazol-3-ium iodide (50 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2O$) δ ppm 0.90 (t, 3H) 0.98-1.18 (m, 4 H) 1.23-1.49 (m, 6 H) 1.62-1.73 (m, 2 H) 1.80-1.88 (m, 1 H) 1.89-1.95 (m, 1 H) 2.11-2.19 (m, 2 H) 2.23-2.31 (m, 1 H) 2.38-2.43 (m, 3 H) 4.02 (t, 2 H) 5.86-5.92 (m, 1 H); MS (ESI) m/z 307 (M+H)$^+$.

Example 64

(1Z)-1-(3-butyl-5-methyl-1,3,4-thiadiazol-2(3H)-ylidene)-3-(2-chlorophenyl)acetone In a 20 mL vial 2-(2-chlorophenyl)acetic acid (0.9 mL of 0.2 M in DMA, 1.10 equiv) was added followed by the addition of HATU (77 mg in 0.7 mL of DMA, 0.2 mmol, 1.20 equiv.), DIEA (53 mg in 0.7 mL of DMA, 0.4 mmol, 2.40 equiv.), and finally 3-butyl-2,5-dimethyl-1,3,4-thiadiazol-3-ium iodide (50 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2O$) δ ppm 0.79-0.88 (m, 3 H) 1.19-1.28 (m, 2 H) 1.57-1.69 (m, 2 H) 2.40 (s, 3 H) 3.76-3.81 (m, 2 H) 3.96 (t, 2 H) 5.77-5.85 (m, 1 H) 7.22-7.33 (m, 2 H) 7.34-7.40 (m, 1 H) 7.40-7.47 (m, 1 H); MS (ESI) m/z 323 (M+H)$^+$.

Example 65

(2Z)-2-(3-butyl-5-methyl-1,3,4-thiadiazol-2(3H)-ylidene)-1-(3-methylthien-2-yl)ethanone In a 20 mL vial 3-methylthiophene-2-carboxylic acid (0.9 mL of 0.2 M in DMA, 1.10 equiv) was added followed by the addition of HATU (77 mg in 0.7 mL of DMA, 0.2 mmol, 1.20 equiv.), DIEA (53 mg in 0.7 mL of DMA, 0.4 mmol, 2.40 equiv.), and finally 3-butyl-2,5-dimethyl-1,3,4-thiadiazol-3-ium iodide (50 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2O$) δ ppm 0.92 (t, 3H) 1.28-1.39 (m, 2 H) 1.69-1.79 (m, 2 H) 2.45-2.48 (m, 3 H) 4.15 (t, 2 H) 6.18-6.22 (m, 1 H) 6.97 (d, 1 H) 7.55 (d, 1 H); MS (ESI) m/z 295 (M+H)$^+$.

Example 66

(2Z)-2-(3-butyl-5-methyl-1,3,4-thiadiazol-2(3H)-ylidene)-1-(1,3-thiazol-4-yl)ethanone In a 20 mL vial thiazole-2-carboxylic acid (0.9 mL of 0.2 M in DMA, 1.10 equiv) was added followed by the addition of HATU (77 mg in 0.7 mL of DMA, 0.2 mmol, 1.20 equiv.), DIEA (53 mg in 0.7 mL of DMA, 0.4 mmol, 2.40 equiv.), and finally 3-butyl-2,5-dimethyl-1,3,4-thiadiazol-3-ium iodide (50 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2O$) δ ppm 0.89 (t, 3 H) 1.25-1.38 (m, 2 H) 1.69-1.82 (m, 2 H) 2.46 (s, 3 H) 4.12-4.20 (m, 2 H) 6.81 (s, 1 H) 8.24 (s, 1 H) 9.15 (s, 1 H); MS (ESI) m/z 282 (M+H)$^+$.

Example 67

(2Z)-2-(3-butyl-5-methyl-1,3,4-thiadiazol-2(3H)-ylidene)-1-(2-methylphenyl)ethanone In a 20 mL vial 2-methylbenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2O$) δ ppm 0.84-0.93 (m, 3 H) 1.27-1.37 (m, 2 H) 1.67-1.75 (m, 2 H) 2.36, (s, 3 H) 2.47 (s, 3 H) 4.11-4.17 (m, 2 H) 6.19-6.25 (m, 1 H) 7.17-7.26 (m, 2 H) 7.26-7.33 (m, 1 H) 7.43-7.51 (m, 1 H); MS (ESI) m/z 289 (M+H)$^+$.

Example 68

(2Z)-2-(3-butyl-5-methyl-1,3,4-thiadiazol-2(3H)-ylidene)-1-(2-chlorophenyl)ethanone In a 20 mL vial 2-chlorobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2O$) δ ppm 0.89 (t, 3 H) 1.25-1.36 (m, 2 H) 1.66-1.75 (m, 2 H)

2.49-2.50 (m, 3 H) 4.14 (t, 2 H) 6.20 (s, 1 H) 7.35-7.44 (m, 2H) 7.45-7.49 (m, 1 H) 7.50-7.55 (m, 1 H); MS (ESI) m/z 309 (M+H)$^+$.

Example 69

(2Z)-2-(3-butyl-5-methyl-1,3,4-thiadiazol-2(3H)-ylidene)-1-(3-chlorophenyl)ethanone In a 20 mL vial 3-chlorobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-D$_6$/D$_2$O) δ ppm 0.92 (t, 3 H) 1.27-1.40 (m, 2 H) 1.72-1.80 (m, 2 H) 2.47-2.50 (m, 3 H) 4.27 (t, 2 H) 6.76 (s, 1 H) 7.46-7.53 (m, 1 H) 7.52-7.57 (m, 1 H) 7.94-7.99 (m, 1 H) 8.01-8.05 (m, 1 H); MS (ESI) m/z 309 (M+H)$^+$.

Example 70

(2Z)-1-(2-bromophenyl)-2-(3-butyl-5-methyl-1,3,4-thiadiazol-2(3H)-ylidene)ethanone In a 20 mL vial 2-bromobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.88 (t, 3 H) 1.26-1.37 (m, 2 H) 1.67-1.76 (m, 2 H) 2.47 (s, 3 H) 4.15 (t, 2 H) 6.16 (s, 1 H) 7.26-7.36 (m, 1 H) 7.39-7.51 (m, 2 H) 7.59-7.68 (m, 1 H); MS (ESI) m/z 353 (M+H)$^+$.

Example 71

(2Z)-1-(3-bromophenyl)-2-(3-butyl-5-methyl-1,3,4-thiadiazol-2(3H)-ylidene)ethanone In a 20 mL vial 3-bromobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-D$_6$/D$_2$O) δ ppm 0.86-0.96 (m, 3 H) 1.27-1.41 (m, 2 H) 1.69-1.78 (m, 2 H) 2.47-2.49 (m, 3 H) 4.29 (t, 2 H) 6.77 (s, 1 H) 7.36-7.48 (m, 1 H) 7.64-7.70 (m, 1 H) 7.98-8.04 (m, 1 H) 8.12-8.19 (m, 1 H); MS (ESI) m/z 353 (M+H)$^+$.

Example 72

(2Z)-1-(4-bromophenyl)-2-(3-butyl-5-methyl-1,3,4-thiadiazol-2(3H)-ylidene)ethanone In a 20 mL vial 4-bromobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.85-0.94 (m, 3 H) 1.28-1.39 (m, 2 H) 1.67-1.80 (m, 2 H) 2.49 (s, 3 H) 4.20-4.23 (m, 2 H) 6.70 (m, 1 H) 7.64 (d, 2 H) 7.94 (d, 2 H); MS (ESI) m/z 353 (M+H)$^+$.

Example 73

(2Z)-2-(3-butyl-5-methyl-1,3,4-thiadiazol-2(3H)-ylidene)-1-[3-(trifluoromethyl)phenyl]ethanone In a 20 mL vial 3-(trifluoromethyl)benzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.92 (t, 3H) 1.30-1.39 (m, 2 H) 1.72-1.80 (m, 2 H) 2.49-2.51 (m, 3 H) 4.30 (t, 2 H) 6.83-6.85 (m, 1 H) 7.69-7.74 (m, 1 H) 7.80-7.89 (m, 1 H) 8.25-8.30 (m, 1 H) 8.32-8.36 (m, 1H); MS (ESI) m/z 343 (M+H)$^+$.

Example 74

(2Z)-2-(3-butyl-5-methyl-1,3,4-thiadiazol-2(3H)-ylidene)-1-[3-(trifluoromethoxy)phenyl]ethanone In a 20 mL vial 3-(trifluoromethoxy)benzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.90 (t, 3H) 1.27-1.42 (m, 2 H) 1.69-1.80 (m, 2 H) 2.49 (s, 3 H) 4.27 (t, 2 H) 6.78 (s, 1 H) 7.43-7.53 (m, 1 H) 7.58-7.65 (m, 1 H) 7.92 (s, 1 H) 8.03-8.11 (m, 1 H); MS (ESI) m/z 359 (M+H)$^+$.

Example 75

(2Z)-2-(3-butyl-5-methyl-1,3,4-thiadiazol-2(3H)-ylidene)-1-(2,3-dimethylphenyl)ethanone In a 20 mL vial 2,3-dimethylbenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.85-0.91 (m, 3 H) 1.25-1.34 (m, 2 H) 1.65-1.75 (m, 2 H) 2.23 (s, 3 H) 2.27 (s, 3 H) 2.48 (s, 3 H) 4.12 (t, 2 H) 6.09-6.13 (m, 1 H) 7.07-7.14 (m, 1 H) 7.16-7.23 (m, 2 H); MS (ESI) m/z 303 (M+H)$^+$.

Example 76

(2Z)-2-(3-butyl-5-methyl-1,3,4-thiadiazol-2(3H)-ylidene)-1-(2,5-dimethylphenyl)ethanone In a 20 mL vial 2,5-dimethylbenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-D$_6$/D$_2$O) δ ppm 0.84-0.94 (m, 3 H) 1.27-1.33 (m, 2 H) 1.68-1.77 (m, 2 H) 2.30 (s, 6 H) 2.48 (s, 3 H) 4.12 (t, 2 H) 6.20 (1, 1 H) 7.10 (s, 2 H) 7.28 (s, 1 H); MS (ESI) m/z 303 (M+H)$^+$.

Example 77

(2Z)-2-(3-butyl-5-methyl-1,3,4-thiadiazol-2(3H)-ylidene)-1-(3,4-dimethylphenyl)ethanone In a 20 mL vial 3,4-dimethylbenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.87-0.95 (m, 3 H) 1.30-1.41 (m, 2 H) 1.69-1.80 (m, 2 H) 2.23-2.32 (m, 6 H) 2.47 (s, 3 H) 4.21 (t, 2 H) 6.65 (s, 1 H) 7.15-7.27 (m, 1 H) 7.65-7.80 (m, 2 H); MS (ESI) m/z 303 (M+H)$^+$.

Example 78

(2Z)-2-(3-butyl-5-methyl-1,3,4-thiadiazol-2(3H)-ylidene)-1-(3,5-dimethylphenyl)ethanone In a 20 mL vial 3,5-dimethylbenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.87-0.96 (m, 3 H) 1.28-1.39 (m, 2 H) 1.68-1.80 (m, 2 H) 2.33 (s, 6 H) 2.47 (s, 3 H) 4.21 (t, 2 H) 6.66 (s, 1 H) 7.14 (s, 1 H) 7.62 (s, 2 H); MS (ESI) m/z 303 (M+H)$^+$.

Example 79

(2Z)-2-(3-butyl-5-methyl-1,3,4-thiadiazol-2(3H)-ylidene)-1-(2,3-dimethoxyphenyl)ethanone In a 20 mL vial 2,3-dimethoxybenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.86-0.95 (m, 3 H) 1.27-1.38 (m, 2 H) 1.71-1.77 (m, 2 H) 2.48 (s, 3 H) 3.75 (s, 3 H) 3.80 (s, 3 H) 4.10-4.14 (m, 2 H) 6.45 (s, 1 H) 7.08-7.19 (m, 3 H); MS (ESI) m/z 335 (M+H)$^+$.

Example 80

(2Z)-2-(3-butyl-5-methyl-1,3,4-thiadiazol-2(3H)-ylidene)-1-(2,5-dimethoxyphenyl)ethanone In a 20 mL vial 2,5-dimethoxybenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-D$_6$/D$_2$O) δ ppm 0.93 (t, 3 H) 1.30-1.36 (m, 2 H) 1.71-1.79 (m, 2 H) 2.47 (s, 3 H) 3.73 (s, 3 H) 3.80 (s, 3 H) 4.11 (t, 2 H) 6.59 (s, 1 H) 6.96-7.00 (m, 1 H) 7.02-7.06 (m, 1 H) 7.22 (d, 1 H); MS (ESI) m/z 335 (M+H)$^+$.

Example 81

(2Z)-2-(3-butyl-5-methyl-1,3,4-thiadiazol-2(3H)-ylidene)-1-(3,5-dimethoxyphenyl)ethanone In a 20 mL vial 3,5-dimethoxybenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.87-0.97 (m, 3 H) 1.28-1.37 (m, 2 H) 1.71-1.80 (m, 2 H)

2.46-2.48 (m, 3 H) 3.77-3.83 (m, 6 H) 4.23 (t, 2 H) 6.60-6.68 (m, 2 H) 7.10-7.14 (m, 2 H); MS (ESI) m/z 335 (M+H)$^+$.

Example 82

(2Z)-2-(3-butyl-5-methyl-1,3,4-thiadiazol-2(3H)-ylidene)-1-(2,3-dichlorophenyl)ethanone In a 20 mL vial 2,3-dichlorobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.83-0.92 (m, 3 H) 1.25-1.37 (m, 2 H) 1.67-1.75 (m, 2 H) 2.50 (s, 3 H) 4.15 (t, 2 H) 6.18 (s, 1 H) 7.37-7.48 (m, 2 H) 7.64-7.69 (m, 1 H); MS (ESI) m/z 343 (M+H)$^+$.

Example 83

(2Z)-2-(3-butyl-5-methyl-1,3,4-thiadiazol-2(3H)-ylidene)-1-(2,4-dichlorophenyl)ethanone In a 20 mL vial 2,4-dichlorobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.86-0.92 (m, 3 H) 1.25-1.35 (m, 2 H) 1.67-1.77 (m, 2 H) 2.50 (s, 3 H) 4.14 (t, 2 H) 6.21 (s, 1 H) 7.45-7.50 (m, 1 H) 7.56 (d, 1 H) 7.63-7.65 (m, 1 H); MS (ESI) m/z 343 (M+H)$^+$.

Example 84

(2Z)-2-(3-butyl-5-methyl-1,3,4-thiadiazol-2(3H)-ylidene)-1-(2,5-dichlorophenyl)ethanone In a 20 mL vial 2,5-dichlorobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.89 (t, 3 H) 1.27-1.35 (m, 2 H) 1.67-1.76 (m, 2 H) 2.50 (s, 3 H) 4.16 (t, 2 H) 6.25 (s, 1 H) 7.46-7.53 (m, 2 H) 7.55-7.57 (m, 1 H); MS (ESI) m/z 343 (M+H)$^+$.

Example 85

(2Z)-2-(3-butyl-5-methyl-1,3,4-thiadiazol-2(3H)-ylidene)-1-(3,4-dichlorophenyl)ethanone In a 20 mL vial 3,4-dichlorobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.87-0.94 (m, 3 H) 1.28-1.39 (m, 2 H) 1.71-1.80 (m, 2 H) 2.47 (s, 3 H) 4.27 (t, 2 H) 6.81 (s, 1 H) 7.73 (d, 1 H) 7.99 (d, 1 H) 8.22 (s, 1 H); MS (ESI) m/z 343 (M+H)$^+$.

Example 86

(2Z)-2-(3-butyl-5-methyl-1,3,4-thiadiazol-2(3H)-ylidene)-1-(3,5-dichlorophenyl)ethanone In a 20 mL vial 3,5-dichlorobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.92 (t, 3 H) 1.28-1.37 (m, 2 H) 1.71-1.82 (m, 2 H) 2.47-2.53 (m, 3 H) 4.29 (t, 2 H) 6.83 (s, 1 H) 7.73 (s, 1 H) 8.06 (s, 2 H); MS (ESI) m/z 343 (M+H)$^+$.

Example 87

(2Z)-2-(3-butyl-5-methyl-1,3,4-thiadiazol-2(3H)-ylidene)-1-(5-fluoro-2-methylphenyl)ethanone In a 20 mL vial 5-fluoro-2-methylbenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.90 (t, 3 H) 1.68-1.76 (m, 2 H) 2.34 (s, 3 H) 2.48 (s, 3 H) 4.16 (t, 2 H) 6.26 (s, 1 H) 7.10-7.16 (m, 1 H) 7.23-7.32 (m, 2 H); MS (ESI) m/z 307 (M+H)$^+$.

Example 88

(2Z)-2-(3-butyl-5-methyl-1,3,4-thiadiazol-2(3H)-ylidene)-1-(3-methoxy-4-methylphenyl)ethanone In a 20 mL vial 3-methoxy-4-methylbenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.89-0.94 (m, 3 H) 1.29-1.37 (m, 2 H) 1.71-1.79 (m, 2 H) 2.20 (s, 3 H) 2.48 (s, 3H) 3.85 (s, 3 H) 4.23 (t, 2 H) 6.67 (s, 1 H) 7.22 (d, 1 H) 7.48 (s, 1 H) 7.53 (d, 1 H); MS (ESI) m/z 319 (M+H)$^+$.

Example 89

(2Z)-2-(3-butyl-5-methyl-1,3,4-thiadiazol-2(3H)-ylidene)-1-(1-naphthyl)ethanone

In a 20 mL vial 1-naphthoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.87-0.93 (m, 3 H) 1.27-1.35 (m, 2 H) 1.69-1.78 (m, 2 H) 2.51 (s, 3 H) 4.16-4.20 (m, 2 H) 6.40 (s, 1 H) 7.49-7.59 (m, 3 H) 7.73-7.78 (m, 1 H) 7.94-8.01 (m, 2 H) 8.37-8.43 (m, 1 H); MS (ESI) m/z 325 (M+H)$^+$.

Example 90

(2Z)-2-(3-butyl-5-methyl-1,3,4-thiadiazol-2(3H)-ylidene)-1-(2-naphthyl)ethanone

In a 20 mL vial 2-naphthoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.93 (t, 3 H) 1.32-1.41 (m, 2 H) 1.75-1.83 (m, 2 H) 2.50 (s, 3 H) 4.28 (t, 2 H) 6.90 (s, 1 H) 7.93-8.00 (m, 2 H) 8.04-8.08 (m, 1 H) 8.10-8.15 (m, 1 H) 8.61 (s, 1 H); MS (ESI) m/z 325 (M+H)$^+$.

Example 91

(2Z)-2-(3-butyl-5-methyl-1,3,4-thiadiazol-2(3H)-ylidene)-1-(4-tert-butylphenyl)ethanone In a 20 mL vial 4-tert-butylbenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.92 (t, 3 H) 1.30 (s, 9 H) 1.32-1.38 (m, 2 H) 1.71-1.78 (m, 2 H) 2.48 (s, 3 H) 4.21 (t, 2 H) 6.67 (s, 1 H) 7.47 (d, 2 H) 7.91 (d, 2 H); MS (ESI) m/z 331 (M+H)$^+$.

Example 92

(2Z)-2-(3-butyl-5-methyl-1,3,4-thiadiazol-2(3H)-ylidene)-1-[2-fluoro-5-(trifluoromethyl)phenyl]ethanone In a 20 mL vial 2-fluoro-5-(trifluoromethyl)benzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.92 (t, 3 H) 1.26-1.37 (m, 2 H) 1.72-1.79 (m, 2 H) 2.50 (s, 3 H) 4.19 (t, 2 H) 6.47 (s, 1 H) 7.50-7.58 (m, 1 H) 7.87-7.93 (m, 1 H) 8.09-8.12 (m, 1 H); MS (ESI) m/z 361 (M+H)$^+$.

Example 93

(2Z)-2-(3-butyl-5-methyl-1,3,4-thiadiazol-2(3H)-ylidene)-1-[2-chloro-5-(trifluoromethyl)phenyl]ethanone In a 20 mL vial 2-chloro-5-(trifluoromethyl)benzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.89 (t, 3 H) 1.26-1.36 (m, 2 H) 1.69-1.76 (m, 2 H) 2.50 (s, 3 H) 4.17 (t, 2 H) 6.29 (s, 1 H) 7.69-7.76 (m, 1 H) 7.77-7.82 (m, 2 H); MS (ESI) m/z 377 (M+H)$^+$.

Example 94

(2Z)-1-(5-bromo-2-chlorophenyl)-2-(3-butyl-5-methyl-1,3,4-thiadiazol-2(3H)-ylidene)ethanone In a 20 mL vial 5-bromo-2-chlorobenzoic acid (0.9 mL of 0.2 M in DMA, 1.10 equiv) was added followed by the addition of HATU (76 mg in 0.7 mL of DMA, 0.2 mmol, 1.20 equiv.), DIEA (51 mg in 0.7 mL of DMA, 0.4 mmol, 2.40 equiv.), and finally 3-butyl-2,5-dimethyl-1,3,4-thiadiazol-3-ium iodide (49 mg in 0.7 mL of DMA, 0.17 mmol, 1 equiv.). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.89 (t, 3 H) 1.25-1.36 (m, 2 H) 1.68-1.76 (m, 2 H) 2.51 (s, 3 H) 4.16 (t, 2 H) 6.26 (s, 1 H) 7.42-7.46 (m, 1 H) 7.58-7.63 (m, 1 H) 7.65-7.68 (m, 1 H); MS (ESI) m/z 387 (M+H)$^+$.

Example 95

(2Z)-2-(3-butyl-4,5-dimethyl-1,3-thiazol-2(3H)-ylidene)-1-(2,6-difluorophenyl)ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 2,6-difluorobenzoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2$O) δ ppm 0.89 (t, 3 H) 1.28-1.38 (m, 2 H) 1.55-1.64 (m, 2 H) 2.20 (s, 3 H) 2.22 (s, 3 H) 3.91-3.96 (m, 2 H) 6.03 (s, 1 H) 7.07-7.15 (m, 2 H) 7.39-7.47 (m, 1 H); MS (ESI) m/z 324 (M+H)$^+$.

Example 96

(2Z)-2-(3-butyl-4,5-dimethyl-1,3-thiazol-2(3H)-ylidene)-1-(2,4-dichlorophenyl)ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 2,4-dichlorobenzoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$D_6$/$D_2$O) δ ppm 0.90 (t, 3 H) 1.30-1.40 (m, 2 H) 1.58-1.65 (m, 2 H) 2.21 (s, 3 H) 2.23 (s, 3 H) 3.94-3.99 (m, 2 H) 6.11 (s, 1 H) 7.46 (dd, 1 H) 7.52-7.57 (m, 1 H) 7.62 (d, 1 H); MS (ESI) m/z 356 (M+H)$^+$.

Example 97

(2Z)-2-(3-butyl-4,5-dimethyl-1,3-thiazol-2(3H)-ylidene)-1-[2-(trifluoromethyl)phenyl]ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 2-(trifluoromethyl)benzoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2$O) δ ppm 0.89 (t, 3 H) 1.27-1.37 (m, 2 H) 1.56-1.63 (m, 2 H) 2.19 (s, 3 H) 2.21 (s, 3 H) 3.90-3.96 (m, 2 H) 5.99 (s, 1 H) 7.52-7.61 (m, 2 H) 7.66-7.71 (m, 1 H) 7.72-7.77 (m, 1 H); MS (ESI) m/z 356 (M+H)$^+$.

Example 98

(2Z)-2-(3-butyl-4,5-dimethyl-1,3-thiazol-2(3H)-ylidene)-1-[3-(trifluoromethyl)phenyl]ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 3-(trifluoromethyl)benzoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2$O) δ ppm 0.94 (t, 3 H) 1.35-1.44 (m, 2 H) 1.61-1.68 (m, 2 H) 2.19 (s, 3H) 2.21 (s, 3 H) 4.07-4.13 (m, 2 H) 6.64 (s, 1 H) 7.66-7.70 (m, 1 H) 7.79 (d, 1 H) 8.18-8.20 (m, 1 H) 8.25 (d, 1H); MS (ESI) m/z 356 (M+H)$^+$.

Example 99

(2Z)-2-(3-butyl-4,5-dimethyl-1,3-thiazol-2(3H)-ylidene)-1-cyclopentylethanone

In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by cyclopentanecarbonyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2$O) δ ppm 0.88-0.97 (m, 3 H) 1.30-1.39 (m, 2 H) 1.51-1.62 (m, 4 H) 1.62-1.70 (m, 3 H) 1.77-1.87 (m, 2 H) 2.16-2.26 (m, 5 H) 2.73-2.86 (m, 1 H) 3.71-3.83 (m, 4 H) 5.84-5.94 (m, 1 H); MS (ESI) m/z 280 (M+H)$^+$.

Example 100

4-[(2Z)-2-(3-butyl-4,5-dimethyl-1,3-thiazol-2(3H)-ylidene)ethanoyl]benzonitrile

In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 4-cyanobenzoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/$D_2$O) δ ppm 0.93 (t, 3 H) 1.32-1.45 (m, 2 H) 1.60-1.68 (m, 2 H) 2.19 (s, 3 H) 2.23 (s, 3 H) 4.06-4.12 (m, 2 H) 6.67 (s, 1 H) 7.90 (d, 2 H) 8.10 (d, 2 H); MS (ESI) m/z 313 (M+H)$^+$.

Example 101

(2Z)-2-(3-butyl-4,5-dimethyl-1,3-thiazol-2(3H)-ylidene)-1-(1-naphthyl)ethanone

In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 1-naphthoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.89 (t, 3 H) 1.29-1.39 (m, 2 H) 1.59-1.69 (m, 2 H) 2.26 (s, 6H) 4.02-4.07 (m, 2 H) 6.30 (s, 1 H) 7.50-7.59 (m, 3 H) 7.68-7.71 (m, 1 H) 7.94-8.01 (m, 2 H) 8.30-8.34 (m, 1 H); MS (ESI) m/z 338 (M+H)$^+$.

Example 102

(2Z)-2-(3-butyl-4,5-dimethyl-1,3-thiazol-2(3H)-ylidene)-1-(2,5-difluorophenyl)ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 2,5-difluorobenzoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.94 (t, 3 H) 1.33-1.41 (m, 2 H) 1.60-1.69 (m, 2 H) 2.19 (s, 3 H) 2.22 (s, 3 H) 3.93-4.00 (m, 2 H) 6.38 (s, 1 H) 7.24-7.35 (m, 2 H) 7.51-7.59 (m, 1 H); MS (ESI) m/z 324 (M+H)$^+$.

Example 103

(2Z)-2-(3-butyl-4,5-dimethyl-1,3-thiazol-2(3H)-ylidene)-1-pyridin-3-ylethanone

In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by nicotinoyl chloride hydrochloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.94 (t, 3 H) 1.36-1.46 (m, 2 H) 1.61-1.68 (m, 2 H) 2.19 (s, 3 H) 2.22 (s, 3 H) 4.07-4.12 (m, 2 H) 6.69 (s, 1 H) 7.68-7.78 (m, 1 H) 8.54-8.61 (m, 1 H) 8.72-8.80 (m, 1 H) 9.18-9.29 (m, 1 H); MS (ESI) m/z 289 (M+H)$^+$.

Example 104

(2Z)-1-(1,3-benzodioxol-5-yl)-2-(3-butyl-4,5-dimethyl-1,3-thiazol-2(3H)-ylidene)ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by benzo[d][1,3]dioxole-5-carbonyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.93 (t, 3 H) 1.34-1.44 (m, 2 H) 1.58-1.68 (m, 2 H) 2.16 (s, 3 H) 2.20 (s, 3 H) 4.02-4.09 (m, 2 H) 6.08 (s, 2 H) 6.48 (s, 1 H) 6.93-6.99 (m, 1 H) 7.47-7.48 (m, 1 H) 7.49-7.54 (m, 1 H); MS (ESI) m/z 332 (M+H)$^+$.

Example 105

(2Z)-2-(3-butyl-4,5-dimethyl-1,3-thiazol-2(3H)-ylidene)-1-(2-chloropyridin-3-yl)ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 2-chloronicotinoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.91 (t, 3 H) 1.31-1.39 (m, 2 H) 1.58-1.67 (m, 2 H) 2.19 (s, 3 H) 2.21 (s, 3 H) 3.93-3.98 (m, 2 H) 6.15 (s, 1 H) 7.47 (dd, 1 H) 7.94 (dd, 1 H) 8.41 (dd, 1 H); MS (ESI) m/z 323 (M+H)$^+$.

Example 106

(2Z)-1-[2,5-bis(trifluoromethyl)phenyl]-2-(3-butyl-4,5-dimethyl-1,3-thiazol-2(3H)-ylidene)ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 2,5-bis(trifluoromethyl)benzoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-$d_6$/D$_2$O) δ ppm 0.89 (t, 3 H) 1.28-1.38 (m, 2 H) 1.56-1.64 (m, 2 H) 2.19 (s, 3 H) 2.23 (s, 3 H) 3.92-3.98 (m, 2 H) 6.02 (s, 1 H) 7.82-7.84 (m, 1 H) 7.93-7.97 (m, 1 H) 7.98-8.02 (m, 1 H); MS (ESI) m/z 424 (M+H)$^+$.

Example 107

(2Z)-2-(3-butyl-4,5-dimethyl-1,3-thiazol-2(3H)-ylidene)-1-[5-fluoro-2-(trifluoromethyl)phenyl]ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 5-fluoro-2-(trifluoromethyl)benzoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ PPM 0.89 (t, 3 H) 1.28-1.37 (m, 2 H) 1.56-1.63 (m, 2 H) 2.18 (s, 3 H) 2.21 (s, 3 H) 3.90-3.97 (m, 2 H) 5.99 (2, 1 H) 7.36-7.44 (m, 2 H) 7.79-7.83 (m, 1 H); MS (ESI) m/z 374 (M+H)$^+$.

Example 108

(2Z)-2-(3-butyl-4,5-dimethyl-1,3-thiazol-2(3H)-ylidene)-1-(3-methylthien-2-yl)ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 3-methylthiophene-2-carbonyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.95 (t, 3 H) 1.34-1.43 (m, 2 H) 1.60-1.71 (m, 2 H) 2.17 (s, 3 H) 2.20 (s, 3 H) 2.47 (s, 3 H) 3.92-3.98 (m, 2 H) 6.13 (s, 1 H) 6.91-6.96 (m, 1 H) 7.46-7.52 (m, 1 H); MS (ESI) m/z 308 (M+H)$^+$.

Example 109

(2Z)-2-(3-butyl-4,5-dimethyl-1,3-thiazol-2(3H)-ylidene)-1-(5-fluoro-2-methylphenyl)ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 5-fluoro-2-methylbenzoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.91 (t, 3 H) 1.30-1.41 (m, 2 H) 1.55-1.68 (m, 2 H) 2.20 (s, 3 H) 2.22 (s, 3 H) 2.33 (s, 3 H) 3.96-4.04 (m, 2 H) 6.09 (s, 1 H) 7.08-7.14 (m, 1 H) 7.19-7.27 (m, 2 H); MS (ESI) m/z 320 (M+H)$^+$.

Example 110

(2Z)-2-(3-butyl-4,5-dimethyl-1,3-thiazol-2(3H)-ylidene)-1-(5-chloro-2-fluorophenyl)ethanone In a 20 mL vial 3-butyl-2,4,5-trimethylthiazol-3-ium iodide (48 mg in 0.5 mL DMA, 0.16 mmol, 1 equiv.) was added, followed by TEA (38 mg in 0.5 mL DMA, 0.37 mmol, 2.4 equiv.) and the solution went black. DMAP (2 mg in 0.5 mL DMA, 0.016 mmol, 0.1 equiv) was added next, followed by 5-chloro-2-fluorobenzoyl chloride (0.9 mL of 0.2M in DMA, 1.2 equiv). The mixture was shaken overnight at room temperature and then concentrated in vacuo. The resulting residue was taken up in 1:1 DMSO/MeOH and purified by reverse phase HPLC using a method analogous to that described in Example 53 to provide the title compound. $^1$H NMR (500 MHz, DMSO-d$_6$/D$_2$O) δ ppm 0.93 (t, 3 H) 1.33-1.42 (m, 2 H) 1.61-1.68 (m, 2 H) 2.19 (s, 3 H) 2.23 (s, 3 H) 3.94-4.01 (m, 2 H) 6.36 (s, 1 H) 7.27-7.35 (m, 1 H) 7.47-7.53 (m, 1 H) 7.75-7.81 (m, 1H); MS (ESI) m/z 340 (M+H)$^+$.

Example 111

(2Z)-2-(3-butyl-1,3-thiazol-2(3H)-ylidene)-1-(5-chloro-2-methoxyphenyl)ethanone

To a stirred suspension of NaH (60% in mineral oil, 0.04 g, 1 mmol) in anhydrous DMF (3 mL) at 0° C. was added 5-chloro-2-methoxyacetophenone (0.15 g, 1 mmol) followed by subsequent addition of n-butylisothiocyanate (0.24 mL, 2 mmol) in DMF (3 mL). The mixture was stirred at 0° C. for 2 hours after which 2-bromo-1,1-dimethoxyethane was added. The reaction mixture was stirred for 2 hr and then poured into brine, extracted with EtOAc. The organic layer was washed with brine (3×30 mL), dried (MgSO$_4$) and concentrated. The residue was dissolved in toluene (10 mL) then treated with p-toluenesulfonic acid (1.5 mmol) and refluxed for 6 hr. The reaction mixture was concentrated and partitioned between EtOAc and saturated NaHCO$_3$. The organic layer was washed with brine, dried (MgSO$_4$) and concentrated. The residue was purified by flash chromatography eluting with 50% ethyl acetate in hexane to provide the title compound as a yellow solid. (10 mg). $^1$H NMR (300 MHz, DMSO-d$_6$) δ ppm 0.93 (t, J=7.3 Hz, 3 H), 1.32 (dd, J=15.1, 7.3 Hz, 2 H), 1.72 (t, J=7.3 Hz, 2 H), 3.86 (s, 3 H), 4.01 (t, J=7.1 Hz, 2 H), 6.57 (s, 1 H), 6.81 (d, J=4.4 Hz, 1 H), 7.12 (d, J=8.8 Hz, 1 H), 7.33-7.48 (m, 1 H), 7.34-7.49 (m, 1 H), 7.65 (d, J=3.1 Hz, 1 H). MS (DCI), m/z 324 (M+H)$^+$.

Example 112

(Z)-2-(3-butyl-5-((E)-1-(methoxyimino)ethyl)-4-methylthiazol-2(3H)-ylidene)-1-(5-chloro-2-methoxyphenyl)ethanone The title compound was prepared as described in Example 17 by replacing the NH$_2$OH_HCl with NH$_2$OCH$_3$.HCl. The residue was purified by flash chromatography eluting with ethyl acetate to separate the mixture of E and Z isomers. E isomer (less polar). $^1$H NMR (300 MHz, DMSO-d$_6$) δ ppm 0.97 (t, J=7.3 Hz, 3 H), 1.31-1.49 (m, 2 H), 1.59-1.81 (m, 2 H), 2.18 (s, 3 H), 2.44 (s, 3 H), 3.88 (d, J=9.2 Hz, 6H), 3.92-4.03 (m, 2 H), 6.64 (s, 1 H), 7.14 (d, J=8.8 Hz, 1 H), 7.43 (dd, J=8.8, 3.1 Hz, 1 H), 7.65 (d, J=3.1 Hz, 1 H). MS (DCI), m/z 409 (M+H)$^+$. Anal calcd for C$_{20}$H$_{25}$ClN$_2$O$_3$S: C, 58.74; H, 6.16; N, 6.85. Found: C, 58.70; H, 6.12; N, 6.79.

Example 113

(Z)-2-(3-butyl-5-((Z)-1-(methoxyimino)ethyl)-4-methylthiazol-2(3H)-ylidene)-1-(5-chloro-2-methoxyphenyl)ethanone The title compound was isolated from the synthesis of example 112. Z isomer (more polar). $^1$H NMR (300 MHz, DMSO-d$_6$) δ ppm 0.97 (t, J=7.3 Hz, 3 H), 1.32-1.51 (m, 2 H), 1.60-1.81 (m, 2 H), 2.13 (s, 3 H), 2.21 (s, 3 H), 3.81 (s, 3 H), 3.87 (s, 3 H), 3.89-4.04 (m, 2 H), 6.63 (s, 1 H), 7.13 (d, J=9.2 Hz, 1 H), 7.43 (dd, J=8.8, 2.7 Hz, 1 H), 7.65 (d, J=3.1 Hz, 1 H). MS (DCI), m/z 409 (M+H)$^+$. Anal calcd for C$_{20}$H$_{25}$ClN$_2$O$_3$S: C, 58.74; H, 6.16; N, 6.85. Found: C, 58.65; H, 6.10; N, 6.69.

Example 114

(2Z)-2-[3-butyl-4-(trifluoromethyl)-1,3-thiazol-2(3H)-ylidene]-1-(5-chloro-2-methoxyphenyl)ethanone

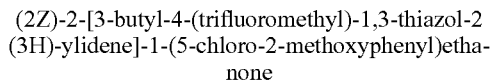

The title compound was prepared as described in Example 16 by replacing the 3-chloropentane-2,4-dione with 3-bromo-1,1,1-trifluoropropan-2-one (40 mg). $^1$H NMR (500 MHz, DMSO-$d_6$) δ ppm 0.96 (t, J=7.3 Hz, 3 H), 1.39-1.48 (m, 2 H), 1.67-1.79 (m, 2 H), 3.88 (s, 3 H), 3.95-4.04 (m, 2 H), 6.74 (s, 1 H), 7.17 (d, J=8.8 Hz, 1 H), 7.47 (dd, J=8.7, 2.9 Hz, 1 H), 7.63-7.76 (m, 2 H). MS (DCI), m/z 392 (M+H)$^+$. Anal calcd for $C_{17}H_{17}ClDF_3NO_2S$: C, 52.11; H, 4.37; N, 3.57. Found: C, 51.85; H, 4.21; N, 3.42.

Example 115

(2Z)-2-[3-butyl-5-methyl-4-(trifluoromethyl)-1,3-thiazol-2(3H)-ylidene]-1-(5-chloro-2-methoxyphenyl)ethanone The title compound was prepared as described in Example 16 by replacing the 3-chloropentane-2,4-dione with 3-bromo-1,1,1-trifluorobutan-2-one. $^1$H NMR (300 MHz, DMSO-$d_6$) δ ppm 0.96 (t, J=7.3 Hz, 3 H), 1.33-1.51 (m, 2 H), 1.63-1.83 (m, 2 H), 2.38 (q, J=3.3 Hz, 3 H), 3.87 (s, 3 H), 3.89-4.01 (m, 2 H), 6.68 (s, 1 H), 7.16 (d, J=8.8 Hz, 1 H), 7.47 (dd, J=8.8, 3.1 Hz, 1 H), 7.66 (d, J=3.1 Hz, 1 H). MS (DCI), m/z 406 (M+H)$^+$. Anal calcd for $C_{18}H_{19}ClF_3NO_2S$: C, 53.27; H, 4.72; N, 3.45. Found: C, 53.16; H, 4.40; N, 3.39

Example 116

(Z)-2-(5-acetyl-3-(3-fluorobenzyl)-4-methylthiazol-2(3H)-ylidene)-1-(5-chloro-2-methoxyphenyl)ethanone

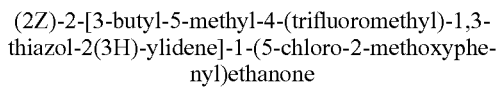

The title compound was prepared as described in Example 16 by replacing the n-butylisothiocyanate with 3-fluorobenzylisothiocyanate (30 mg). $^1$H NMR (300 MHz, DMSO-$d_6$) δ ppm 2.64 (s, 3 H), 3.29 (s, 3 H), 3.64 (s, 3 H), 5.36 (s, 2 H), 6.68 (s, 1 H), 6.94-7.25 (m, 4 H), 7.36-7.52 (m, 2 H), 7.57 (d, J=2.7 Hz, 1 H). MS (DCI), m/z 432 (M+H)$^+$. Anal calcd for $C_{22}H_{19}ClFNO_3S$: C, 61.18; H, 4.43; N, 3.24. Found: C, 60.82; H, 4.30; N, 3.15

Example 117

(2Z)-1-(5-chloro-2-methoxyphenyl)-2-[3-(3-fluorobenzyl)-4,5-dimethyl-1,3-thiazol-2(3H)-ylidene]ethanone

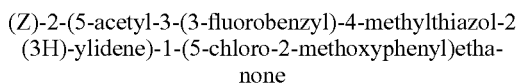

The title compound was prepared as described in Example 16 by replacing the 3-chloropentane-2,4-dione with 3-bromobutan-2-one and n-butylisothiocyanate with 3-fluorobenzylisothiocyanate (20 mg). $^1$H NMR (300 MHz, DMSO-$d_6$) δ ppm 2.19 (d, J=7.5 Hz, 6 H), 3.62-3.67 (m, 3 H), 5.24 (s, 2 H), 6.47 (s, 1 H), 6.92-7.08 (m, 3 H), 7.09-7.22 (m, 1 H), 7.31-7.50 (m, 2 H), 7.57 (d, J=2.7 Hz, 1 H). MS (DCI), m/z 404 (M+H)$^+$. Anal calcd for $C_{21}H_{19}ClFNO_2S$: C, 62.45; H, 4.74; N, 3.47. Found: C, 62.38; H, 4.67; N, 3.39

Example 118

(Z)-1-(5-chloro-2-methoxyphenyl)-2-(5-((E)-1-(methoxyimino)ethyl)-4-methyl-3-((tetrahydrofuran-2-yl)methyl)thiazol-2(3H)-ylidene)ethanone

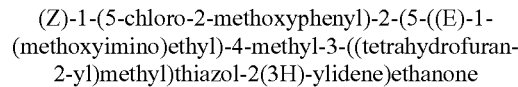

The title compound was prepared as described in Example 112 by replacing the n-butylisothiocyanate with 2-(isothiocyanatomethyl)tetrahydrofuran. The residue was purified by flash chromatography eluting with ethyl acetate to separate the mixture of E and Z isomers. E isomer (less polar): $^1$H NMR (300 MHz, DMSO-$d_6$) δ ppm 1.66 (dd, J=11.9, 8.5 Hz, 1 H), 1.79-2.01 (m, 2 H), 2.01-2.14 (m, 1 H), 2.18 (s, 3 H), 2.44 (s, 3 H), 3.58-3.72 (m, 1 H), 3.80 (t, J=7.5 Hz, 1 H), 3.88 (d, J=11.5 Hz, 6 H), 4.07 (d, J=5.8 Hz, 2 H), 4.24 (t, J=6.1 Hz, 1 H), 6.63 (s, 1 H), 7.13 (d, J=8.8 Hz, 1 H), 7.43 (dd, J=8.8, 3.1 Hz, 1 H), 7.63 (d, J=2.7 Hz, 1 H). MS (DCI), m/z 437 (M+H)$^+$. Anal calcd for $C_{21}H_{25}ClN_2O_4S$: C, 57.72; H, 5.77; N, 6.74. Found: C, 57.74; H, 5.84; N, 6.41.

Example 119

(Z)-1-(5-chloro-2-methoxyphenyl)-2-(5-((Z)-1-(methoxyimino)ethyl)-4-methyl-3-((tetrahydrofuran-2-yl)methyl)thiazol-2(3H)-ylidene)ethanone The title compound was isolated from the reaction mixture of Example 118. Z isomer (more polar): $^1$H NMR (300 MHz, DMSO-$d_6$) δ ppm 1.57-1.77 (m, 1 H), 1.78-1.97 (m, 2 H), 2.02-2.12 (m, 1 H), 2.11-2.16 (m, 3 H), 2.17-2.25 (m, 3 H), 3.59-3.71 (m, 1 H), 3.77-3.88 (m, 6 H), 3.96-4.09 (m, 2 H), 4.18-4.31 (m, 1 H), 5.75 (s, 1 H), 6.62 (s, 1 H), 7.13 (d, J=8.8 Hz, 1 H), 7.43 (dd, J=8.8, 2.7 Hz, 1 H), 7.63 (d, J=3.1 Hz, 1 H). MS (DCI), m/z 437 (M+H)$^+$. Anal calcd for $C_{21}H_{25}ClN_2O_4S$: C, 57.72; H, 5.77; N, 6.74. Found: C, 57.73; H, 5.88; N, 6.46.

Example 120

(2Z)-3-butyl-2-[2-(5-chloro-2-methoxyphenyl)-2-oxoethylidene]-5,5-dimethyl-2,3,5,6-tetrahydro-1,3-benzothiazol-7(4H)-one

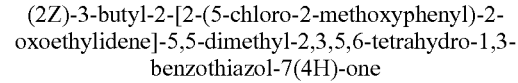

The title compound was prepared as described in Example 16 by replacing the 3-chloropentane-2,4-dione with 2-chloro-5,5-dimethylcyclohexane-1,3-dione (13 mg). $^1$H NMR (300 MHz, CDCl$_3$) δ ppm 0.98-1.07 (m, 3 H), 1.15-1.22 (m, 6 H), 1.36-1.53 (m, 2 H), 1.70-1.88 (m, 2 H), 2.44 (s, 2 H), 2.62 (s, 2 H), 3.80-3.92 (m, 5 H), 6.73 (s, 1 H), 6.88 (d, J=8.8 Hz, 1 H), 7.32 (dd, J=8.8, 2.7 Hz, 1 H), 7.86 (d, J=2.7 Hz, 1 H). MS (DCI), m/z 420 (M+H)$^+$.

Example 121

(2Z)-2-(3-butyl-5-tert-butyl-1,3-thiazol-2(3H)-ylidene)-1-(5-chloro-2-methoxyphenyl)ethanone

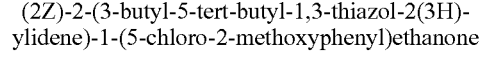

The title compound was prepared as described in Example 35C by replacing 3-chlorothiophene-2-carbonyl chloride with 5-chloro-2-methoxy-benzoyl chloride and Example 35B with Example 153C. $^1$H NMR (300 MHz, CDCl$_3$) δ ppm 0.99 (t, J=7.3 Hz, 3 H), 1.30-1.38 (m, 9 H), 1.38-1.48 (m, 2 H), 1.71-1.91 (m, 2 H), 3.78-3.91 (m, 5 H), 6.45 (s, 1 H), 6.50 (s, 1 H), 6.86 (d, J=8.5 Hz, 1 H), 7.28 (d, J=3.1 Hz, 1 H), 7.88 (d, J=2.7 Hz, 1 H). MS (DCI), m/z 380 (M+H)$^+$. Anal calcd for $C_{20}H_{26}ClNO_2S$: C, 63.22; H, 6.90; N, 3.69. Found: C, 62.40; H, 6.71; N, 3.62.

Example 122

(2Z)-2-(5-tert-butyl-3-isobutyl-1,3-thiazol-2(3H)-ylidene)-1-(5-chloro-2-methoxyphenyl)ethanone The title compound was prepared as described in Example 16 by replacing 3-chloropentane-2,4-dione with 2-chloro-3,3-dimethylbutanal and replacing the n-butylisothiocyanate with isobutylisothiocyanate (16 mg). $^1$H NMR (300 MHz, CDCl$_3$) δ ppm 0.99 (d, J=6.8 Hz, 6 H), 1.30-1.39 (m, 9 H), 2.18-2.41 (m, 1 H), 3.67 (d, J=7.1 Hz, 2 H), 3.82-3.92 (m, 3 H), 6.52 (s, 1 H), 6.86 (d, J=8.8 Hz, 2 H), 7.24-7.35 (m, 1 H), 7.87 (d, J=2.7 Hz, 1 H). MS (DCI), m/z 380 (M+H)$^+$.

Example 123

(2Z)-2-[3-butyl-4-methyl-5-(2,2,2-trifluoro-1-hydroxy-1-methylethyl)-1,3-thiazol-2(3H)-ylidene]-1-(5-chloro-2-methoxyphenyl)ethanone

Example 123A (Z)-2-(3-butyl-4-methyl-5-(1,1,1-trifluoro-2-(trimethylsilyloxy)propan-2-yl)thiazol-2(3H)-ylidene)-1-(5-chloro-2-methoxyphenyl)ethanone Example 16 (189 mg, 0.5 mmol) in THF was treated with trimethylsilyltrifluoromethane 0.5M solution in THF (2 ml, 1 mmol) and trimethylamine N-oxide (6 mg). The reaction mixture was stirred at room temperature for 18 hours then poured into brine, extracted with EtOAc, dried (MgSO$_4$) and concentrated. The residue was purified by flash chromatography using CH$_2$Cl$_2$+0-10% EtOAc as eluent to give 80 mg of the title compound. $^1$H NMR (300 MHz, DMSO-d$_6$) δ ppm 0.12-0.22 (m, 9 H), 0.96 (t, J=7.3 Hz, 3 H), 1.32-1.48 (m, 2 H), 1.67 (s, 2 H), 1.87 (s, 3 H), 2.41 (s, 3 H), 3.86 (s, 3 H), 3.96 (d, J=15.6 Hz, 2 H), 6.59 (s, 1 H), 7.13 (d, J=9.2 Hz, 1 H), 7.42 (dd, J=8.8, 2.7 Hz, 1 H), 7.63 (d, J=2.7 Hz, 1 H). MS (DCI), m/z 523 (M+H)$^+$.

Example 123B (2Z)-2-[3-butyl-4-methyl-5-(2,2,2-trifluoro-1-hydroxy-1-methylethyl)-1,3-thiazol-2(3H)-ylidene]-1-(5-chloro-2-methoxyphenyl)ethanone The product from Example 123A (80 mg, 0.015 mmol) in THF at 0° C. was treated with TBAF (0.015 mmol) and stirred for 1 hr. The reaction mixture was partitioned between EtOAc and brine, dried (MgSO$_4$), concentrated and the residue was purified by flash chromatography eluting with 0-100% EtoAc in hexane to give 60 mg of the title compound. $^1$H NMR (300 MHz, DMSO-d$_6$) δ ppm 0.96 (t, J=7.3 Hz, 3 H), 1.33-1.49 (m, 2 H), 1.66 (d, J=7.1 Hz, 2 H), 1.74 (s, 3 H), 2.41 (s, 3 H), 3.86 (s, 3 H), 3.90-4.01 (m, 2 H), 6.57 (s, 1 H), 7.05 (s, 1 H), 7.12 (d, J=8.8 Hz, 1 H), 7.42 (dd, J=8.8, 2.7 Hz, 1 H), 7.64 (d, J=3.1 Hz, 1 H). MS (DCI), m/z 450 (M+H)$^+$. Anal calcd for C$_{20}$H$_{23}$ClF$_3$NO$_3$S: C, 53.39; H, 5.15; N, 3.11. Found: C, 53.20; H, 5.01; N, 2.89.

Example 124

(2Z)-2-[5-tert-butyl-3-(tetrahydrofuran-2-ylmethyl)-1,3-thiazol-2(3H)-ylidene]-1-(5-chloro-2-methoxyphenyl)ethanone The title compound was prepared as described in Example 16 by replacing 3-chloropentane-2,4-dione with 2-chloro-3,3-dimethylbutanal and replacing n-butylisothiocyanate with 2-isothiocyanatomethyltetrahydrofuran. $^1$H NMR (300 MHz, DMSO-d$_6$) δ ppm 1.30 (s, 9 H), 1.54-1.70 (m, 1 H), 1.76-1.91 (m, 2 H), 1.90-2.07 (m, 1 H), 3.59-3.73 (m, 1 H), 3.74-3.89 (m, 4 H), 3.90-4.10 (m, 2 H), 4.22 (d, J=6.1 Hz, 1 H), 6.49 (s, 1 H), 7.01-7.17 (m, 2 H), 7.39 (dd, J=8.6, 2.9 Hz, 1 H), 7.59 (d, J=2.7 Hz, 1 H). MS (DCI), m/z 408 (M+H)$^+$. Anal calcd for C$_{21}$H$_{26}$ClNO$_3$S: C, 61.83; H, 6.42; N, 3.43. Found: C, 61.51; H, 6.12; N, 3.35.

Example 125

(2Z)-1-(5-chloro-2-methoxyphenyl)-2-[3-isobutyl-5-methyl-4-(trifluoromethyl)-1,3-thiazol-2(3H)-ylidene]ethanone The title compound was prepared as described in Example 16 by replacing n-butylisothiocyanate with isobutylisothiocyanate and 3-chloropentane-2,4-dione with 3-bromo-1,1,1-trifluorobutan-2-one. $^1$H NMR (300 MHz, DMSO-d$_6$) δ ppm 0.92 (d, J=6.8 Hz, 6 H), 2.38 (q, J=3.4 Hz, 4 H), 3.79-3.92 (m, 5 H), 6.71 (s, 1 H), 7.16 (d, J=8.8 Hz, 1 H), 7.46 (dd, J=8.8, 2.7 Hz, 1 H), 7.64 (d, J=2.7 Hz, 1 H). MS (DCI), m/z 406 (M+H)$^+$. Anal calcd for C$_{18}$H$_{19}$ClF$_3$NO$_2$S: C, 53.27; H, 4.72; N, 3.45. Found: C, 53.34; H, 4.84; N, 3.44.

Example 126

(2E)-2-(3-butyl-4-tert-butyl-1,3-thiazol-2(3H)-ylidene)-1-(5-chloro-2-methoxyphenyl)-2-fluoroethanone Example 46 (95 mg, 0.25 mmol) in CH$_2$Cl$_2$ was treated with SelectFluor™ (90 mg, 0.25 mmol) and the reaction mixture was stirred at room temperature for 24 hours. The residue was partitioned between EtOAc and water, dried (MgSO$_4$) and concentrated. Purification by silica gel flash chromatography using 0-10% EtOAc in CH$_2$Cl$_2$ provided the title compound. (30 mg). $^1$H NMR (300 MHz, DMSO-d$_6$) δ ppm 0.91 (t, J=7.5 Hz, 3 H), 1.31-1.43 (m, 11 H), 1.65 (d, J=1.7 Hz, 2 H), 3.77 (s, 3 H), 4.15-4.30 (m, 2 H), 6.54 (d, J=1.7 Hz, 1 H), 7.10 (d, J=8.8 Hz, 1 H), 7.23 (d, J=2.7 Hz, 1 H), 7.43 (dd, J=8.8, 2.7 Hz, 1 H). MS (DCI), m/z 398 (M+H)$^+$.

Example 127

(2E)-2-(3-butyl-5-tert-butyl-1,3-thiazol-2(3H)-ylidene)-1-(5-chloro-2-methoxyphenyl)-2-fluoroethanone The title compound was prepared as described in Example 126 by replacing Example 46 with Example 121 (12 mg). $^1$H NMR (300 MHz, CHLOROFORM-D) δ ppm 0.95 (t, J=7.3 Hz, 3 H), 1.22-1.37 (m, 11 H), 1.78 (s, 2 H), 3.81 (s, 3 H), 4.01-4.11 (m, 2 H), 6.41 (s, 1 H), 6.86 (d, J=8.8 Hz, 1 H), 7.27-7.33 (m, 1 H), 7.37 (d, J=2.0 Hz, 1 H). MS (DCI), m/z 398 (M+H)$^+$. Anal calcd for C$_{20}$H$_{25}$ClFNO$_2$S: C, 60.37; H, 6.33; N, 3.52. Found: C, 60.01; H, 6.12; N, 3.32

Example 128

(2Z)-2-(3-butyl-5-isopropenyl-1,3-thiazol-2(3H)-ylidene)-1-(5-chloro-2-methoxyphenyl)ethanone The title compound was isolated as a by-product from the synthesis of Example 121 (400 mg). $^1$H NMR (300 MHz, DMSO-d$_6$) δ ppm 0.85-1.00 (m, 3 H), 1.25-1.43 (m, 2 H), 1.65-1.82 (m, 2 H), 2.04 (s, 3 H), 3.80-3.90 (m, 3 H), 3.98 (t, J=7.3 Hz, 2 H), 5.04 (d, J=19.8 Hz, 2 H), 6.58 (s, 1 H), 7.13 (d, J=9.1 Hz, 1 H), 7.43 (dd, J=8.7, 2.8 Hz, 1 H), 7.50 (s, 1 H), 7.64 (d, J=2.8 Hz, 1 H). MS (DCI), m/z 398 (M+H)$^+$. Anal calcd for $C_{19}H_{22}ClNO_2S$: C, 62.71; H, 6.09; N, 3.85. Found: C, 62.95; H, 5.97; N, 3.86

Example 129

(1Z)-1-(3-butyl-4,5-dimethyl-1,3-thiazol-2(3H)-ylidene)-4,4-dimethylpentan-2-one The title compound was prepared as described in Example 1B by replacing 5-chloro-2-methoxy-benzoyl chloride with 3,3-dimethylbutanoyl chloride. $^1$H NMR (300 MHz, DMSO-$d_6$) δ 0.93 (t+s, 12H), 1.34 (sextet, J=7 Hz, 2H), 1.57 (quintet, J=7 Hz, 2H), 2.07 (s, 2H), 2.12 (s, 3H), 2.14 (s, 3H), 3.80 (t, J=7 Hz, 2H), 5.68 (s, 1H); MS (ESI) m/z 282 (M+H)$^+$. Anal calcd for $C_{16}H_{27}NOS$: C, 68.28; H, 9.67; N, 4.98. Found: C, 68.23; H, 9.85; N, 4.95.

Example 130

1-[(2Z)-2-[2-(5-chloro-2-methoxyphenyl)-2-oxoethylidene]-4,5-dimethyl-1,3-thiazol-3(2H)-yl]-3,3-dimethylbutan-2-one

Example 130A 3-(3,3-dimethyl-2-oxobutyl)-2.4.5-trimethylthiazol-3-ium bromide A mixture of 2,4,5-trimethylthiazole (640 mg, 5 mmol) and 1-bromo-3,3-dimethylbutan-2-one (1.8 g, 10 mmol) in anhydrous acetonitrile (20 mL) was stirred at 60° C. for 5 h. The mixture was then concentrated under reduced pressure, the residue was triturated with anhydrous ethyl ether and the solid was filtered and dried under reduced pressure to provide 1.4 g of the crude title compound.

Example 130B

1-[(2Z)-2-[2-(5-chloro-2-methoxyphenyl)-2-oxoethylidene]-4,5-dimethyl-1,3-thiazol-3(2H)-yl]-3,3-dimethylbutan-2-one The title compound was prepared as described in Example 1B by replacing Example 1A with Example 130A. $^1$H NMR (300 MHz, DMSO-$d_6$) δ 1.23 (s, 9H), 2.00 (s, 3H), 2.17 (s, 3H), 3.79 (s, 3H), 5.18 (s, 2H), 6.27 (s, 1H), 7.07 (d, J=9 Hz, 1H), 7.38 (dd, J=9 Hz, 3 Hz, 1H), 7.41 (d, J=3 Hz, 1H); MS (ESI) m/z 394 (M+H)$^+$. Anal calcd for $C_{20}H_{24}ClNO_3S$: C, 60.98; H, 6.14; N, 3.56. Found: C, 60.70; H, 6.06; N, 3.55.

Example 131

(2Z)-2-[3-butyl-5-(4-fluorophenyl)-4-methyl-1,3-thiazol-2(3H)-ylidene]-1-(5-chloro-2-methoxyphenyl)ethanone A mixture of the product from Example 13 (126 mg, 0.3 mmol), 4-fluorophenylboronic acid (45 mg, 0.3 mmol0, triphenylphosphine (79 mg, 0.3 mmol), potassium carbonate (69 mg, 0.5 mmol) and Pd(Ph$_3$P)$_4$ (35 mg, 0.03 mmol) in dioxane (10 mL) was refluxed at 80° C. for 48 min. The mixture was then cooled to room temperature and concentrated under reduced pressure. The residue was purified by chromatography (hexane-EtOAc 2:1) to afford 50 mg of the title compound. $^1$H NMR (300 MHz, DMSO-$d_6$) δ 0.95 (t, J=7 Hz, 3H), 1.44 (sextet, J=7 Hz, 2H), 1.74 (quintet, J=7 Hz, 2H), 2.32 (s, 3H), 3.87 (s, 3H), 4.02 (t, J=7 Hz, 2H), 6.68 (s, 1H), 7.13 (d, J=9 Hz, 1H), 7.33 (t, J=9 Hz, 2H), 7.47 (m, 3H), 7.66 (d, J=3 Hz, 1H); MS (ESI) m/z 432 (M+H)$^+$. Anal calcd for $C_{23}H_{23}ClFNO_2S.0.25H_2O$: C, 63.29; H, 5.43; N, 3.21. Found: C, 63.20; H, 5.25; N, 3.04.

Example 132

1-adamantyl (2Z)-(3-butyl-4,5-dimethyl-1,3-thiazol-2(3H)-ylidene)acetate

The title compound was prepared as described in Example 1B by replacing 5-chloro-2-methoxy-benzoyl chloride with 1-adamantane-fluoroformate. $^1$H NMR (300 MHz, DMSO-$d_6$) δ 0.90 (t, J=7 Hz, 3H), 1.31 (sextet, J=7 Hz, 2H), 1.51 (m, 2H), 1.60 (s, 6H), 2.05 (m, 15H), 3.66 (t, J=7 Hz, 2H), 4.87 (s, 1H); MS (ESI) m/z 362 (M+H)$^+$. Anal calcd for $C_{21}H_{31}NO_2S$: C, 69.76; H, 8.64; N, 3.87. Found: C, 69.65; H, 8.83; N, 3.69.

Example 133

(2Z)-2-[3-butyl-5-(3-hydroxy-3-methylbut-1-ynyl)-4-methyl-1,3-thiazol-2(3H)-ylidene]-1-(5-chloro-2-methoxyphenyl)ethanone A mixture of product from Example 13 (33 mg, 0.08 mmol), 2-methylbut-3-yn-2-ol (10 mg, 0.1 mmol), CuI (2 mg, 0.01 mmol and Pd(Ph$_3$P)$_4$ (30 mg, 0.03 mmol) in triethylamine (10 mL) was heated at 100° C. for 1 hour. The mixture was then cooled to room temperature and concentrated under reduced pressure. The residue was purified by chromatography (hexane-EtOAc 1:1) to afford 20 mg of the title compound. $^1$H NMR (300 MHz, DMSO-$d_6$) δ 0.95 (t, J=7 Hz, 3H), 1.40 (sextet, J=7 Hz, 2H), 1.67 (quintet, J=7 Hz, 2H), 2.34 (s, 3H), 3.85 (s, 3H), 3.95 (t, J=7 Hz, 2H), 5.50 (s, 1H), 6.72 (s, 1H), 7.13 (d, J=9 Hz, 1H), 7.43 (dd, J=9 Hz, 3 Hz, 1H), 7.66 (d, J=3 Hz, 1H); MS (ESI) m/z 420 (M+H)$^+$. Anal calcd for $C_{22}H_{26}ClNO_3S$: C, 62.92; H, 6.24; N, 3.34. Found: C, 62.85; H, 6.28; N, 2.92.

Example 134

(1Z)-1-[3-(3,3-dimethyl-2-oxobutyl)-4,5-dimethyl-1,3-thiazol-2(3H)-ylidene]-4,4-dimethylpentan-2-one The title compound was prepared as described in Example 1B by replacing 5-chloro-2-methoxy-benzoyl chloride with 3,3-dimethylbutanoyl chloride and Example 1A with Example 130A. $^1$H NMR (300 MHz, DMSO-$d_6$) δ 0.90 (s, 9H), 1.22 (s, 9H), 1.92 (s, 2H), 2.07 (s, 3H), 2.09 (s, 3H), 5.04 (s, 2H), 5.45 (s, 1H); MS (ESI) m/z 324 (M+H)$^+$. Anal calcd for $C_{18}H_{29}NO_2S$: C, 66.83; H, 9.04; N, 4.33. Found: C, 66.80; H, 9.07; N, 4.14.

Example 135

(2E)-2-(3-butyl-4,5-dimethyl-1,3-thiazol-2(3H)-ylidene)-1-(5-chloro-2-methoxyphenyl-2-fluoroethanone A mixture of product from Example 1 (176 mg, 0.5 mmol) and SelectFluor™ (180 mg, 0.5 mmol) in acetonitrile (20 mL) was refluxed at 80° C. for 1 h. The mixture was then concentrated under reduced pressure and the residue was chromatographed (hexane-EtOAc 1:1) to afford 40 mg of the title compound. $^1$H NMR (300 MHz, DMSO-$d_6$) δ 0.90 (t, J=7 Hz, 3H), 1.29 (sextet, J=7 Hz, 2H), 1.60 (quintet, J=7 Hz, 2H), 2.13 (s, 3H), 2.18 (s, 3H), 3.76 (s, 3H), 4.04 (t, J=7 Hz, 2H), 6.68 (s, 1H), 7.08 (d, J=9 Hz, 1H), 7.20 (d, J=3 Hz, 1H), 7.41 (dd, J=9 Hz, 3 Hz, 1H); MS (ESI) m/z 370 (M+H)$^+$. Anal calcd for $C_{18}H_{21}ClFNO_2S.0.25H_2O$: C, 57.89; H, 5.78; N, 3.75. Found: C, 57.95; H, 5.15; N, 3.55.

Example 136

2-[(2Z)-2-[2-(5-chloro-2-methoxyphenyl)-2-oxoethylidene]-4,5-dimethyl-1,3-thiazol-3(2H)-yl]ethyl 5-chloro-2-methoxybenzoate The title compound was obtained as a side product of Example 5. $^1$H NMR (300 MHz, DMSO-$d_6$) δ 2.15 (s, 3H), 2.20 (s, 3H), 3.73 (s, 3H), 3.80 (s, 3H), 4.34 (t, J=5 Hz, 2H), 4.55 (t, J=5 Hz, 2H), 6.58 (s, 1H), 7.05 (d, J=9 Hz, 1H), 7.15 (d, J=9 Hz, 1H), 7.38 (dd, J=9 Hz, 3 Hz, 1H), 7.55 (m, 3H); MS (DCI/NH$_3$) m/z 508 (M+H)$^+$. Anal calcd for $C_{24}H_{23}Cl_2NO_5S$: C, 56.70; H, 4.56; N, 2.75. Found: C, 56.87; H, 4.45; N, 2.68.

Example 137

(2Z)-2-(3-butyl-4,5-dimethyl-1,3-thiazol-2(3H)-ylidene)-1-[2-(methylamino)phenyl]ethanone A mixture of 1-methyl-1H-benzo[d][1,3]oxazine-2,3-dione (177 mg, 1 mmol), Example 1A (311 mg, 1 mmol) and DMAP (500 mg, 4 mmol) in CH$_2$Cl$_2$ (25 mL) was stirred at ambient temperature for 24 h. The product was then purified by column chromatography (EtOAc as eluent) to afford 105 mg of the title compound. $^1$H NMR (300 MHz, DMSO-$d_6$) δ 0.94 (t, J=7 Hz, 3H), 1.37 (sextet, J=7 Hz, 2H), 1.62 (quintet, J=7 Hz, 2H), 2.13 (s, 3H), 2.18 (s, 3H), 2.79 (d, J=5 Hz, 3H), 3.98 (t, J=7 Hz, 2H), 6.40 (s, 1H), 6.57 (m, 2H), 7.20 (m, 1H), 7.70 (dd, J=9 Hz, 3 Hz, 1H), 8.46 (q, J=5 Hz, 1H); MS (DCI/NH$_3$) m/z 315 (M+H)$^+$. Anal calcd for $C_{18}H_{24}N_2OS$: C, 68.32; H, 7.64; N, 8.85. Found: C, 68.20; H, 7.51; N, 8.54.

Example 138

(2Z)-1-(5-chloro-2-methoxyphenyl)-2-[3-(4-fluorobutyl)-4,5-dimethyl-1,3-thiazol-2(3H)-ylidene]ethanone Example 138A 3-(4-fluorobutyl)-2,4,5-trimethyl-1,3-thiazol-3-ium iodide The title compound was prepared as described in Example 1A by replacing 1-iodobutane with 4-fluoro-1-iodobutane.

Example 138B (2Z)-1-(5-chloro-2-methoxyphenyl)-2-[3-(4-fluorobutyl)-4,5-dimethyl-1,3-thiazol-2(3H)-ylidene]ethanone The title compound was prepared as described in Example 1B by replacing Example 1A with Example 138A. $^1$H NMR (300 MHz, DMSO-$d_6$) δ 1.67 (m, 4H), 2.15 (s, 3H), 2.20 (s, 3H), 3.85 (s, 3H), 3.97 (t, J=7 Hz, 2H), 4.43 (t, J=6 Hz, 1H), 4.60 (t, J=6 Hz, 1H), 6.54 (s, 1H), 7.10 (d, J=9 Hz, 1H), 7.39 (dd, J=9 Hz, 3 Hz, 1H), 7.63 (d, J=3 Hz, 1H); MS (ESI) m/z 370 (M+H)$^+$. Anal calcd for $C_{18}H_{21}ClFNO_2S$: C, 58.45; H, 5.72; N, 3.79. Found: C, 59.07; H, 5.50; N, 3.57.

Example 139

(2Z)-1-(2-amino-5-chlorophenyl)-2-(3-butyl-4,5-dimethyl-1,3-thiazol-2(3H)-ylidene)ethanone The title compound was prepared as described in Example 137 by replacing 1-methyl-1H-benzo[d][1,3]oxazine-2,3-dione with 6-chloro-1H-benzo[d][1,3]oxazine-2,3-dione. $^1$H NMR (300 MHz, DMSO-$d_6$) δ 0.94 (t, J=7 Hz, 3H), 1.37 (sextet, J=7 Hz, 2H), 1.62 (quintet, J=7 Hz, 2H), 2.13 (s, 3H), 2.18 (s, 3H), 4.02 (t, J=7 Hz, 2H), 6.38 (s, 1H), 6.63 (d, J=9 Hz, 2H), 6.75 (broad s, 2H), 7.07 (dd, J=9 Hz, 3 Hz, 1H), 7.62 (d, J=3 Hz, 1H); MS (DCI/NH$_3$) m/z 337 (M+H)$^+$.

Example 140 ethyl 2-[(2Z)-2-(3-butyl-4,5-dimethyl-1,3-thiazol-2(3H)-ylidene)ethanoyl]-4-chlorophenylcarbamate To a solution of Example 139 (17 mg, 0.05 mmol) and NaHCO$_3$ (42 mg, 0.5 mmol) in EtOAc (5 mL) and H$_2$O (5 mL) was added dropwise at room temperature a solution of ethyl chloroformate (0.06 mL, 0.06 mmol) in EtOAc (3 mL) and the reaction was continued for the next 4 h. The ethyl acetate layer was separated, washed with brine, dried with anhydrous MgSO$_4$ and concentrated under reduced pressure. The residue was chromatographed (EtOAc as eluent) to afford 20 mg of the title compound. $^1$H NMR (300 MHz, DMSO-$d_6$) δ 0.94 (t, J=7 Hz, 3H), 1.24 (t, J=7 Hz, 3H), 1.37 (sextet, J=7 Hz, 2H), 1.62 (quintet, J=7 Hz, 2H), 2.10 (s, 3H), 2.14 (s, 3H), 4.13 (m, 4H), 6.56 (s, 1H), 7.42 (dd, J=9 Hz, 3 Hz, 1H), 7.96 (d, J=3 Hz, 1H 8.23 (d, J=9 Hz, 1H), 11.98 (s, 1H); MS (DCI/NH$_3$) m/z 409 (M+H)$^+$. Anal calcd for $C_{20}H_{25}ClN_2O_3S$: C, 58.74; H, 6.16; N, 6.85. Found: C, 59.02; H, 5.98; N, 6.31.

Example 141

(2E)-2-(3-butyl-4,5-dimethyl-1,3-thiazol-2(3H)-ylidene)-1-(2-chloropyridin-3-yl)-2-fluoroethanone The title compound was prepared as described in Example 135 by replacing Example 1 with Example 105. $^1$H NMR (300 MHz, DMSO-$d_6$) δ 0.90 (t, J=7 Hz, 3H), 1.29 (sextet, J=7 Hz, 2H), 1.60 (quintet, J=7 Hz, 2H), 2.13 (s, 3H), 2.18 (s, 3H), 4.10 (t, J=7 Hz, 2H), 6.68 (s, 1H), 7.30 (dd, J=9 Hz, 5 Hz, 1H), 7.81 (dd, J=9 Hz, 3 Hz, 1H), 8.40 (dd, J=5 Hz, 3 Hz, 1H); MS (DCI/NH$_3$) m/z 341 (M+H)$^+$.

Example 142 ethyl 2-[(2Z)-2-(3-butyl-4,5-dimethyl-1,3-thiazol-2(3H)-ylidene)ethanoyl]-4-chlorophenyl(methyl)carbamate A mixture of product from Example 140 (100 mg, 0.24 mmol) and 60% oil suspension NaH (40 mg, 0.6 mmol) in anhydrous THF (20 mL) was treated with iodomethane (0.5 mL) at 50° C. for 5 h and at room temperature for 10 h. The THF was removed under reduced pressure, the residue was partitioned between water and EtOAc. The ethyl acetate layer was separated, washed with brine, dried with anhydrous MgSO$_4$ and concentrated under reduced pressure. The residue was chromatographed (hexane-EtOAc 1:1 as eluent) to provide 91 mg of the title compound. $^1$H NMR (300 MHz, DMSO-d$_6$) δ 0.92 (m, 6H), 1.35 (sextet, J=7 Hz, 2H), 1.62 (m, 2H), 2.13 (s, 3H), 2.19 (s, 3H), 3.15 (s, 3H), 3.85 (m, 4H), 5.96 (s, 1H), 7.31 (d, J=9 Hz, 1H), 7.45 (dd, J=9 Hz, 3 Hz, 1H), 7.58 (d, J=3 Hz, 2H); MS (DCI/NH$_3$) m/z 423 (M+H)$^+$. Anal calcd for C$_{21}$H$_{27}$ClN$_2$O$_3$S.0.1H$_2$O: C, 59.36; H, 6.45; N, 6.59. Found: C, 59.14; H, 6.43; N, 6.35.

Example 143

Methyl 2-[(2Z)-2-(3-butyl-4,5-dimethyl-1,3-thiazol-2(3H)-ylidene)ethanoyl]-4-chlorobenzoate The title compound was prepared as described in Example 1B by replacing 5-chloro-2-methoxy-benzoyl chloride with methyl 4-chloro-2-(chlorocarbonyl)benzoate. $^1$H NMR (300 MHz, DMSO-d$_6$) δ 0.93 (t, J=7 Hz, 3H), 1.38 (sextet, J=7 Hz, 2H), 1.62 (quintet, J=7 Hz, 2H), 2.15 (s, 3H), 2.20 (s, 3H), 3.69 (s, 3H), 3.99 (t, J=7 Hz, 2H), 6.25 (s, 1H), 7.51 (m, 1H), 7.60 (dd, J=9 Hz, 3 Hz, 1H), 7.80 (d, J=9 Hz, 1H); MS (DCI/NH$_3$) m/z 380 (M+H)$^+$. Anal calcd for C$_{19}$H$_{22}$ClN$_2$O$_3$S: C, 60.07; H, 5.84; N, 3.69. Found: C, 59.96; H, 5.84; N, 3.59.

Example 144

(2Z)-2-[3-butyl-4-methyl-5-(2-methyl-1,3-dioxolan-2-yl)-1,3-thiazol-2(3H)-ylidene]-1-(5-chloro-2-methoxyphenyl)ethanone

Example 144A

2,4-dimethyl-5-(2-methyl-1,3-dioxolan-2-yl)thiazole

To a solution of 5-acetyl-2-4-dimethyl thiazole (775 mg, 5 mmol) in toluene (20 mL) was added ethylene glycol (3.1 g, 50 mmol) and p-toluenesulfonic acid monohydrate (19 mg, 0.1 mmol) and refluxed overnight. After cooling, a saturated solution of sodium bicarbonate (10 mL) and ethyl acetate were added. The aqueous layer was extracted with ethyl acetate (3×10 mL). The organics were combined, washed with brine, dried with sodium sulfate and concentrated. The residue was purified by chromatography over silica gel (hexane-EtOAc 4:1 as eluent) to provide the title compound. $^1$H NMR (300 MHz, CDCl$_3$) δ ppm 1.72 (s, 3 H) 2.42 (s, 3 H) 2.60 (s, 3 H) 3.87-3.92 (m, 2 H) 4.02-4.07 (m, 2 H). MS (DCI) m/z 200 (M+H)$^+$.

Example 144B

3-butyl-2,4-dimethyl-5-(2-methyl-1,3-dioxolan-2-yl)thiazol-3-ium iodide

The title compound was prepared as described in Example 1A, replacing 2,4,5-trimethylthiazole with Example 144A. The thiazolium salt was carried on to the next step without purification. $^1$H NMR (300 MHz, DMSO-d$_6$) δ ppm 0.95 (t, J=7.34 Hz, 3 H) 1.41 (dd, J=15.07, 7.54 Hz, 2 H) 1.65-1.77 (m, 5 H) 2.64 (s, 3 H) 2.98 (s, 3 H) 3.80-3.94 (m, 2 H) 4.04-4.16 (m, 2 H) 4.25-4.37 (m, 2 H). MS (DCI) m/z 256 (M).

Example 144C

(2Z)-2-[3-butyl-4-methyl-5-(2-methyl-1,3-dioxolan-2-yl)-1,3-thiazol-2(3H)-ylidene]-1-(5-chloro-2-methoxyphenyl)ethanone The title compound was prepared as described in Example 1B, replacing Example 1A with Example 144B. $^1$H NMR (300 MHz, DMSO-d$_6$) δ ppm 0.95 (t, J=7.29 Hz, 3 H) 1.33-1.46 (m, 2 H) 1.59-1.72 (m, 5 H) 2.32 (s, 3 H) 3.80-3.92 (m, 7 H) 3.96-4.06 (m, 2 H) 6.52 (s, 1 H) 7.11 (d, J=8.82 Hz, 1 H) 7.40 (dd, J=8.82, 2.71 Hz, 1 H) 7.62 (d, J=2.71 Hz, 1 H). MS (DCI) m/z 424 (M+H)$^+$. Anal calcd for C$_{21}$H$_{26}$ClNO$_4$S: C, 59.49; H, 6.18; N, 3.30. Found: C, 59.12; H, 6.03; N, 3.32.

Example 145

2,2,2-trichloro-1,1-dimethylethyl (2Z)-(3-butyl-4,5-dimethyl-1,3-thiazol-2(3H)-ylidene)acetate The title compound was prepared as described in Example 1B, replacing 5-chloro-2-methoxy-benzoyl chloride with 2,2,2-trichloro-1,1-dimethylethyl chloroformate. $^1$H NMR (300 MHz, DMSO-d$_6$) δ ppm 0.91 (t, J=7.29 Hz, 3 H) 1.25-1.39 (m, 2 H) 1.49-1.60 (m, 2 H) 1.81-1.93 (s, 6 H) 2.09 (m, 6 H) 3.63-3.77 (m, 2 H) 4.95 (s, 1 H). MS (DCI) m/z 386 (M+H)$^+$.

Example 146

2,2,2-trichloro-1,1-dimethylethyl (2Z)-(3-butyl-5-methyl-1,3,4-thiadiazol-2(3H)-ylidene)acetate The title compound was prepared as described in Example 1B, replacing Example 1A with Example 47A and replacing 5-chloro-2-methoxy-benzoyl chloride with 2,2,2-trichloro-1,1-dimethylethyl chloroformate. $^1$H NMR (300 MHz, DMSO-d$_6$) δ ppm 0.83-0.93 (m, 3 H) 1.24-1.37 (m, 2 H) 1.59-1.71 (m, 2 H) 1.86 (s, 6 H) 2.40 (s, 3 H) 3.94 (t, J=7.12 Hz, 2 H) 5.08 (s, 1 H). MS (DCI) m/z 373 (M+H)$^+$.

Example 147

(2Z)-2-[4-tert-butyl-3-(2-methoxyethyl)-1,3-thiazol-2(3H)-ylidene]-1-(5-chloro-2-methoxyphenyl)ethanone The title compound was prepared and purified as described in Example 16, substituting 2-methoxyethylisothiocyanate for n-butylisothiocyanate and substituting 1-bromopinacolone for 3-chloropentan-2,4-dione. $^1$H NMR (300 MHz, DMSO-d$_6$) δ ppm 1.38 (s, 9 H) 3.31 (s, 3 H) 3.71 (t, J=6.78 Hz, 2 H) 3.87 (s, 3 H) 4.33 (t, J=6.78 Hz, 2 H) 6.50 (s, 1 H) 6.61 (s, 1 H) 7.12 (d, J=9.15 Hz, 1 H) 7.41 (dd, J=8.81, 2.71 Hz, 1 H) 7.63 (d, J=3.05 Hz, 1 H). MS (DCI) m/z 382 (M+H)$^+$. Anal calcd for C$_{19}$H$_{24}$ClNO$_3$S.0.8H$_2$O: C, 58.11; H, 6.47; N, 3.57. Found: C, 57.95; H, 6.49; N, 3.97

Example 148

(2Z)-2-[4-tert-butyl-3-(tetrahydrofuran-2-ylmethyl)-1,3-thiazol-2(3H)-ylidene]-1-(5-chloro-2-methoxyphenyl)ethanone The title compound was prepared and purified as described in Example 16, substituting 2-isothiocyanatomethyltetrahydrofuran for n-butyl isothiocyanate and substituting 1-bromopinacolone for 3-chloropentan-2,4-dione. $^1$H NMR (300

MHz, DMSO-$d_6$) δ ppm 1.37 (s, 9 H) 1.68-1.78 (m, 1 H) 1.81-1.95 (m, 2 H) 2.04-2.15 (m, 1 H) 3.56-3.66 (m, 1 H) 3.71-3.80 (m, 1 H) 3.84-3.87 (s, 3 H) 4.15-4.23 (m, 1 H) 4.31-4.46 (m, 2 H) 6.49 (s, 1 H) 6.58 (s, 1 H) 7.12 (d, J=8.82 Hz, 1 H) 7.40 (dd, J=8.82, 2.71 Hz, 1 H) 7.62 (d, J=3.05 Hz, 1 H). MS (DCI) m/z 408 (M+H)$^+$. Anal calcd for $C_{21}H_{26}ClNO_3S.0.8H_2O$: C, 59.72; H, 6.59; N, 3.32. Found: C, 59.85; H, 6.45; N, 3.45.

Example 149

(2Z)-2-[4-tert-butyl-3-(2-piperidin-1-ylethyl)-1,3-thiazol-2(3H)-ylidene]-1-(5-chloro-2-methoxyphenyl)ethanone The title compound was prepared and purified as described in Example 16, substituting 2-piperidinoethyl isothiocyanate for butyl isothiocyanate and substituting 1-bromopinacolone for 3-chloropentan-2,4-dione. $^1$H NMR (300 MHz, DMSO-$d_6$) δ ppm 1.38 (s, 9 H) 1.43-1.57 (m, 6 H) 2.46 (m, 4 H) 2.57-2.72 (m, 2 H) 3.88 (s, 3 H) 4.20-4.33 (m, 2 H) 6.51 (s, 1 H) 6.66 (s, 1 H) 7.13 (d, J=9.16 Hz, 1 H) 7.42 (dd, J=8.82, 2.71 Hz, 1 H) 7.67 (d, J=3.05 Hz, 1 H). MS (DCI) m/z 435 (M+H)$^+$. Anal calcd for $C_{23}H_{31}ClN_2O_2S.1.2H_2O$: C, 60.50; H, 7.37; N, 6.13. Found: C, 60.24; H, 7.07; N, 6.13.

Example 150

(2Z)-3-butyl-2-[2-(5-chloro-2-methoxyphenyl)-2-oxoethylidene]-N-methyl-2,3-dihydro-1,3-thiazole-4-carboxamide To a solution of Example 45 in methanol was added a solution of methylamine in methanol and stirred overnight. The title compound was obtained by concentration of the reaction solution. $^1$H NMR (300 MHz, DMSO-D6) δ ppm 0.92 (t, J=7.29 Hz, 3 H) 1.23-1.37 (m, 2 H) 1.71 (m, 2 H) 2.74 (d, J=4.75 Hz, 4 H) 3.87 (s, 3 H) 4.15-4.24 (m, 2 H) 6.66 (s, 1 H) 7.14 (d, J=8.81 Hz, 1 H) 7.21 (s, 1 H) 7.44 (dd, J=8.82, 2.71 Hz, 1 H) 7.66 (d, J=2.71 Hz, 1 H) 8.77 (d, J=4.75 Hz, 1 H). MS (DCI) m/z 381 (M+H)$^+$. Anal calcd for $C_{18}H_{21}ClN_2O_3S.1.2H_2O.0.3 NH_4OH$: C, 52.81; H, 6.03; N, 7.87. Found: C, 52.52; H, 5.70; N, 7.81.

Example 151

(Z)-2-(5-acetyl-3-butylthiazol-2(3H)-ylidene)-1-(5-chloro-2-methoxyphenyl)ethanone Example 151A sodium (Z)-4-oxopent-2-en-2-olate To a stirred suspension of sodium methoxide (27 g, 0.5 mol) in ether (320 mL) was added a mixture of acetone (29 g, 0.5 mol) and ethyl formate (37 g, 0.5 mmol) dropwise. The reaction was stirred for 30 min before the solid was filtered and dried in vacuo. The solid was ground up using a mortar and pestle and used without further purification. $^1$H NMR (300 MHz, $D_2O$) δ ppm 2.15 (s, 3 H) 5.24 (s, 1 H) 8.97 (d, J=10.51 Hz, 1 H).

Example 151B 3-bromo-4-hydroxypent-3-en-2-one

To a stirred suspension of Example 151A (34.1 g, 0.32 mol) in dichloromethane (250 mL) at −78° C. was added dropwise bromine (50.5 g, 0.32 mmol). The reaction was stirred for another 2 hrs before it was brought to room temperature. The solid was filtered and washed with dichloromethane. The filtrate was concentrated at room temperature to one-fourth the volume and the solid was filtered to give the title compound. $^1$H NMR (300 MHz, DMSO-$d_6$) δ ppm 2.32 (s, 3 H) 8.32 (b, 1 H) 12.1 (b, 1 H).

Example 151C (Z)-2-(5-acetyl-3-butylthiazol-2(3H)-ylidene)-1-(5-chloro-2-methoxyphenyl)ethanone The title compound was prepared and purified as described in Example 16, replacing 3-chloropentane-2,4-dione with Example 151B. $^1$H NMR (300 MHz, CDCl$_3$) δ ppm 1.02 (t, J=7.46 Hz, 3 H) 1.44 (dd, J=15.26, 7.46 Hz, 2 H) 1.81-1.91 (m, 2 H) 2.44 (s, 3 H) 3.88 (s, 3 H) 3.94 (t, J=7.29 Hz, 2 H) 6.70 (s, 1 H) 6.89 (d, J=8.82 Hz, 1 H) 7.32 (dd, J=8.82, 2.71 Hz, 1 H) 7.55 (s, 1 H) 7.87 (d, J=2.71 Hz, 1 H). MS (DCI) m/z 366 (M+H)$^+$. Anal calcd for $C_{18}H_{20}ClNO_3S$: C, 59.09; H, 5.51; N, 3.83. Found: C, 58.81; H, 5.46; N, 3.80.

Example 152

6-[(2Z)-2-(3-butyl-5-tert-butyl-1,3,4-thiadiazol-2(3H)-ylidene)ethanoyl]-2,2-dimethyl-2,3-dihydro-4H-pyran-4-one The procedure in Example 47B was followed, replacing 2-methoxy-5-chloro benzoic acid with 2,2-dimethyl-4-oxo-3,4-dihydro-2H-pyran-6-carboxylic acid and replacing Example 47A with Example 50C to afford the title compound. $^1$H NMR (300 MHz, CDCl$_3$) δ ppm 1.00 (t, J=7.29 Hz, 3H) 1.40 (m, 11H) 1.51 (s, 6H) 1.86 (m, 2H) 2.54 (s, 2H) 4.14 (t, J=7.12 Hz, 2H) 6.26 (s, 1H) 6.32 (s, 1H). MS (DCI) m/z 365 (M+H)$^+$.

Example 153

(2Z)-2-(3-butyl-5-tert-butyl-1,3-thiazol-2(3H)-ylidene)-1-(2-chloropyridin-3-yl)ethanone Example 153A 5-acetyl-2-methylthiazole To a solution of the product of Example 151B (14.5 g, 88 mmol) in acetone (220 mL) was added thioacetamide (6.6 g, 88 mmol) and stirred overnight. The solid was filtered to give the title compound as the hydrogen bromide salt. $^1$H NMR (300 MHz, DMSO-$d_6$) δ ppm 2.54 (s, 3 H) 2.71 (s, 3 H) 8.46 (s, 1 H). MS (DCI) m/z 142 (M+H)$^+$.

Example 153B 5-tert-butyl-2-methylthiazole

The title compound was prepared and purified as described in Example 35A, replacing 5-acetyl-2,4-dimethyl thiazole with Example 153A. $^1$H NMR (300 MHz, DMSO-$d_6$) δ ppm 1.31 (s, 9 H) 2.57 (s, 3 H) 7.33 (s, 1 H). MS (DCI) m/z 156 (M+H)$^+$.

Example 153C 3-butyl-5-tert-butyl-2-methyl-1,3-thiazol-3-ium iodide

The title compound was prepared and purified as described in Example 1A, replacing 2,4,5-trimethyl thiazole with Example 153B. The compound was used without further purification.

Example 153D (2Z)-2-(3-butyl-5-tert-butyl-1,3-thiazol-2(3H)-ylidene)-1-(2-chloropyridin-3-yl)ethanone The title compound was prepared and purified as described in Example 35C, replacing Example 35B with Example 153C and replacing 3-chlorothiophene-2-carbonyl chloride with 2-chloronicotinoyl chloride. $^1$H NMR (300 MHz, CDCl$_3$) δ ppm 0.98 (t, J=7.29 Hz, 3 H) 1.34-1.37 (m, 9 H) 1.38-1.46 (m, 2 H) 1.75-1.85 (m, 2 H) 3.82-3.90 (m, 2 H) 6.18 (s, 1 H) 6.56 (s, 1 H) 7.29 (dd, J=7.46, 4.75 Hz, 1 H) 8.03 (dd, J=7.80, 2.03 Hz, 1 H) 8.38 (dd, J=4.75, 2.03 Hz, 1 H). MS (ESI) m/z 351 (M+H)$^+$. Anal calcd for C$_{18}$H$_{23}$ClN$_2$OS: C, 61.61; H, 6.61; N, 7.98. Found: C, 61.46; H, 6.91; N, 7.88.

Example 154

(2Z)-2-(3-butyl-5-tert-butyl-1,3-thiazol-2(3H)-ylidene)-1-(5-fluoro-2-methoxyphenyl)ethanone The title compound was prepared and purified as described in Example 35C, replacing Example 35B with Example 153C and replacing 3-chlorothiophene-2-carbonyl chloride with 5-fluoro-2-methoxybenzoyl chloride. $^1$H NMR (300 MHz, CDCl$_3$) δ ppm 1.00 (t, J=7.29 Hz, 3 H) 1.34 (s, 9 H) 1.41-1.46 (m, 2 H) 1.76-1.86 (m, 2 H) 3.83-3.88 (m, 5 H) 6.51 (s, 1 H) 6.54 (s, 1 H) 6.85-6.90 (m, 1 H) 6.98-7.05 (m, 1 H) 7.66 (dd, J=9.49, 3.39 Hz, 1 H). MS (ESI) m/z 364 (M+H).

Example 155

(2Z)-2-(3-butyl-5-tert-butyl-1,3-thiazol-2(3H)-ylidene)-1-(3-chlorothien-2-yl)ethanone The title compound was prepared and purified as described in Example 35C, replacing Example 35B with Example 153C. $^1$H NMR (300 MHz, CDCl$_3$) δ ppm 1.00 (t, J=7.46 Hz, 3 H) 1.34 (s, 9 H) 1.42 (m, 2 H) 1.79-1.89 (m, 2 H) 3.87-3.93 (m, 2 H) 6.55 (s, 1 H) 6.72 (s, 1 H) 6.91-6.97 (m, 1 H) 7.35 (d, J=5.09 Hz, 1 H). MS (ESI) m/z 356 (M+H)$^+$. Anal calcd for C$_{17}$H$_{22}$ClNOS$_2$: C, 57.36; H, 6.23; N, 3.94. Found: C, 57.10; H, 6.11; N, 3.82.

Example 156

6-[(2Z)-2-(3-butyl-5-tert-butyl-1,3-thiazol-2(3H)-ylidene)ethanoyl]-2,2-dimethyl-2,3-dihydro-4H-pyran-4-one The title compound was prepared and purified as described in Example 35C, replacing Example 35B with Example 153C and replacing 3-chlorothiophene-2-carbonyl chloride with 2,2-dimethyl-4-oxo-3,4-dihydro-2H-pyran-6-carbonyl chloride. $^1$H NMR (300 MHz, CDCl$_3$) δ ppm 1.02 (t, J=7.29 Hz, 3 H) 1.34 (s, 9 H) 1.37-1.46 (m, 2 H) 1.48-1.52 (m, 6 H) 1.76-1.86 (m, 2 H) 2.53 (s, 2 H) 3.88-3.95 (m, 2 H) 6.28 (s, 1 H) 6.33 (s, 1 H) 6.60 (s, 1 H). MS (ESI) m/z 364 (M+H)$^+$. Anal calcd for C$_{20}$H$_{29}$NO$_3$S.0.06 CH$_2$Cl$_2$: C, 65.36; H, 7.96; N, 3.80. Found: C, 65.67; H, 7.56; N, 3.69.

Example 157

(2Z)-2-(3-butyl-5-tert-butyl-1,3-thiazol-2(3H)-ylidene)-1-(5-iodo-2-methoxyphenyl)ethanone The title compound was prepared and purified as described in Example 35C, replacing Example 35B with Example 153C and replacing 3-chlorothiophene-2-carbonyl chloride with 5-iodo-2-methoxybenzoyl chloride. $^1$H NMR (300 MHz, CDCl$_3$) δ ppm 0.99 (t, J=7.46 Hz, 3 H) 1.35 (s, 9 H) 1.40 (m, 2 H) 1.75-1.85 (m, 2 H) 3.82-3.91 (m, 5 H) 6.57 (s, 1 H) 6.70 (d, J=8.82 Hz, 1 H) 7.60 (dd, J=8.48, 2.37 Hz, 1 H) 8.10 (d, J=2.37 Hz, 1 H). MS (ESI) m/z 472 (M+H)$^+$.

Example 158

(2Z)-1-(1-benzofuran-5-yl)-2-(3-butyl-5-tert-butyl-1,3-thiazol-2(3H)-ylidene)ethanone The title compound was prepared and purified as described in Example 35C, replacing Example 35B with Example 153C and replacing 3-chlorothiophene-2-carbonyl chloride with benzofuran-5-carbonyl chloride. $^1$H NMR (300 MHz, CDCl$_3$ ppm 0.98-1.04 (m, 3 H) 1.35-1.38 (m, 9 H) 1.39-1.50 (m, 2 H) 1.78-1.92 (m, 2 H) 3.92 (t, J=7.46 Hz, 2 H) 6.53 (s, 1 H) 6.84 (d, J=3.05 Hz, 1 H) 7.51 (d, J=8.48 Hz, 1 H) 7.64 (d, J=2.03 Hz, 1 H) 7.93 (dd, J=8.65, 1.86 Hz, 1 H) 8.22 (d, J=1.36 Hz, 1 H). MS (ESI) m/z 356 (M+H)$^+$.

Example 159

(2Z)-2-(3-butyl-5-tert-butyl-1,3-thiazol-2(3H)-ylidene)-1-(2-ethoxypyridin-3-yl)ethanone The title compound was prepared and purified as described in Example 35C, replacing Example 35B with Example 153C and replacing 3-chlorothiophene-2-carbonyl chloride with 2-ethoxynicotinoyl chloride. $^1$H NMR (300 MHz, CDCl$_3$ ppm 1.00 (t, J=7.29 Hz, 3 H) 1.35 (s, 9 H) 1.37-1.45 (m, 2 H) 1.48 (t, J=7.12 Hz, 3 H) 1.76-1.89 (m, 2 H) 3.85-3.92 (m, 2 H) 4.49 (q, J=7.12 Hz, 2 H) 6.53 (s, 1 H) 6.98 (dd, J=7.46, 5.09 Hz, 1 H) 8.16 (dd, J=5.09, 2.03 Hz, 1 H) 8.42 (dd, J=7.46, 2.03 Hz, 1 H). MS (ESI) m/z 361 (M+H)$^+$. Anal calcd for C$_{20}$H$_{28}$N$_2$O$_2$S.0.2 EtOH: C, 65.44; H, 8.26; N, 7.13. Found: C, 65.17; H, 8.53; N, 6.80.

Example 160

(2Z)-1-(1-benzofuran-5-yl)-2-(3-butyl-5-isopropenyl-1,3-thiazol-2(3H)-ylidene)ethanone This compound was isolated as a by-product from the procedure of Example 158. $^1$H NMR (300 MHz, CDCl$_3$) m 0.97-1.06 (m, 3 H) 1.41-1.50 (m, 2 H) 1.85 (m, 2 H) 2.07 (s, 3 H) 3.94 (t, J=7.29 Hz, 2 H) 5.02 (m, 1 H) 5.26-5.30 (m, 1 H) 6.74 (s, 1 H) 6.84 (s, 1 H) 7.50-7.55 (m, 1 H) 7.63-7.69 (m, 1 H) 7.96 (dd, J=8.65, 1.86 Hz, 1 H) 8.21-8.26 (m, 1 H). MS (ESI) m/z 340 (M+H).

Example 161

(2Z)-2-(3-butyl-5-isopropenyl-1,3-thiazol-2(3H)-ylidene)-1-(2-ethoxypyridin-3-yl)ethanone The title compound was isolated as a by-product from procedure of Example 159. $^1$H NMR (300 MHz, CDCl$_3$) δ ppm 1.00 (t, J=7.29 Hz, 3 H) 1.47 (qd, J=7.23, 3.05 Hz, 5 H) 1.81-1.89 (m, 2 H) 2.06 (s, 3 H) 3.91 (t, J=7.46 Hz, 2 H) 4.50 (qd, J=6.89, 4.07 Hz, 2 H) 5.02 (m, 1 H) 5.26 (m, 1 H) 6.76 (s, 1 H) 6.99 (ddd, J=7.63, 4.75, 3.22 Hz, 2 H) 8.18 (dd, J=4.75, 2.03 Hz, 1 H) 8.42 (dd, J=7.46, 2.03 Hz, 1 H). MS (ESI) m/z 345 (M+H)+.

Example 162

(2Z)-2-(3-butyl-4-methyl-1,3-thiazol-2(3H)-ylidene)-1-(2,4-dimethoxyphenyl)ethanone

Example 162A 3-butyl-2,4-dimethylthiazol-3-ium iodide

The title compound was prepared and purified as described in Example 1A, substituting 2,4-dimethylthiazole for 2,4,5-trimethyl thiazole. $^1$H NMR (300 MHz, DMSO-$d_6$) δ ppm 0.94 (t, J=7.29 Hz, 3 H) 1.41 (qd, J=7.52, 7.29 Hz, 2 H) 1.65-1.77 (m, 2 H) 2.54 (s, 3 H) 2.98 (s, 3 H) 4.26-4.35 (m, 2H) 7.80 (s, 1 H).

Example 162B (2Z)-2-(3-butyl-4-methyl-1,3-thiazol-2(3H)-ylidene)-1-(2,4-dimethoxyphenyl)ethanone The title compound was prepared as described in Example 1B, substituting Example 162A for Example 1A and 2,5-dimethoxybenzoyl chloride for 5-chloro-2-methoxybenzoyl chloride. $^1$H NMR (300 MHz, CDCl$_3$) δ ppm 1.02 (t, J=7.29 Hz, 3 H) 1.46 (m, 2 H) 1.80 (m, 2 H) 2.42 (s, 3 H) 3.86 (s, 3 H) 3.92 (s, 3 H) 4.14 (m, 2 H) 6.50 (m, J=2.37 Hz, 1 H) 6.61 (m, J=8.65, 2.54 Hz, 1 H) 6.72 (m, 1 H), 7.9 (m, 1 H). MS (DCI) m/z 334 (M+H)+.

Example 163

(2Z)-2-(3-butyl-4-methyl-1,3-thiazol-2(3H)-ylidene)-1-(2,5-diethoxyphenyl)ethanone The title compound was prepared as described in Example 1B, substituting Example 162A for Example 1A and 2,5-diethoxybenzoyl chloride for 5-chloro-2-methoxybenzoyl chloride. $^1$H NMR (300 MHz, CDCl$_3$) δ ppm 1.00 (t, J=7.29 Hz, 3 H) 1.35-1.48 (m, 8 H) 1.79 (m, 2 H) 2.36 (s, 3 H) 3.96-4.11 (m, 6 H) 6.47 (s, 1 H) 6.86-6.95 (m, 2 H) 7.46 (d, J=2.71 Hz, 1 H). MS (DCI) m/z 362 (M+H)+.

Example 164

(2Z)-2-[5-tert-butyl-3-(2-methoxyethyl)-1,3,4-thiadiazol-2(3H)-ylidene]-1-(5-chloro-2-methoxyphenyl)ethanone

Example 164A 5-tert-butyl-3-(2-methoxyethyl)-2-methyl-1,3,4-thiadiazol-3-ium bromide The title compound was prepared and purified as described in Example 47A, substituting 2-bromoethyl methyl ether for butyl iodide and Example 50B for 2,5-dimethyl thiadiazole. $^1$H NMR (300 MHz, DMSO-$d_6$) δ ppm 1.46 (s, 9 H) 3.08 (s, 3 H) 3.27 (s, 3 H) 3.81-3.85 (m, 2 H) 4.73-4.80 (m, 2 H). MS (DCI) m/z 215 (M)+.

Example 164B (2Z)-2-[5-tert-butyl-3-(2-methoxyethyl)-1,3,4-thiadiazol-2(3H)-ylidene]-1-(5-chloro-2-methoxyphenyl)ethanone The title compound was prepared and purified as described in Example 47B, substituting Example 164A for Example 47A. $^1$H NMR (300 MHz, CDCl$_3$) δ ppm 1.41 (s, 9H) 3.38 (s, 3 H) 3.80 (d, J=4.41 Hz, 2 H) 3.86 (s, 3 H) 4.27 (t, J=5.76 Hz, 2 H) 6.88 (d, J=8.81 Hz, 1 H) 7.31 (dd, J=8.82, 2.71 Hz, 1 H) 7.71-7.74 (m, 1 H). MS (ESI) m/z 383 (M+H)+. Anal calcd for C$_{18}$H$_{23}$ClN$_2$O$_3$S.0.2 MeOH.0.4 TFA: C, 52.47; H, 5.61; N, 6.44. Found: C, 52.52; H, 5.35; N, 6.08.

Example 165

(2Z)-2-[5-tert-butyl-3-(2-methoxyethyl)-1,3,4-thiadiazol-2(3H)-ylidene]-1-(2,3-dichlorophenyl)ethanone The title compound was prepared as described in Example 47B, substituting Example 164A for Example 47A and 2,3-dichlorobenzoic acid for 5-chloro-2-methoxybenzoic acid. $^1$H NMR (300 MHz, CDCl$_3$) δ ppm 1.42 (s, 9H) 3.36 (s, 3 H) 3.78 (t, J=5.76 Hz, 2 H) 4.24 (t, J=5.59 Hz, 2 H) 7.20-7.26 (m, 1 H) 7.43 (dd, J=7.80, 1.70 Hz, 1 H) 7.45-7.49 (m, 1 H). MS (DCI) m/z 387 (M+H)+. Anal calcd for C$_{17}$H$_{20}$Cl$_2$N$_2$O$_2$S.0.5 TFA: C, 48.60; H, 4.65; N, 6.30. Found: C, 48.56; H, 4.57; N, 6.47.

Example 166

(2Z)-2-(3-butyl-4-methyl-1,3-thiazol-2(3H)-ylidene)-1-[trans-2-phenylcyclopropyl]ethanone The title compound was prepared as described in Example 1B, substituting Example 162A for Example 1A and trans-2-phenyl-1-cyclopropanecarbonyl chloride for 5-chloro-2-methoxybenzoyl chloride. $^1$H NMR (300 MHz, CHLOROFORM-D) δ ppm 0.99 (t, J=7.12 Hz, 3 H) 1.32-1.46 (m, 3 H) 1.68-1.81 (m, 3 H) 2.06-2.18 (m, 2 H) 2.28 (s, 3 H) 3.83-3.89 (m, 2 H) 6.25 (s, 1 H) 7.10-7.25 (m, 5 H). MS (DCI) m/z 314 (M+H)+.

Example 167

(2Z)-2-[5-tert-butyl-3-(cyclobutylmethyl)-1,3,4-thiadiazol-2(3H)-ylidene]-1-(5-chloro-2-methoxyphenyl)ethanone

Example 167A 5-tert-butyl-3-(cyclobutylmethyl)-2-methyl-1,3,4-thiadiazol-3-ium bromide The title compound was prepared as described in Example 47A, substituting (bromomethyl)cyclobutane for butyl iodide and Example 50B for 2,5-dimethyl thiadiazole. $^1$H NMR (300 MHz, DMSO-$d_6$) δ ppm 1.45 (s, 9 H) 1.76 (dd, J=6.78, 3.39 Hz, 4 H) 1.88-1.91 (m, 2 H) 2.91 (s, 1 H) 3.10 (s, 3 H) 4.58 (d, J=7.46 Hz, 2 H). MS (DCI) m/z 225 (M)+.

Example 167B (2Z)-2-[5-tert-butyl-3-(cyclobutylmethyl)-1,3,4-thiadiazol-2(3H)-ylidene]-1-(5-chloro-2-methoxyphenyl)ethanone The title compound was prepared and purified as described in Example 47B, substituting Example 167A for Example 47A. $^1$H NMR (300 MHz, DMSO-d$_6$) δ ppm 1.35 (m, 9 H) 1.79-1.92 (m, 4 H) 1.94-2.05 (m, 2 H) 2.75-2.87 (m, 1 H) 3.85 (s, 3 H) 4.16 (d, J=7.12 Hz, 2 H) 6.55 (s, 1 H) 7.13 (d, J=8.81 Hz, 1 H) 7.45 (dd, J=8.81, 2.71 Hz, 1 H) 7.57 (d, J=2.71 Hz, 1 H). MS (ESI) m/z 393 (M+H)$^+$. Anal calcd for C$_{20}$H$_{25}$ClN$_2$O$_2$S.0.5H$_2$O: C, 59.76; H, 6.52; N, 6.97. Found: C, 59.77; H, 6.30; N, 6.94.

Example 168

(2Z)-2-[5-tert-butyl-3-(cyclobutylmethyl)-1,3,4-thiadiazol-2(3H)-ylidene]-1-(2,3-dichlorophenyl)ethanone The title compound was prepared as described in Example 47B, substituting Example 167A for Example 47A and 2,3-dichlorobenzoic acid for 5-chloro-2-methoxybenzoic acid. $^1$H NMR (300 MHz, DMSO-d$_6$) δ ppm 1.36-1.39 (s, 9 H) 1.78-1.89 (m, 4 H) 1.90-2.02 (m, 2 H) 2.73-2.84 (m, 1 H) 4.18 (d, J=7.46 Hz, 2 H) 6.21 (s, 1 H) 7.40-7.44 (m, 2 H) 7.64-7.69 (m, 1 H). MS (ESI) m/z 397 (M+H)$^+$. Anal calcd for C$_{19}$H$_{22}$Cl$_2$OS.0.2 TFA: C, 55.46; H, 5.33; N, 6.67. Found: C, 55.57; H, 4.97; N, 6.87.

Example 169

(2Z)-1-(5-chloro-2-methoxyphenyl)-2-[3-(cyclobutylmethyl)-4-methyl-1,3-thiazol-2(3H)-ylidene]ethanone Example 169A 3-(cyclobutylmethyl)-2,4-dimethylthiazol-3-ium The title compound was prepared as described in Example 1A, substituting (bromomethyl)cyclobutane for butyl iodide and 2,4-dimethylthiazole for 2,4,5-trimethylthiazole. $^1$H NMR (300 MHz, DMSO-d$_6$) δ ppm 1.77-1.90 (m, 4H) 1.93-2.05 (m, 2 H) 2.53 (d, J=1.36 Hz, 3 H) 2.71-2.83 (m, 1 H) 2.99 (s, 3 H) 4.42 (d, J=7.12 Hz, 2 H) 7.82 (s, 1 H). MS (ESI) m/z 182 (M)$^+$.

Example 169B (2Z)-1-(5-chloro-2-methoxyphenyl)-2-[3-(cyclobutylmethyl)-4-methyl-1,3-thiazol-2(3H)-ylidene]ethanone The title compound was prepared as described in Example 1B, substituting Example 169A for Example 1A. $^1$H NMR (500 MHz, DMSO-d$_6$) δ ppm 1.82-1.90 (m, 4 H) 1.96-2.04 (m, 2 H) 2.30 (s, 3 H) 2.75-2.84 (m, 1 H) 3.87 (s, 3 H) 3.98-4.02 (m, 2 H) 6.53 (s, 1 H) 6.62 (s, 1 H) 7.13 (d, J=8.85 Hz, 1 H) 7.42 (dd, J=8.70, 2.90 Hz, 1 H) 7.63 (d, J=2.75 Hz, 1 H). MS (ESI) m/z 350 (M+H)$^+$.

Example 170

(2Z)-1-(5-chloro-2-methoxyphenyl)-2-[3-(cyclobutylmethyl)-5-(1-hydroxy-1-methylethyl)-4-methyl-1,3-thiazol-2(3H)-ylidene]ethanone To a solution of Example 169B (140 mg, 4 mmol) in tetrahydrofuran (4 mL) at −78° C. was added lithium diisopropylamide (2 M, 0.6 mL). Acetone (81 µL, 1.2 mmol) was added after 5 min. The reaction was quenched with saturated ammonium chloride (10 mL) after 10 min and the reaction mixture was allowed to warm to room temperature. The reaction was extracted with ethyl acetate (3×10 mL). The organics were combined, washed with brine, dried with sodium sulfate and concentrated. The residue was purified by chromatography over silica gel (dichloromethane-EtOAc 5:1 as eluent) to provide the title compound. $^1$H NMR (300 MHz, DMSO-d$_6$) δ ppm 1.48 (s, 6 H) 1.80-1.93 (m, 4 H) 1.99-2.04 (m, 2 H) 2.35 (s, 3 H) 2.68-2.82 (m, 1 H) 3.86 (s, 3 H) 3.96 (d, J=6.78 Hz, 2 H) 5.49 (s, 1 H) 6.53 (s, 1 H) 7.10 (d, J=8.82 Hz, 1 H) 7.39 (dd, J=8.82, 2.71 Hz, 1 H) 7.63 (d, J=2.71 Hz, 1 H). MS (ESI) m/z 408 (M+H)$^+$. Anal calcd for C$_{21}$H$_{26}$ClNO$_3$S.0.7H$_2$O: C, 59.97; H, 6.57; N, 3.33. Found: C, 59.76; H, 6.76; N, 3.02.

Example 171

(2Z)-2-[5-bromo-3-(cyclobutylmethyl)-4-methyl-1,3-thiazol-2(3H)-ylidene]-1-(5-chloro-2-methoxyphenyl)ethanone In a 20 mL vial, a solution of Example 169B (620 mg, 1.772 mmol) was dissolved in acetonitrile (4 ml). N-bromosuccinimide (268 mg, 1.506 mmol) was added and the reaction was stirred for 16 hrs. The reaction was concentrated and purified by chromatography over silica gel (hex-EtOAc 4:1 as eluent) to provide the title compound. $^1$H NMR (300 MHz, DMSO-d$_6$) δ ppm 1.82-1.93 (m, 4 H) 1.95-2.06 (m, 2 H) 2.29 (s, 3 H) 2.71-2.84 (m, 1 H) 3.88 (s, 3 H) 4.06 (d, J=7.12 Hz, 2 H) 6.82 (s, 1 H) 7.14 (d, J=8.82 Hz, 1 H) 7.44 (dd, J=8.82, 2.71 Hz, 1 H) 7.66 (d, J=2.71 Hz, 1 H). MS (ESI) m/z 428 (M+H)$^+$. Anal calcd for C$_{19}$H$_{22}$ClF$_2$NO$_3$S: C, 54.61; H, 5.31; N, 3.35. Found: C, 54.51; H, 5.26; N, 3.35.

Example 172

(2Z)-1-(5-chloro-2-methoxyphenyl)-2-[3-(cyclobutylmethyl)-1,3-thiazol-2(3H)-ylidene]ethanone Example 172A 3-(cyclobutylmethyl)-2-methylthiazol-3-ium The title compound was prepared as described in Example 1A, substituting 2-methylthiazole for 2,4,5-trimethylthiazole and (bromomethyl)cyclobutane for iodobutane. $^1$H NMR (300 MHz, DMSO-d$_6$) δ ppm 1.80-1.92 (m, 4 H) 1.92-2.03 (m, 2 H) 2.80-2.91 (m, 1 H) 2.97 (s, 3 H) 4.46 (d, J=7.80 Hz, 2 H) 8.12 (d, J=4.07 Hz, 1 H) 8.37 (d, J=3.73 Hz, 1 H). MS (ESI) m/z 168 (M)$^+$.

Example 172B (2Z)-1-(5-chloro-2-methoxyphenyl)-2-[3-(cyclobutylmethyl)-1,3-thiazol-2(3H)-ylidene]ethanone The title compound was prepared as described in Example 1B, substituting Example 172A for Example 1A. $^1$H NMR (300 MHz, DMSO-d$_6$) δ ppm 1.78-1.93 (m, 4 H) 1.95-2.02 (m, 2 H) 2.77-2.88 (m, 1 H) 3.85 (s, 3 H) 4.02-4.06 (m, 2 H) 6.56 (d, J=1.36 Hz, 1 H) 6.79-6.82 (m, 1 H) 7.11 (d, J=8.82 Hz, 1 H) 7.41 (dd, J=8.81, 2.71 Hz, 1 H) 7.45 (d, J=4.07 Hz, 1 H) 7.62 (d, J=2.71 Hz, 1 H). MS (ESI) m/z 336 (M+H)$^+$.

Anal calcd for $C_{17}H_{18}ClNO_2S \cdot 0.1\ H_2O$: C, 60.48; H, 5.43; N, 4.15. Found: C, 60.33; H, 5.61; N, 3.95.

Example 173

(2Z)-2-[5-tert-butyl-3-(2,4-difluorobenzyl)-1,3,4-thiadiazol-2(3H)-ylidene]-1-(5-chloro-2-methoxyphenyl)ethanone

Example 173A 5-tert-butyl-3-(2,4-difluorobenzyl)-2-methyl-1,3,4-thiadiazol-3-ium bromide The title compound was prepared as described in Example 47A, substituting 2,4-difluorobenzyl bromide for butyl iodide and Example 50B for 2,5-dimethyl thiadiazole. $^1$H NMR (300 MHz, DMSO-$d_6$) δ ppm 1.39 (s, 9 H) 3.14-3.20 (m, 3 H) 5.81 (s, 2 H) 7.17-7.24 (m, 1 H) 7.36-7.44 (m, 1 H) 7.69 (td, J=8.65, 6.78 Hz, 1 H). MS (ESI) m/z 283 (M)$^+$.

Example 173B (2Z)-2-[5-tert-butyl-3-(2,4-difluorobenzyl)-1,3,4-thiadiazol-2(3H)-ylidene]-1-(5-chloro-2-methoxyphenyl)ethanone The title compound was prepared and purified as described in Example 47B, substituting Example 173A for Example 47A $^1$H NMR (300 MHz, DMSO-$d_6$) δ ppm 1.37 (s, 9 H) 3.80 (s, 3 H) 5.40 (s, 2 H) 6.61 (s, 1 H) 7.11-7.18 (m, 2 H) 7.31-7.39 (m, 2 H) 7.45 (dd, J=8.82, 2.71 Hz, 1 H) 7.59 (d, J=2.71 Hz, 1 H). MS (ESI) m/z 451 (M+H)$^+$. Anal calcd for $C_{22}H_{21}ClF_2N_2O_2S \cdot 0.6\ CH_2Cl_2$: C, 54.08; H, 4.46; N, 5.58. Found: C, 53.97; H, 4.10; N, 5.47.

Example 174

(2Z)-2-[5-tert-butyl-3-(2,4-difluorobenzyl)-1,3,4-thiadiazol-2(3H)-ylidene]-1-(2,3-dichlorophenyl)ethanone The title compound was prepared and purified as described in Example 47B, substituting Example 173A for Example 47A and 2,3-dichlorobenzoic acid for 5-chloro-2-methoxybenzoic acid. $^1$H NMR (300 MHz, DMSO-D6) δ ppm 1.36 (s, 9 H) 5.43 (s, 2 H) 6.28 (s, 1 H) 7.08-7.15 (m, 1 H) 7.27-7.36 (m, 2 H) 7.37-7.45 (m, 2 H) 7.68 (dd, J=6.61, 2.88 Hz, 1 H). MS (ESI) m/z 455 (M+H)$^+$. Anal calcd for $C_{21}H_{18}Cl_2F_2N_2OS$: C, 55.39; H, 3.98; N, 6.15. Found: C, 55.04; H, 3.86; N, 6.18.

Example 175

(2Z)-1-(5-chloro-2-methoxyphenyl)-2-[3-(cyclobutylmethyl)-4-methyl-5-(2,2,2-trifluoro-1-hydroxy-1-methylethyl)-1,3-thiazol-2(3H)-ylidene]ethanone The title compound was prepared and purified as described in Example 170, substituting 1,1,1-trifluoroacetone for acetone. $^1$H NMR (300 MHz, DMSO-$d_6$) δ ppm 1.74 (s, 3 H) 1.81-1.91 (m, 4 H) 1.98-2.01 (m, 2 H) 2.40 (s, 3 H) 2.77 (m, 1 H) 3.86 (s, 3 H) 3.99-4.03 (m, 2 H) 6.62 (s, 1 H) 7.05 (s, 1 H) 7.12 (d, J=9.16 Hz, 1 H) 7.41 (dd, J=8.82, 3.05 Hz, 1 H) 7.62 (d, J=2.71 Hz, 1 H). MS (DCI) m/z 462 (M+H)$^+$. Anal calcd for $C_{21}H_{23}ClF_3NO_3S \cdot 0.1\ CH_2Cl_2$: C, 52.87; H, 4.86; N, 2.94. Found: C, 53.27; H, 4.67; N, 2.86.

Example 176

(2Z)-2-[3-butyl-5-(1-hydroxy-1-methylethyl)-1,3-thiazol-2(3H)-ylidene]-1-(5-chloro-2-methoxyphenyl)ethanone

Example 176A 3-butyl-2-methylthiazol-3-ium iodide

The title compound was prepared as described in Example 1A, substituting 2-methylthiazole for 2,4,5-trimethylthiazole. $^1$H NMR (300 MHz, DMSO-$d_6$) δ ppm 0.92 (t, J=7.29 Hz, 3 H) 1.26-1.39 (m, 2 H) 1.74-1.85 (m, 2 H) 2.95-2.99 (m, 3 H) 4.34-4.42 (m, 2 H) 8.12 (d, J=3.73 Hz, 1 H) 8.40 (d, J=3.73 Hz, 1 H). MS (ESI) m/z 156 (M)$^+$.

Example 176B (Z)-2-(3-butylthiazol-2(3H)-ylidene)-1-(5-chloro-2-methoxyphenyl)ethanone The title compound was prepared as described in Example 1B, substituting Example 176A for Example 1A. MS (ESI) m/z 324 (M+H)$^+$.

Example 176C (2Z)-2-[3-butyl-5-(1-hydroxy-1-methylethyl)-1,3-thiazol-2(3H)-ylidene]-1-(5-chloro-2-methoxyphenyl)ethanone The title compound was prepared and purified as described in Example 170, substituting Example 176B for Example 169B. $^1$H NMR (300 MHz, DMSO-$d_6$) δ ppm 0.93 (t, J=7.29 Hz, 3 H) 1.33 (dd, J=15.09, 7.29 Hz, 2 H) 1.47 (s, 6 H) 1.64-1.75 (m, 2 H) 3.85 (s, 3 H) 3.93 (t, J=7.29 Hz, 2 H) 5.44 (s, 1 H) 6.46 (s, 1 H) 7.11 (d, J=8.82 Hz, 1 H) 7.20 (s, 1 H) 7.40 (dd, J=8.82, 2.71 Hz, 1 H) 7.63 (d, J=2.71 Hz, 1 H). MS (ESI) m/z 382 (M+H)$^+$.

Example 177

(2Z)-1-(5-chloro-2-methoxyphenyl)-2-[3-(cyclobutylmethyl)-5-(1-hydroxy-1-methylethyl)-1,3-thiazol-2(3H)-ylidene]ethanone The title compound was prepared and purified as described in Example 170, substituting Example 172B for Example 169B. $^1$H NMR (300 MHz, DMSO-$d_6$) δ ppm 1.47 (s, 6 H) 1.80-1.90 (m, 4 H) 1.96-2.04 (m, 2 H) 2.72-2.87 (m, 1 H) 3.85 (s, 3 H) 3.97 (d, J=7.12 Hz, 2 H) 5.44 (s, 1 H) 6.46 (s, 1 H) 7.10 (d, J=9.16 Hz, 1 H) 7.20 (s, 1 H) 7.40 (dd, J=8.82, 3.05 Hz, 1 H) 7.60 (d, J=2.71 Hz, 1 H). MS (ESI) m/z 394 (M+H)$^+$.

Example 178

(2Z)-1-(5-chloro-2-methoxyphenyl)-2-[3-(2,4-difluorobenzyl)-4-methyl-1,3-thiazol-2(3H)-ylidene]ethanone

Example 178A 3-(2,4-difluorobenzyl)-2,4-dimethylthiazol-3-ium bromide

The title compound was prepared as described in Example 47A, substituting 2,4-dimethylthiazole for 2,5-dimethyl thiadiazole and 2,4-difluorobenzylbromide for 1-iodobutane. $^1$H NMR (300 MHz, DMSO-$d_6$) δ ppm 2.41 (s, 3 H) 2.97 (s, 3 H) 5.72 (s, 2 H) 7.15 (td, J=8.65, 3.05 Hz, 1 H) 7.27 (td, J=8.65, 6.44 Hz, 1 H) 7.41 (ddd, J=11.36, 8.99, 2.71 Hz, 1 H) 7.89 (s, 1 H). MS (ESI) m/z 240 (M)$^+$.

Example 178B (2Z)-1-(5-chloro-2-methoxyphenyl)-2-[3-(2,4-difluorobenzyl)-4-methyl-1,3-thiazol-2(3H)-ylidene]ethanone The title compound was prepared as described in Example 1B, substituting Example 178A for Example 1A. $^1$H NMR (300 MHz, DMSO-$d_6$) δ ppm 2.29 (s, 3 H) 3.67 (s, 3 H) 5.24 (s, 2 H) 6.46 (d, J=1.36 Hz, 1 H) 6.59 (s, 1 H) 6.95 (td, J=8.65, 6.44 Hz, 1 H) 7.05 (d, J=8.81 Hz, 1 H) 7.07-7.14 (m, 1 H) 7.34-7.42 (m, 2 H) 7.58 (d, J=2.71 Hz, 1 H). MS (ESI) m/z 408 (M+H)$^+$.

Example 179

(2Z)-2-[5-tert-butyl-3-(cyclobutylmethyl)-1,3,4-thiadiazol-2(3H)-ylidene]-1-(2-chloropyridin-3-yl)ethanone The title compound was prepared and purified as described in Example 47B, substituting Example 167A for Example 47A and 2-chloronicotinic acid for 5-chloro-2-methoxybenzoic acid. $^1$H NMR (300 MHz, DMSO-$d_6$) δ ppm 1.37 (s, 9H) 1.78-1.90 (m, 4 H) 1.93-2.02 (m, 2 H) 2.75-2.86 (m, 1 H) 4.20 (d, J=7.12 Hz, 2 H) 6.31 (s, 1 H) 7.50 (dd, J=7.46, 4.75 Hz, 1 H) 7.93 (dd, J=7.46, 2.03 Hz, 1 H) 8.44 (dd, J=4.92, 1.86 Hz, 1 H). MS (ESI) m/z 364 (M+H)$^+$.

Example 180

(2Z)-2-[5-tert-butyl-3-(cyclobutylmethyl)-1,3,4-thiadiazol-2(3H)-ylidene]-1-(2-ethoxypyridin-3-yl)ethanone The title compound was prepared and purified as described in Example 47B, substituting Example 167A for Example 47A and 2-ethoxynicotinic acid for 5-chloro-2-methoxybenzoic acid. $^1$H NMR (300 MHz, DMSO-$d_6$) δ ppm 1.36 (s, 9 H) 1.44 (q, J=6.67 Hz, 3 H) 1.80-1.93 (m, 4 H) 1.96-2.05 (m, 2 H) 2.87 (m, 1 H) 4.17 (d, J=7.12 Hz, 2 H) 4.43 (q, J=7.01 Hz, 2 H) 6.84 (s, 1 H) 7.08 (dd, J=7.46, 5.09 Hz, 1 H) 8.14 (dd, J=7.46, 2.03 Hz, 1 H) 8.21-8.25 (m, 1 H). MS (ESI) m/z 374 (M+H)$^+$. Anal calcd for $C_{19}H_{25}N_3O_2S \cdot 0.4$ TFA $\cdot 0.1H_2O$: C, 59.10; H, 6.63; N, 9.94. Found: C, 59.02; H, 6.92; N, 9.77.

Example 181

(2Z)-2-[5-tert-butyl-3-(cyclobutylmethyl)-1,3,4-thiadiazol-2(3H)-ylidene]-1-[4-(trifluoromethyl)pyridin-3-yl]ethanone The title compound was prepared and purified as described in Example 47B, substituting Example 167A for Example 47A and 4-(trifluoromethyl)nicotinic acid for 5-chloro-2-methoxybenzoic acid. $^1$H NMR (300 MHz, DMSO-$d_6$) δ ppm 1.38 (s, 9 H) 1.79-1.90 (m, 4 H) 1.93-2.02 (m, 2 H) 2.72-2.87 (m, 1 H) 4.22 (d, J=7.46 Hz, 2 H) 6.36 (s, 1 H) 7.80 (d, J=5.09 Hz, 1 H) 8.86-8.90 (m, 2 H). MS (ESI) m/z 398 (M+H)$^+$.

Example 182

(2Z)-2-(3-butyl-5-tert-butyl-1,3,4-thiadiazol-2(3H)-ylidene)-1-(2,3-dichlorophenyl)ethanone The title compound was prepared as described in Example 47B, substituting Example 50C for Example 47A and 2,3-dichlorobenzoic acid for 5-chloro-2-methoxybenzoic acid. $^1$H NMR (300 MHz, DMSO-$d_6$) δ ppm 0.89 (t, J=7.34 Hz, 3 H) 1.14-1.21 (m, 2 H) 1.34-1.39 (m, 9 H) 1.71 (m, 2 H) 4.15 (t, J=7.14 Hz, 2 H) 6.17 (s, 1 H) 7.38-7.45 (m, 2 H) 7.67 (dd, J=6.54, 2.97 Hz, 1 H). MS (ESI) m/z 385 (M+H)$^+$.

Example 183

(2Z)-1-(5-chloro-2-methoxyphenyl)-2-[3-(cyclobutylmethyl)-5-(1-hydroxy-1-methylpropyl)-4-methyl-1,3-thiazol-2(3H)-ylidene]ethanone The title compound was prepared and purified as described in Example 170, substituting 2-butanone for acetone. $^1$H NMR (300 MHz, DMSO-$d_6$) δ ppm 0.76-0.86 (m, 3 H) 1.47 (s, 3 H) 1.69-1.78 (m, 2 H) 1.80-1.88 (m, 4 H) 1.96-2.03 (m, 2 H) 2.33 (s, 3 H) 2.69-2.84 (m, 1 H) 3.85 (s, 3 H) 3.96 (d, J=7.12 Hz, 2 H) 5.34 (s, 1 H) 6.50 (s, 1 H) 7.07-7.12 (m, 1 H) 7.38 (dd, J=8.65, 2.88 Hz, 1 H) 7.61 (d, J=2.71 Hz, 1 H). MS (ESI) m/z 422 (M+H)$^+$.

Example 184

(2Z)-1-(5-chloro-2-methoxyphenyl)-2-[3-(cyclobutylmethyl)-5-(1-ethyl-1-hydroxypropyl)-4-methyl-1,3-thiazol-2(3H)-ylidene]ethanone The title compound was prepared and purified as described in Example 170, substituting 3-pentanone for acetone. $^1$H NMR (300 MHz, DMSO-$d_6$) δ ppm 0.79 (t, J=7.54 Hz, 6 H) 1.71-1.85 (m, 8 H) 1.93-2.02 (m, 2 H) 2.30 (s, 3 H) 2.71-2.85 (m, 1 H) 3.85 (s, 3 H) 3.96 (d, J=6.74 Hz, 2 H) 5.02 (s, 1 H) 6.47 (s, 1 H) 7.10 (d, J=8.73 Hz, 1 H) 7.38 (dd, J=8.92, 2.97 Hz, 1 H), 7.61 (d, J=2.71 Hz, 1 H). MS (ESI) m/z 436 (M+H)$^+$. Anal calcd for $C_{23}H_{30}ClNO_3S \cdot 0.2H_2O$: C, 62.84; H, 6.97; N, 3.19. Found: C, 62.77; H, 7.00; N, 3.05.

Example 185

(2Z)-1-(5-chloro-2-methoxyphenyl)-2-[3-(cyclobutylmethyl)-5-(2-fluoro-1-hydroxy-1-methylethyl)-4-methyl-1,3-thiazol-2(3H)-ylidene]ethanone The title compound was prepared and purified as described in Example 170, substituting 1-fluoroacetone for acetone. $^1$H NMR (300 MHz, DMSO-$d_6$) δ ppm 1.53 (d, J=2.03 Hz, 3 H) 1.80-1.93 (m, 4 H) 1.95-2.03 (m, 2 H) 2.36 (s, 3 H) 2.70-2.81 (m, 1 H) 3.86 (s, 3 H) 3.98 (d, J=7.12 Hz, 2 H) 4.36 (d, J=47.81 Hz, 2 H) 5.94 (s, 1 H) 6.56 (s, 1 H) 7.11 (d, J=8.82 Hz, 1 H) 7.37-7.42 (m, 1 H) 7.62 (d, J=3.05 Hz, 1 H). MS (ESI) m/z 426 (M+H)$^+$. Anal calcd for $C_{21}H_{25}ClFNO_3S$: C, 59.22; H, 5.92; N, 3.29. Found: C, 58.95; H, 5.69; N, 3.25.

Example 186

(2Z)-1-(5-chloro-2-methoxyphenyl)-2-[3-(cyclobutylmethyl)-5-(2,2-difluoro-1-hydroxy-1-methylethyl)-4-methyl-1,3-thiazol-2(3H)-ylidene]ethanone The title compound was prepared and purified as described in Example 170, substituting 1,1-difluoroacetone for acetone. $^1$H NMR (300 MHz, DMSO-$d_6$) δ ppm 1.58 (s, 3 H) 1.79-1.91 (m, 4 H) 1.96-2.05 (m, 2 H) 2.38 (s, 3 H) 2.69-2.83 (m, 1 H) 3.86 (s, 3 H) 4.00 (d, J=6.74 Hz, 2 H) 5.97 (t, J=55.92 Hz, 1H) 6.39 (s, 1 H) 6.59 (s, 1 H) 7.12 (d, J=9.12 Hz, 1 H) 7.38-7.43 (m, 1 H) 7.62 (d, J=2.78 Hz, 1 H). MS (ESI) m/z 444 (M+H)$^+$. Anal calcd for $C_{21}H_{24}ClF_2NO_3S$: C, 56.82; H, 5.45; N, 3.16. Found: C, 56.66; H, 5.54; N, 3.08.

Example 187

(2Z)-2-(3-butyl-5-tert-butyl-1,3-thiazol-2(3H)-ylidene)-1-[2-(trifluoromethyl)phenyl]ethanone The title compound was prepared and purified as described in Example 35C, substituting Example 153C for Example 35B and 2-trifluorobenzoic acid chloride for 2-chloronicotinoyl chloride. $^1$H NMR (300 MHz, CDCl$_3$) δ ppm 0.96 (t, J=7.29 Hz, 3 H) 1.31-1.44 (m, 11 H) 1.72-1.82 (m, 2 H) 3.83-3.92 (m, 2 H) 6.67 (s, 1 H) 7.45-7.54 (m, 1 H) 7.55-7.61 (m, 2 H) 7.69 (d, J=7.80 Hz, 1 H). MS (ESI) m/z 384 (M+H).

Example 188

(2Z)-1-(5-chloro-2-methoxyphenyl)-2-[3-(cyclobutylmethyl)-1,3,4-thiadiazol-2(3H)-ylidene]ethanone

Example 188A 3-(cyclobutylmethyl)-2-methyl-1,3,4-thiadiazol-3-ium bromide

The title compound was prepared as described in Example 47A, substituting 2-methylthiadiazole for 2,5-dimethylthiadiazole. $^1$H NMR (300 MHz, DMSO-$d_6$) δ ppm 1.79-1.94 (m, 4 H) 1.97-2.07 (m, 2 H) 2.85 (s, 3 H) 2.90 (m, 1 H) 4.70 (d, J=7.54 Hz, 2 H) 10.70 (s, 1 H). MS (ESI) m/z 169 (M+H)$^+$.

Example 188B (2Z)-1-(5-chloro-2-methoxyphenyl)-2-[3-(cyclobutylmethyl)-1,3,4-thiadiazol-2(3H)-ylidene]ethanone The procedure in Example 47B was followed, substituting Example 188A for Example 47A to afford the title compound. $^1$H NMR (300 MHz, CDCl$_3$) δ ppm 1.85-2.00 (m, 4 H) 2.05-2.16 (m, 2 H) 2.95 (m, 1 H) 3.88 (s, 3 H) 4.21 (d, J=7.14 Hz, 2 H) 6.89 (d, J=8.73 Hz, 1 H) 7.33 (dd, J=8.72, 2.78 Hz, 1 H) 7.75 (d, J=2.78 Hz, 1 H) 8.16 (s, 1 H). MS (ESI) m/z 337 (M+H)$^+$.

Example 189 ethyl (2Z)-3-butyl-2-[2-(5-chloro-2-methoxyphenyl)-2-oxoethylidene]-5-(1-hydroxy-1-methylethyl)-2,3-dihydro-1,3-thiazole-4-carboxylate The title compound was prepared and purified as described in Example 170, substituting Example 45 for Example 169B. $^1$H NMR (300 MHz, DMSO-$d_6$) δ ppm 0.90-0.96 (m, 3 H) 1.29-1.38 (m, 5 H) 1.49 (s, 6 H) 1.70 (m, 2 H) 3.82-3.90 (m, 5 H) 4.36 (q, J=7.14 Hz, 2 H) 5.81 (s, 1 H) 6.55 (s, 1 H) 7.13 (d, J=8.72 Hz, 1 H) 7.43 (dd, J=8.92, 2.97 Hz, 1 H) 7.64 (d, J=2.78 Hz, 1 H). MS (ESI) m/z 454 (M+H)$^+$.

Example 190

(2Z)-3-butyl-2-[2-(5-chloro-2-methoxyphenyl)-2-oxoethylidene]-6,6-dimethyl-3,6-dihydrofuro[3,4-d][1,3]thiazol-4(2H)-one

Example 190A (Z)-3-butyl-2-(2-(5-chloro-2-methoxyphenyl)-2-oxoethylidene)-5-(2-hydroxypropan-2-yl)-2,3-dihydrothiazole-4-carboxylic acid To a 50 mL round-bottomed flask, Example 189 (45 mg, 0.099 mmol) was dissolved in ethanol (5.00 mL), sodium hydroxide (14 mg, 0.350 mmol) in water (5 mL) was added and stirred for 2 hrs. To the reaction was added hydrogen chloride solution (2 N) till pH=5-6 and extracted with EtOAc (3×5 mL). The organic layers were combined and dried. $^1$H NMR (300 MHz, DMSO-$d_6$) δ ppm 0.93 (t, J=7.34 Hz, 3 H) 1.34 (m, 3 H) 1.50 (s, 6 H) 1.66-1.76 (m, 2 H) 3.86 (s, 3 H) 3.89-3.96 (m, 2 H) 6.52 (s, 1 H) 7.11-7.16 (m, 1 H) 7.40-7.47 (m, 1 H) 7.63-7.67 (m, 1 H). MS (ESI) m/z 426 (M+H)$^+$.

Example 190B (2Z)-3-butyl-2-[2-(5-chloro-2-methoxyphenyl)-2-oxoethylidene]-6,6-dimethyl-3,6-dihydrofuro[3,4-d][1,3]thiazol-4(2H)-one In a 20 mL vial, Example 190A (60 mg, 0.141 mmol) was dissolved in CH$_2$Cl$_2$ (2 ml). Support-bound DCC (3 mmol/g, 100 mg) was added and shaken over weekend. The reaction mixture was filtered and the solvent was removed to obtain the title compound. $^1$H NMR (300 MHz, DMSO-$d_6$) δ ppm 0.93 (t, J=7.34 Hz, 3 H) 1.31-1.41 (m, 2 H) 1.69 (s, 6 H) 1.70-1.79 (m, 2 H) 3.88 (s, 3 H) 4.12 (t, J=7.34 Hz, 2 H) 6.72 (s, 1 H) 7.17 (d, J=9.12 Hz, 1 H) 7.48 (dd, J=8.72, 2.78 Hz, 1 H) 7.64 (d, J=2.78 Hz, 1 H). MS (ESI) m/z 408 (M+H)$^+$. Anal calcd for $C_{20}H_{22}ClNO_4S$: C, 58.89; H, 5.44; N, 3.43. Found: C, 59.02; H, 5.52; N, 3.43.

Example 191

(2Z)-2-(3-butyl-4,5-dimethyl-1,3-thiazol-2(3H)-ylidene)-1-(5-chloro-2-hydroxyphenyl)ethanone Example 1 (180 mg, 0.5 mmol) in CHCl$_3$ (12 mL) was treated with iodomethane (1 mL) and AlCl$_3$ (133 mg, 1 mmol) at room temperature for 24 h. The mixture was washed with 10% solution of NaHCO$_3$, brine, dried with anhydrous MgSO$_4$ and concentrated under reduced pressure. The residue was purified by chromatography (hexane-EtOAc 1:1 as eluent) to afford 100 mg of the title compound. $^1$H NMR (300 MHz, DMSO-$d_6$) δ 0.95 (t, J=7 Hz, 3 H), 1.40 (sextet, J=7 Hz, 2 H), 1.64 (quintet, J=7 Hz, 2 H), 2.21 (s, 3 H), 2.25 (s, 3 H), 4.19 (t, J=7 Hz, 2 H), 6.67 (s, 1 H), 6.81 (d, J=9 Hz, 1 H), 7.30 (dd, J=9 Hz, 3 Hz, 1 H), 8.01 (d, J=3 Hz, 1 H), 14.59 (s, 1 H); MS (DCI/NH$_3$) m/z 338 (M+H)$^+$. Anal calcd for $C_{17}H_{20}ClNO_2S$: C, 60.43; H, 5.97; N, 4.15. Found: C, 60.24; H, 5.76; N, 3.97.

Example 192 tert-butyl (2Z)-3-butyl-2-[2-(5-chloro-2-methoxyphenyl)-2-oxoethylidene]-2,3-dihydro-1,3-thiazol-4-ylcarbamate

Example 192A (Z)-3-butyl-2-(2-(5-chloro-2-methoxyphenyl)-2-oxoethylidene)-2,3-dihydrothiazole-4-carboxylic acid The title compound was prepared and purified as described in Example 190A, substituting Example 45 for Example 189. $^1$H NMR (300 MHz, DMSO-$d_6$) δ ppm 0.94 (t, J=7.54 Hz, 3 H) 1.29-1.42 (m, 2 H) 1.65-1.77 (m, 2H) 3.87 (s, 3 H) 4.32-4.39 (m, 2 H) 6.67 (s, 1 H) 7.14 (d, J=9.12 Hz, 1 H) 7.44 (dd, J=8.73, 2.78 Hz, 1 H) 7.66 (d, J=2.78 Hz, 1 H). MS (DCI/NH$_3$) m/z 368 (M+H)$^+$.

Example 192B tert-butyl (2Z)-3-butyl-2-[2-(5-chloro-2-methoxyphenyl)-2-oxoethylidene]-2,3-dihydro-1,3-thiazol-4-ylcarbamate To a 50 mL vial, Example 192A (650 mg, 1.767 mmol) was dissolved in toluene (8 ml). Diphenyl phosphorazide (584 mg, 2.120 mmol) was added followed by addition of triethylamine (0.493 mL, 3.53 mmol) and 2-methylpropan-2-ol (5 mL, 1.767 mmol) and heated at 85° C. for 2 hr. The reaction mix was concentrated and purified over silica gel (hexane-EtOAc 4:1 as eluent) to provide title compound as a brown solid. $^1$H NMR (300 MHz, DMSO-$d_6$) δ ppm 0.92 (m, 3 H) 1.29-1.38 (m, 2 H) 1.40-1.50 (m, 9 H) 1.57-1.71 (m, 2 H) 3.80-3.90 (m, 5 H) 6.59 (m, 2 H) 7.12 (d, J=8.82 Hz, 1 H), 7.41 (m, 1H), 7.65 (m, 1H), 9.21 (s, 1H). MS (ESI) m/z 439 (M+H)$^+$.

Example 193

(2Z)-2-(3-butyl-4,5-dimethyl-1,3-thiazol-2(3H)-ylidene)-1-[5-chloro-2-(dimethylamino)phenyl]ethanone In a 25 mL vial, Example 110 (70.0 mg, 0.206 mmol) was dissolved in dimethyl formamide (15 ml). Potassium carbonate (34.2 mg, 0.247 mmol) was added followed by addition of methylhydrazine (95 mg, 2.060 mmol) and stirred for 48 hrs at 110° C. The title compound was isolated as a by-product from the displacement of fluorine by dimethylamine from dimethyl formamide. $^1$H NMR (300 MHz, DMSO-$d_6$) δ ppm 0.94 (t, J=7.29 Hz, 3 H) 1.32-1.43 (m, 2 H) 1.63 (m, 2 H) 2.15 (s, 3 H) 2.17 (s, 3 H) 2.68 (s, 6 H) 3.82-3.89 (m, 2 H) 6.41 (s, 1 H) 6.95 (d, J=8.82 Hz, 1 H) 7.26 (dd, J=8.82, 2.71 Hz, 1 H) 7.34 (d, J=2.71 Hz, 1 H). MS (ESI) m/z 365 (M+H)$^+$. Anal calcd for $C_{19}H_{25}ClN_2OS$: C, 62.53; H, 6.90; N, 7.68. Found: C, 62.37; H, 6.66; N, 7.78.

Example 194

(2Z)-1-(5-chloro-2-methoxyphenyl)-2-[3-(cyclobutylmethyl)-5-(1-ethyl-1-hydroxypropyl)-1,3-thiazol-2(3H)-ylidene]ethanone The title compound was prepared and purified as described in Example 170, substituting Example 172B for Example 169B and 3-pentanone for acetone. $^1$H NMR (300 MHz, CDCl$_3$) δ ppm 0.84-0.93 (m, 6 H) 1.82-1.95 (m, 8 H) 2.04-2.16 (m, 2 H) 2.82-2.96 (m, 1 H) 3.86-3.94 (m, 5 H) 6.46 (s, 1 H) 6.74 (s, 1 H) 6.87 (d, J=8.73 Hz, 1 H). MS (DCI) m/z 422 (M+H)$^+$.

Example 195

(2Z)-2-[5-(1-amino-1-ethylpropyl)-3-(cyclobutylmethyl)-1,3-thiazol-2(3H)-ylidene]-1-(5-chloro-2-methoxyphenyl)ethanone

Example 195A 2-methyl-N-(pentan-3-ylidene)propane-2-sulfinamide

To a 40 mL vial, pentan-3-one (1.049 ml, 9.90 mmol) was dissolved in THF (17 ml). Titanium ethoxide (3.42 ml, 16.50 mmol) was added followed by addition of 2-methylpropane-2-sulfinamide (1.0 g, 8.25 mmol) and the reaction was heated to 90° C. for 36 hr. The reaction was poured into equal volume of brine and stirred for 30 min before filtration through a silica gel pad. The filtrate was dried with sodium sulfate, concentrated and purified over silica gel (hexane-EtOAc 4:1 as eluent) to provide title compound. $^1$H NMR (300 MHz, DMSO-$d_6$) δ ppm 1.00 (m, 3 H) 1.06-1.13 (m, 3 H) 1.14 (s, 9 H) 2.50 (m, 2 H) 2.62 (m, 2 H). MS (DCI) m/z 190 (M+H)$^+$.

Example 195B (2Z)-2-[5-(1-amino-1-ethylpropyl)-3-(cyclobutylmethyl)-1,3-thiazol-2(3H)-ylidene]-1-(5-chloro-2-methoxyphenyl)ethanone The title compound was prepared and purified as described in Example 170, substituting Example 172B for Example 169B and Example 195A for acetone. $^1$H NMR (300 MHz, DMSO-$d_6$) δ ppm 0.77 (t, J=7.34 Hz, 6 H) 1.54-1.63 (m, 4 H) 1.74-1.88 (m, 4 H) 1.90-2.02 (m, 2 H) 2.72-2.86 (m, 1 H) 3.84 (s, 3 H) 3.97 (d, J=7.54 Hz, 2 H) 6.40 (s, 1H) 7.09 (d, J=8.72 Hz, 1 H) 7.13 (s, 1 H) 7.38 (dd, J=8.72, 2.78 Hz, 1 H) 7.57 (d, J=2.78 Hz, 1 H). MS (DCI) m/z 421 (M+H)$^+$.

Example 196

(2Z)-2-(3-butyl-5-tert-butyl-1,3-thiazol-2(3H)-ylidene)-1-[6-chloro-4-(trifluoromethyl)pyridin-3-yl]ethanone The title compound was prepared and purified as described in Example 35C, substituting Example 153C for Example 35B and 6-chloro-4-(trifluoromethyl)nicotinoyl chloride for 2-chloronicotinoyl chloride. $^1$H NMR (300 MHz, DMSO-$d_6$) δ ppm 0.85-0.93 (m, 3 H) 1.24-1.34 (m, 11 H) 1.61-1.71 (m, 2 H) 3.97 (t, J=7.46 Hz, 2 H) 6.09 (s, 1 H) 7.24 (s, 1 H) 7.94 (s, 1 H) 8.70 (s, 1 H). MS (DCI) m/z 419 (M+H)$^+$.

Example 197

(2Z)-3-butyl-2-[2-(5-chloro-2-methoxyphenyl)-2-oxoethylidene]-6,6-diethyl-2,3,5,6-tetrahydro-4H-pyrrolo[3,4-d][1,3]thiazol-4-one The title compound was prepared and purified using the procedure described in Example 170, substituting Example 45 for Example 169B and Example 195A for acetone. $^1$H NMR (300 MHz, DMSO-$d_6$) δ ppm 0.72 (t, J=7.34 Hz, 6 H) 0.87-0.94 (m, 3 H) 1.24-1.37 (m, 2 H) 1.70-1.86 (m, 6 H) 3.87 (s, 3 H) 4.24 (t, J=6.94 Hz, 2 H) 6.67 (s, 1 H) 7.15 (d, J=9.12

Hz, 1 H) 7.46 (dd, J=8.72, 2.78 Hz, 1 H) 7.63 (d, J=2.78 Hz, 1 H) 8.64 (s, 1 H). MS (DCI) m/z 435 (M+H)$^+$. Anal calcd for $C_{22}H_{27}ClN_2O_3S$: C, 60.75; H, 6.26; N, 6.44. Found: C, 60.65; H, 6.21; N, 6.55.

Example 198

(2Z)-2-[3-butyl-5-[2-fluoro-1-(fluoromethyl)-1-hydroxyethyl]-1,3-thiazol-2(3H)-ylidene]-1-(5-chloro-2-methoxyphenyl)ethanone The title compound was prepared and purified as described in Example 170, substituting Example 176B for Example 169B and 1,3-difluoroacetone for acetone. $^1$H NMR (300 MHz, DMSO-d$_6$) δ ppm 0.93 (t, J=7.29 Hz, 3 H) 1.27-1.39 (m, 2 H) 1.64-1.76 (m, 2 H) 3.85 (s, 3 H) 3.97 (t, J=7.29 Hz, 2 H) 4.45-4.61 (m, 4 H) 6.49 (s, 1 H) 6.54 (s, 1 H) 7.12 (d, J=8.82 Hz, 1 H) 7.37 (s, 1 H) 7.41 (dd, J=8.82, 2.71 Hz, 1 H) 7.63 (d, J=2.71 Hz, 1 H). MS (DCI) m/z 418 (M+H)$^+$. Anal calcd for $C_{19}H_{22}ClF_2NO_3S$: C, 54.61; H, 5.31; N, 3.35. Found: C, 54.51; H, 5.26; N, 3.35.

Example 199

(2Z)-2-(3-butyl-5-isopropenyl-1,3-thiazol-2(3H)-ylidene)-1-[6-chloro-4-(trifluoromethyl)pyridin-3-yl]ethanone This compound was separated as a by-product from the preparation of Example 196. $^1$H NMR (300 MHz, DMSO-d$_6$) δ ppm 0.90 (t, J=7.29 Hz, 3 H) 1.29-1.35 (m, 2 H) 1.62-1.74 (m, 2 H) 2.05 (m, 3 H) 4.02 (t, J=7.29 Hz, 2 H) 5.05 (m, 1 H) 5.15 (m, 1 H) 6.24 (s, 1 H) 7.58 (s, 1 H) 7.97 (s, 1 H) 8.75 (s, 1 H). MS (DCI) m/z 403 (M+H)$^+$.

Example 200

(2Z)-2-[3-butyl-4-(1-hydroxy-1-methylethyl)-1,3-thiazol-2(3H)-ylidene]-1-(5-chloro-2-methoxyphenyl)ethanone To a solution of Example 45 (60 mg, 0.152 mmol) in tetrahydrofuran (1 ml) at −78° C. was added methyllithium (0.284 ml, 0.455 mmol). The reaction was monitored by LC-MS and was quenched with saturated ammonium hydrochloride (5 mL) upon consumption of starting material. Upon warming to room temperature the resulting mixture was extracted with ethyl acetate (3×10 mL). The title compound was purified by HPLC specified in Example 35C. $^1$H NMR (300 MHz, CD$_3$OD) δ ppm 1.05 (t, J=7.29 Hz, 3 H) 1.45-1.57 (m, 2 H) 1.65 (s, 6 H) 1.83-1.95 (m, 2 H) 3.91 (s, 3 H) 4.43 (d, J=8.81 Hz, 2 H) 6.67 (m, 1 H) 6.69 (m, 1 H) 7.07 (d, J=8.82 Hz, 1 H) 7.35 (dd, J=8.82, 2.71 Hz, 1 H) 7.71 (d, J=2.71 Hz, 1 H). MS (DCI) m/z 382 (M+H)$^+$.

Example 201

(Z)-2-(4-acetyl-3-butylthiazol-2(3H)-ylidene)-1-(5-chloro-2-methoxyphenyl)ethanone The title compound was isolated from Example 200 as a by-product. $^1$H NMR (300 MHz, CD$_3$OD) δ ppm 1.02 (t, J=7.46 Hz, 3 H) 1.45 (m, 2 H) 1.75-1.86 (m, 2 H) 2.56 (s, 3 H) 3.91 (s, 3 H) 4.34-4.43 (m, 2 H) 6.73 (d, J=1.36 Hz, 1 H) 7.08 (d, J=8.81 Hz, 1 H) 7.38 (dd, J=8.98, 2.88 Hz, 1 H) 8.02 (s, 1 H). MS (DCI) m/z 366 (M+H)$^+$.

Example 202

(2Z)-1-(5-chloro-2-methoxyphenyl)-2-[3-(cyclobutylmethyl)-5-[2-fluoro-1-(fluoromethyl)-1-hydroxyethyl]-4-methyl-1,3-thiazol-2(3H)-ylidene]ethanone The title compound was prepared and purified as described in Example 170, substituting 1,3-difluoroacetone for acetone. $^1$H NMR (300 MHz, DMSO-d$_6$) δ ppm 1.78-1.90 (m, 4 H) 1.92-2.05 (m, 2 H) 2.70-2.81 (m, 1 H) 3.86 (s, 3 H) 4.00 (d, J=6.78 Hz, 2H) 4.45-4.55 (m, 2 H) 4.62-4.71 (m, 2 H) 6.47 (s, 1 H) 6.60 (s, 1 H) 7.12 (d, J=9.15 Hz, 1 H) 7.36-7.43 (m, 1 H) 7.62 (d, J=2.71 Hz, 1 H). MS (DCI) m/z 444 (M+H)$^+$.

Example 203 ethyl (2Z)-5-(1-amino-1-methylethyl)-3-butyl-2-[2-(5-chloro-2-methoxyphenyl)-2-oxoethylidene]-2,3-dihydro-1,3-thiazole-4-carboxylate

Example 203A 2-methyl-N-(propan-2-ylidene)propane-2-sulfinamide

The title compound was prepared and purified as described in Example 195A, substituting acetone for 3-pentanone. $^1$H NMR (300 MHz, DMSO-d$_6$) δ ppm 1.12 (s, 9 H) 2.14 (s, 3 H) 2.26 (s, 3 H). MS (DCI) m/z 162 (M+H)$^+$.

Example 203B ethyl (2Z)-5-(1-amino-1-methylethyl)-3-butyl-2-[2-(5-chloro-2-methoxyphenyl)-2-oxoethylidene]-2,3-dihydro-1,3-thiazole-4-carboxylate The title compound was prepared and purified as described in Example 170, substituting Example 45 for Example 169B and Example 203A for acetone. $^1$H NMR (300 MHz, DMSO-d$_6$) δ ppm 0.94 (t, J=7.29 Hz, 3 H) 1.38 (m, 5 H) 1.66 (s, 6 H) 1.74 (m, 2 H) 3.87 (s, 3 H) 3.91 (m, 2 H) 4.49 (q, J=7.12 Hz, 2 H) 6.73 (s, 1 H) 7.17 (d, J=9.16 Hz, 1 H) 7.44-7.50 (m, 1 H) 7.66 (d, J=3.05 Hz, 1 H) 8.52 (b, 2 H). MS (DCI) m/z 453 (M+H)$^+$.

Example 204

(2Z)-3-butyl-2-[2-(5-chloro-2-methoxyphenyl)-2-oxoethylidene]-6,6-dimethyl-2,3,5,6-tetrahydro-4H-pyrrolo[3,4-d][1,3]thiazol-4-one The title compound was obtained as a by-product from Example 203B. $^1$H NMR (300 MHz, DMSO-d$_6$) δ ppm 0.92 (t, J=7.46 Hz, 3 H) 1.27-1.40 (m, 2 H) 1.49 (s, 6 H) 1.68-1.78 (m, 2 H) 3.87 (s, 3 H) 4.20 (t, J=6.95 Hz, 2 H) 6.67 (s, 1 H) 7.15 (d, J=8.82 Hz, 1 H) 7.45 (dd, J=8.82, 2.71 Hz, 1 H) 7.64 (d, J=3.05 Hz, 1 H) 8.83 (s, 1 H). MS (DCI) m/z 407 (M+H)$^+$.

Example 205

(Z)-2-(3-butyl-4,5-dimethylthiazol-2(3H)-ylidene)-1-(5-chloro-2-methoxyphenyl)ethanethione A mixture of Example 1 (54 mg, 0.15 mmol) and P$_2$S$_5$ (115 mg, 0.5 mmol) in pyridine (10 mL) was refluxed for 2 h. The mixture was then concentrated under reduced pressure and the residue was partitioned between water and EtOAc. The ethyl acetate layer was washed with brine, dried with anhydrous MgSO$_4$ and concentrated under reduced pressure. The residue was purified by chromatography (hexane-EtOAc 1:1 as eluent) to afford 25 mg of product. $^1$H NMR (300 MHz, DMSO-d$_6$) δ 0.95 (t, J=7 Hz, 3H), 1.37 (sextet, J=7 Hz, 2H), 1.70 (quintet, J=7 Hz, 2H), 2.26 (s, 3H), 2.32 (s, 3H), 3.78 (s, 3H), 4.15 (t, J=7 Hz, 2H), 7.05 (d, J=9 Hz, 1H), 7.28 (dd, J=9 Hz, 3 Hz, 1H), 7.41 (s, 1H), 7.53 (d, J=3 Hz, 1H); MS (ESI) m/z 368 (M+H)$^+$. Anal calcd for C$_{18}$H$_{22}$ClNOS$_2$: C, 58.76; H, 6.03; N, 3.81. Found: C, 58.35; H, 5.96; N, 3.66.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed:
1. A compound according to formula (I),

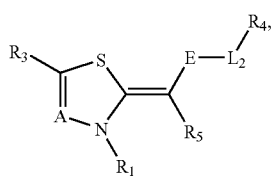

(I)

or a pharmaceutically acceptable salt thereof, wherein
A is C(R$_2$);
E is C(O) or C(S);
R$_1$ is C$_3$-C$_7$ alkyl, alkenyl, alkoxy-(C$_2$-C$_6$ alkylene)-, alkoxycarbonylalkyl, alkylcarbonylalkyl, alkylsulfinylalkyl, alkylsulfonylalkyl, alkylthioalkyl, alkynyl, aryloxy-(C$_2$-C$_6$ alkylene)-, arylalkoxy-(C$_2$-C$_6$ alkylene)-, arylcarbonyloxy-(C$_2$-C$_6$ alkylene)-, carboxyalkyl, cycloalkyl, cycloalkylalkyl, cyanoalkyl, haloalkyl, haloalkoxy-(C$_2$-C$_6$ alkylene)-, heteroaryl, heteroarylalkyl, heteroaryloxy-(C$_2$-C$_6$ alkylene)-, heteroarylcarbonyloxy-(C$_2$-C$_6$ alkylene)-, heterocycle, heterocyclealkyl, heterocycleoxy-(C$_2$-C$_6$ alkylene)-, hydroxy-(C$_2$-C$_6$ alkylene)-, R$_a$R$_b$N—(C$_2$-C$_6$ alkylene)-, RA$_j$N—C(O)-alkylene-, R$_c$R$_d$N—C(O)—NR$_c$—(C$_2$-C$_6$ alkylene)-, R$_e$O—N═C(R$_z$)-alkylene-, or R$_f$R$_g$N—N═C(R$_z$)-alkylene-;
R$_2$ and R$_3$ are each independently hydrogen, alkenyl, alkoxy, alkoxyalkyl, alkoxycarbonyl, alkoxycarbonylalkyl, alkyl, alkynyl, alkylcarbonyl, alkylsulfinyl, alkylsulfonyl, alkylthio, aryl, arylalkyl, arylalkenyl, azidoalkyl, cyano, cycloalkyl, formyl, halogen, haloalkyl, heteroaryl, heterocycle, hydroxyalkyl, hydroxyalkynyl, hydroxyhaloalkyl, R$_j$R$_k$N—, R$_j$R$_k$N-alkylene-, R$_m$RN—C(O)—, R$_p$O—N═C(R$_z$)-alkylene-, R$_p$O—N═C(R$_z$)—, or R,R$_s$N—N═C(R$_z$)-alkylene-, or
R$_2$ and R$_3$ taken together with the carbon atoms to which they are attached form a heteroaryl, a heterocycle, or a cycloalkenyl ring;
R$_4$ is C$_4$-C$_{10}$ alkyl, wherein the C$_4$-C$_{10}$ alkyl group is optionally substituted with one substituent selected from the group consisting of hydroxy, alkoxy, haloalkoxy, cyano, —C(O)N(R$_z$)$_2$, and —N(R$_z$)C(O)R$_z$; alkenyl, alkynyl, naphthyl, arylalkyl, cycloalkyl, cycloalkylalkyl, cycloalkenyl, cycloalkenylalkyl, haloalkyl, heteroaryl, heteroarylalkyl, heterocycle, heterocyclealkyl, wherein the naphthyl, cycloalkyl, cycloalkenyl, heteroaryl, heterocycle, the aryl moiety of the arylalkyl, the cycloalkyl moiety of the cycloalkylalkyl, the cycloalkenyl moiety of the cycloalkenylalkyl, the heteroaryl moiety of the heteroarylalkyl, and the heterocycle moiety of the heterocyclealkyl are each independently unsubstituted or substituted with 1, 2, 3, 4, 5, or 6 substituents as represented by R$_6$;
or phenyl substituted with 1, 2, 3, 4, or 5 substituents as represented by R$_6$;
R$_6$, at each occurrence, is independently selected from the group consisting of alkyl, alkenyl, alkynyl, nitro, cyano, halogen, haloalkyl, oxo, —OR$_{eu}$, —O—(CR$_{ju}$R$_{ku}$)$_x$—N(R$_{wu}$)$_2$, —OC(O)R$_{eu}$, —SR$_{eu}$, —S(O)R, —S(O)$_2$R$_{fu}$, —S(O)$_2$N(R$_{wu}$)(R$_{gu}$), —N(R$_{wu}$)(R$_{gu}$), —N(R$_{wu}$)C(O)R$_{eu}$, —N(R$_{wu}$)C(O)OR$_{eu}$, —N(R$_{wu}$)S(O)$_2$R$_{fu}$, —N(R$_{wu}$)C(O)N(R$_{wu}$)(R$_{gu}$), —N(R$_{wu}$)S(O)$_2$N(R$_{wii}$)(R$_{gu}$), —C(0)R$_{eu}$—C(O)0(R$_{eu}$), —C(0)11(R$_w$AR$_{gu}$), haloalkyl, —(CR$_{ju}$R$_{ku}$)$_x$—CN, —(CR$_{ju}$R$_{ku}$)$_x$—OR$_{eu}$, —(CR$_{ju}$R$_{ku}$)$_x$—OC(O)R$_{eu}$, —(CR$_{ju}$R$_{ku}$)$_x$—SR$_{eu}$, CR$_{ju}$R$_{ku}$)$_x$—S(O)R$_{fu}$, —(CR$_{ju}$R$_{ku}$)$_x$—S(O)$_2$R$_{fu}$, —(CR$_{ju}$R$_{ku}$)$_x$—N(R$_{wu}$)(R$_{gu}$), —(CR$_{ju}$R$_{ku}$)$_x$—N(R$_{wu}$)C(0)R$_{eu}$, —(CR$_{ju}$R$_{ku}$)$_x$—N(R$_{wu}$)S(O)$_2$R$_{fu}$, —(CR$_{ju}$R$_{ku}$)$_x$—N(R$_{wu}$)C(O)N(R$_{wu}$)(R$_{gu}$), —(CR$_{ju}$R$_{ku}$)$_x$—N(R$_{wu}$)S($^O$)$_2$N(R$_{wu}$)(R$_{gu}$), —(CR$_{ju}$R$_{ku}$)$_x$—C(O)R$_{eu}$, —(CR$_{ju}$R$_{ku}$)$_x$—C(O)0(R$_{eu}$), —(CR$_{ju}$R$_{ku}$)$_x$—C(0)N(R$_{wu}$)(R$_{gu}$), —C(R$_{wu}$)═N—OR$_{wu}$, aryl, cycloalkyl, and heterocycle;
R$_{wu}$, at each occurrence, is independently hydrogen, alkyl, or haloalkyl;
R$_{eu}$ and R$_{gu}$, at each occurrence, are each independently hydrogen, alkyl, alkoxyalkyl, cycloalkyl, cycloalkylalkyl, heterocycle, haloalkoxyalkyl, or haloalkyl;
wherein the cycloalkyl, the heterocycle, and the cycloalkyl moiety of the cycloalkylalkyl are each independently unsubstituted or substituted with 1, 2, 3, 4, 5 or 6 substituents selected from the group consisting of alkyl, halogen, and haloalkyl;
R$_{fu}$, at each occurrence, is independently alkyl or haloalkyl;
R$_{ju}$ and R$_{ku}$, at each occurrence, are each independently hydrogen, halogen, alkyl, or haloalkyl;
x is 1, 2, 3, 4, or 5;
R$_5$ is hydrogen, alkyl, alkenyl, alkynyl, cyano, or halogen;
L$_2$ is a bond, —N(R$_e$)— or —O—;
R$_a$ and R$_b$ are each independently selected from the group consisting of hydrogen, alkyl, alkylcarbonyl, alkylsulfonyl, alkoxycarbonyl, aryl, arylalkyl, cycloalkyl, cycloalkylalkyl, heteroaryl, heteroarylalkyl, heterocycle, or heterocyclealkyl;
R$_c$ and R$_d$, at each occurrence, are each independently hydrogen, alkyl, or haloalkyl;
R$_e$, at each occurrence, is independently hydrogen, alkyl, alkenyl, alkoxyalkyl, alkynyl, cyanoalkyl, cycloalkyl, cycloalkylalkyl, haloalkyl, or hydroxyalkyl;
R$_f$ and R$_g$, are each independently hydrogen, alkyl, alkenyl, alkoxycarbonyl, alkoxyalkyl, alkynyl, arylalkyl, cyanoalkyl, cycloalkylalkyl, haloalkyl, heteroarylalkyl, heterocyclealkyl, hydroxyalkyl or nitroalkyl; or R$_f$ and R$_g$, together with the nitrogen atom to which they are attached, form a 5-, 6-, or 7-membered heterocycle ring;
j and R$_k$, at each occurrence, are each independently hydrogen, alkyl, alkoxycarbonyl, alkylcarbonyl, alkylsulfonyl, arylalkyl, or —C(O)N(R$_z$)$_2$;
R$_m$ and R$_n$ are each independently hydrogen, alkyl, or haloalkyl;

$R_p$, at each occurrence, is independently hydrogen, alkyl, alkenyl, alkoxyalkyl, alkynyl, cyanoalkyl, cycloalkylalkyl, haloalkyl, heterocyclealkyl, hydroxyalkyl, or nitroalkyl;

$R_r$ and $R_s$ are each independently hydrogen, alkyl, alkenyl, alkoxyalkyl, alkynyl, cyanoalkyl, cycloalkylalkyl, haloalkyl, heterocyclealkyl, hydroxyalkyl, or nitroalkyl; or $R_r$ and $R_s$, together with the nitrogen atom to which they are attached, form a 5-, 6-, or 7- membered heterocycle ring; and $R_z$, at each occurrence, is independently hydrogen, alkyl, or haloalkyl;

with the proviso that when A is —C($R_2$), $R_2$ is hydrogen or $C_1$-$C_5$ alkyl, $R_3$ is hydrogen or phenyl, E is C(O), $L_2$ is a bond, and $R_4$ is aryl, then $R_1$ is not $C_3$-$C_5$ alkyl, $C_2$-$C_5$ alkenyl, $C_2$-$C_5$ alkynyl, or (4-amino-2-methyl-5-pyrimindinyl)methyl.

2. The compound of claim 1 of formula (Ib) or a pharmaceutically acceptable salt thereof,

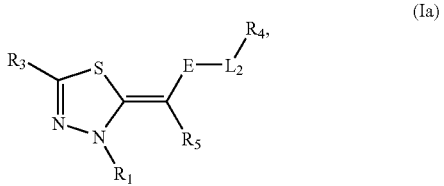

(Ia)

wherein $R_1$, $R_2$, $R_3$, $R_4$, $R_5$, E, and $L_2$ are as defined in claim 1.

3. The compound of claim 2 or a pharmaceutically acceptable salt thereof, wherein E is C(O) and $L_2$ is a bond.

4. The compound of claim 3 or a pharmaceutically acceptable salt thereof, wherein $R_1$ is $C_3$-$C_7$ alkyl, alkylcarbonylalkyl, arylcarbonyloxy-($C_2$-$C_6$ alkylene)-, alkoxy-($C_2$-$C_6$ alkylene)-, cycloalkylalkyl, haloalkyl, or heterocyclealkyl.

5. The compound of claim 4 or a pharmaceutically acceptable salt thereof, wherein $R_5$ is hydrogen or halogen.

6. The compound of claim 5 or a pharmaceutically acceptable salt thereof, wherein $R_4$ is $C_4$-$C_{10}$ alkyl, haloalkyl, naphthyl, arylalkyl, cycloalkyl, cycloalkylalkyl, heteroaryl, heterocycle, or substituted phenyl.

7. The compound of claim 2 or a pharmaceutically acceptable salt thereof, wherein
E is C(O);
$L_2$ is O;
$R_1$ is $C_3$-$C_7$ alkyl;
$R_5$ is hydrogen; and
$R_4$ is cycloalkyl, $C_4$-$C_{io}$ alkyl, or haloalkyl.

8. The compound of claim 2 or a pharmaceutically acceptable salt thereof, wherein
E is C(O);
$L_2$ is N($R_e$);
$R_e$ is hydrogen or alkyl;
$R_1$ is $C_3$-$C_7$ alkyl;
$R_5$ is hydrogen; and
$R_4$ is substituted phenyl.

9. The compound of claim 2 or a pharmaceutically acceptable salt thereof wherein $R_2$ and $R_3$ taken together with the carbon atoms to which they are attached form, a heteroaryl, a heterocycle, or a cycloalkenyl ring.

10. The compound of claim 1 of formula (Id) or a pharmaceutically acceptable salt thereof

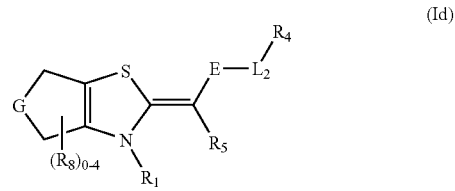

(Id)

wherein
G is N(H), N(alkyl), O, $CH_2$, or $CH_2CH_2$,
$R_8$ represents optional substituents selected from the group consisting of alkyl, halogen, and haloalkyl, two $R_8$ groups on the same carbon atom together with the carbon atom to which they are attached, optionally form a =O group, and
E, $R_1$, $R_4$, $R_5$, and $L_2$ are as set forth in claim 1.

11. The compound of claim 10 or a pharmaceutically acceptable salt thereof wherein G is O, $CH_2$, or $CH_2CH_2$.

12. The compound of claim 11 or a pharmaceutically acceptable salt thereof, wherein
E is C(O);
$L_2$ is a bond;
$R_5$ is hydrogen; and
$R_1$ is $C_3$-$C_7$ alkyl.

13. A compound or a pharmaceutically acceptable salt thereof selected from the group consisting of (2Z)-2-(3-butyl-4,5-dimethyl-1,3-thiazol-2(3H)-ylidene)-1-(5-chloro-2-methoxyphenyl)ethanone;

(2Z)-1-(1-adamantyl)-2-(3-butyl-4,5-dimethyl-1,3-thiazol-2(3H)-ylidene)ethanone;

tert-butyl (2Z)-(3-butyl-4,5-dimethyl-1,3-thiazol-2(3H)-ylidene)acetate;

(2Z)-1-(5-chloro-2-methoxyphenyl)-2-[3-(2-methoxyethyl)-4,5-dimethyl-1,3-thiazol-2(3H)-ylidene]ethanone;

(2Z)-2-(3-butyl-5-methyl-1,3-thiazol-2(3H)-ylidene)-1-(5-chloro-2-methoxyphenyl)ethanone;

(2Z)-2-(3-butyl-4,5-dimethyl-1,3-thiazol-2(3H)-ylidene)-1-cyclohexylethanone;

(2Z)-2-(3-butyl-4,5-dimethyl-1,3-thiazol-2(3H)-ylidene)-N-cyclohexylacetamide;

4-[(2Z)-2-(3-butyl-4,5-dimethyl-1,3-thiazol-2(3H)-ylidene)ethanoyl]morpholine;

(2Z)-2-(3-butyl-4,5-dimethyl-1,3-thiazol-2(3H)-ylidene)-N-(5-chloro-2-methoxyphenyl)acetamide;

(2Z)-1-(5-chloro-2-methoxyphenyl)-2-(3-propyl-1,3-benzothiazol-2(3H)-ylidene)ethanone;

(2Z)-2-(5-bromo-3-butyl-4-methyl-1,3-thiazol-2(3H)-ylidene)-1-(5-chloro-2-methoxyphenyl)ethanone;

(Z)-2-(5-acetyl-3-butyl-4-methylthiazol-2(3H)-ylidene)-1-(5-chloro-2-methoxyphenyl)ethanone;

(Z)-2-(3-butyl-5-(1-(hydroxyimino)ethyl)-4-methylthiazol-2(3H)-ylidene)-1-(5-chloro-2-methoxyphenyl) ethanone;

(2Z)-3-butyl-242-(5-chloro-2-methoxyphenyl)-2-oxoethylidene]-2,3-dihydro-1,3-thiazole-5-carbaldehyde;

(2Z)-3-butyl-242-(5-chloro-2-methoxyphenyl)-2-oxoethylidene]-2,3-dihydro-1,3-thiazole-5-carbaldehyde oxime;

(2Z)-1-(5-chloro-2-methoxyphenyl)-2-[4,5-dimethyl-3-(2-morpholin-4-ylethyl)- 1,3-thiazol-2(3H)-ylidene] ethanone;

(2Z)-3-butyl-2-(2-oxo-2-pyridin-2-ylethylidene)-2,3-dihydro-1,3-thiazole-5-carbaldehyde;
(2Z)-3-butyl-242-(3,5-difluorophenyl)-2-oxoethylidene]-2,3-dihydro-1,3-thiazole-5-carbaldehyde;
(2Z)-3-butyl-242-(2-fluorophenyl)-2-oxoethylidene]-2,3-dihydro-1,3-thiazole-5-carbaldehyde;
(2Z)-3-butyl-242-(2,4-difluorophenyl)-2-oxoethylidene]-2,3-dihydro-1,3-thiazole-5-carbaldehyde;
(2Z)-2-(3-butyl-4,5-dimethyl-1,3-thiazol-2(3H)-ylidene)-1-(2-fluorophenyl)ethanone;
(2Z)-2-(3-butyl-4,5-dimethyl-1,3-thiazol-2(3H)-ylidene)-1-pyridin-2-ylethanone;
(2Z)-2-(3-butyl-4,5-dimethyl-1,3-thiazol-2(3H)-ylidene)-1-(3,5-difluorophenyl)ethanone;
(2Z)-2-(3-butyl-3,4,5,6-tetrahydro-2H-cyclopenta[d][1,3]thiazol-2-ylidene)-1-(5-chloro-2-methoxyphenyl)ethanone;
(Z)-2-(5-acetyl-4-methyl-3-((tetrahydrofuran-2-yl)methyl)thiazol-2(3H)-ylidene)-1-(5-chloro-2-methoxyphenyl)ethanone;
(Z)-2-(5-acetyl-3-butyl-4-methylthiazole-2(3H)-ylidene-1-(pyridine-2-yl)ethanone;
(2Z)-2-(3-butyl-5-tert-butyl-4-methyl-1,3-thiazol-2(3H)-ylidene)-1-(3-chlorothien-2-yl)ethanone;
(2Z)-2-(3-butyl-5-tert-butyl-4-methyl-1,3-thiazol-2(3H)-ylidene)-1-(2-chloropyridin-3-yl)ethanone;
(2Z)-2-(3-butyl-5-tert-butyl-4-methyl-1,3-thiazol-2(3H)-ylidene)-1-cyclopentylethanone;
(2Z)-2-(3-butyl-5-tert-butyl-4-methyl-1,3-thiazol-2(3H)-ylidene)-1-cyclohexylethanone;
(2Z)-2-(3-butyl-5-tert-butyl-4-methyl-1,3-thiazol-2(3H)-ylidene)-1-(5-chloro-2-methoxyphenyl)ethanone;
6-[(2Z)-2-(3-butyl-5-tert-butyl-4-methyl-1,3-thiazol-2(3H)-ylidene)ethanoyl]-2,2-dimethyl-2,3-dihydro-4H-pyran-4-one;
(2Z)-1-(1-benzofuran-5-yl)-2-(3-butyl-5-tert-butyl-4-methyl-1,3-thiazol-2(3H)-ylidene)ethanone;
(2Z)-2-(3-butyl-5-tert-butyl-4-methyl-1,3-thiazol-2(3H)-ylidene)-1-(2,2-dimethyltetrahydro-2H-pyran-4-yl)ethanone;
(2Z)-2-(3-butyl-5-tert-butyl-4-methyl-1,3-thiazol-2(3H)-ylidene)-1-(5-fluoro-2-methoxyphenyl)ethanone;
(2Z)-2-(3-butyl-4-phenyl-1,3-thiazol-2(3H)-ylidene)-1-(5-chloro-2-methoxyphenyl)ethanone;
ethyl (2Z)-3-butyl-2-[2-(5-chloro-2-methoxyphenyl)-2-oxoethylidene]-2,3-dihydro-1,3-thiazole-4-carboxylate;
(2Z)-2-(3-butyl-5-tert-butyl-4-methyl-1,3-thiazol-2(3H)-ylidene)-N-(5-chloro-2-methoxyphenyl)acetamide;
(2Z)-2-(3-butyl-4-methyl-1,3-thiazol-2(3H)-ylidene)-1-cyclohexylethanone;
(2Z)-2-(3-butyl-4-methyl-1,3-thiazol-2(3H)-ylidene)-1-(3-chloro-l-benzothien-2-yl)ethanone;
(2Z)-1-(1-adamantyl)-2-(3-butyl-4-methyl-1,3-thiazol-2(3H)-ylidene)ethanone;
(2Z)-2-(3-butyl-4,5-dimethyl-1,3-thiazol-2(3H)-ylidene)-1-(2,6-difluorophenyl)ethanone;
(2Z)-2-(3-butyl-4,5-dimethyl-1,3-thiazol-2(3H)-ylidene)-1-(2,4-dichlorophenyl)ethanone;
(2Z)-2-(3-butyl-4,5-dimethyl-1,3-thiazol-2(3H)-ylidene)-1-[2-(trifluoromethyl)phenyl]ethanone;
(2Z)-2-(3-butyl-4,5-dimethyl-1,3-thiazol-2(3H)-ylidene)-1-[3-(trifluoromethyl)phenyl]ethanone;
(2Z)-2-(3-butyl-4,5-dimethyl-1,3-thiazol-2(3H)-ylidene)-1-cyclopentylethanone;
4-[(2Z)-2-(3-butyl-4,5-dimethyl-1,3-thiazol-2(3H)-ylidene)ethanoyl]benzonitrile;
(2Z)-2-(3-butyl-4,5-dimethyl-1,3-thiazol-2(3H)-ylidene)-1-(1-naphthyl)ethanone;
(2Z)-2-(3-butyl-4,5-dimethyl-1,3-thiazol-2(3H)-ylidene)-1-(2,5-difluorophenyl)ethanone;
(2Z)-2-(3-butyl-4,5-dimethyl-1,3-thiazol-2(3H)-ylidene)-1-pyridin-3-ylethanone;
(2Z)-1-(1,3-benzodioxo1-5-yl)-2-(3-butyl-4,5-dimethyl-1,3-thiazol-2(3H)-ylidene)ethanone;
(2Z)-2-(3-butyl-4,5-dimethyl-1,3-thiazol-2(3H)-ylidene)-1-(2-chloropyridin-3-yl)ethanone;
(2Z)-142,5-bis(trifluoromethyl)phenyl]-2-(3-butyl-4,5-dimethyl-1,3-thiazol-2(3H)-ylidene)ethanone;
(2Z)-2-(3-butyl-4,5-dimethyl-1,3-thiazol-2(3H)-ylidene)-1-[5-fluoro-2-(trifluoromethyl)phenyl]ethanone;
(2Z)-2-(3-butyl-4,5-dimethyl-1,3-thiazol-2(3H)-ylidene)-1-(3-methylthien-2-yl)ethanone;
(2Z)-2-(3-butyl-4,5-dimethyl-1,3-thiazol-2(3H)-ylidene)-1-(5-fluoro-2-methylphenyl)ethanone;
(2Z)-2-(3-butyl-4,5-dimethyl-1,3-thiazol-2(3H)-ylidene)-1-(5-chloro-2-fluorophenyl)ethanone;
(Z)-2-(3-butyl-54(E)-1-(methoxyimino)ethyl)-4-methylthiazol-2(3H)-ylidene)-1-(5-chloro-2-methoxyphenyl)ethanone;
(Z)-2-(3-butyl-54(Z)-1-(methoxyimino)ethyl)-4-methylthiazol-2(3H)-ylidene)-1-(5-chloro-2-methoxyphenyl)ethanone;
(2Z)-2-[3-butyl-4-(trifluoromethyl)-1,3-thiazol-2(3H)-ylidene]-1-(5-chloro-2-methoxyphenyl)ethanone;
(2Z)-2-[3-butyl-5-methyl-4-(trifluoromethyl)-1,3-thiazol-2(3H)-ylidene]-1-(5-chloro-2-methoxyphenyl)ethanone;
(Z)-1-(5-chloro-2-methoxyphenyl)-2-(54(E)-1-(methoxyimino)ethyl)-4-methyl-3-((tetrahydrofuran-2-yl)methyl)thiazol-2(3H)-ylidene)ethanone;
(Z)-1-(5-chloro-2-methoxyphenyl)-2-(54(Z)-1-(methoxyimino)ethyl)-4-methyl-3-((tetrahydrofuran-2-yl)methyl)thiazol-2(3H)-ylidene)ethanone;
(2Z)-3-butyl-242-(5-chloro-2-methoxyphenyl)-2-oxoethylidene]-5,5-dimethyl-2,3,5,6-tetrahydro-1,3-benzothiazol-7(4H)-one;
(2Z)-2-(3-butyl-5-tert-butyl-1,3-thiazol-2(3H)-ylidene)-1-(5-chloro-2-methoxyphenyl)ethanone;
(2Z)-2-(5-tert-butyl-3-isobutyl-1,3-thiazol-2(3H)-ylidene)-1-(5-chloro-2-methoxyphenyl)ethanone;
(2Z)-2[3-butyl-4-methyl-5-(2,2,2-trifluoro-1-hydroxy-1-methylethyl)-1,3-thiazol-2(3H)-ylidene]-1-(5-chloro-2-methoxyphenyl)ethanone;
(2Z)-2-[5-tert-butyl-3-(tetrahydrofuran-2-ylmethyl)-1,3-thiazol-2(3H)-ylidene]-1-(5-chloro-2-methoxyphenyl)ethanone;
(2Z)-1-(5-chloro-2-methoxyphenyl)-2-]3-isobutyl-5-methyl-4-(trifluoromethyl)-1,3-thiazol-2(3H)-ylidene]ethanone;
(2E)-2-(3-butyl-4-tert-butyl-1,3-thiazol-2(3H)-ylidene)-1-(5-chloro-2-methoxyphenyl)-2-fluoroethanone;
(2E)-2-(3-butyl-5-tert-butyl-1,3-thiazol-2(3H)-ylidene)-1-(5-chloro-2-methoxyphenyl)-2-fluoroethanone;
(2Z)-2-(3-butyl-5-isopropenyl-1,3-thiazol-2(3H)-ylidene)-1-(5-chloro-2-methoxyphenyl)ethanone;
(1Z)- 1-(3-butyl-4,5-dimethyl-1,3-thiazol-2(3H)-ylidene)-4,4-dimethylpentan-2-one;
1-[(2Z)-2-[2-(5-chloro-2-methoxyphenyl)-2-oxoethylidene]-4,5-dimethyl-1,3-thiazol-3(2H)-yl]-3,3-dimethylbutan-2-one;
1-adamantyl (2Z)-(3-butyl-4,5-dimethyl-1,3-thiazol-2(3H)-ylidene)acetate;

(2Z)-2[3-butyl-5-(3-hydroxy-3-methylbut-1ynyl)-4-methyl-1,3-thiazol-2(3H)-ylidene]-1-(5-chloro-2-methoxyphenyl)ethanone;
(1Z)-1-[3-(3,3-dimethyl-2-oxobutyl)-4,5-dimethyl-1,3-thiazol-2(3H)-ylidene]-4,4-dimethylpentan-2-one;
(2E)-2-(3-butyl-4,5-dimethyl-1,3-thiazol-2(3H)-ylidene)-1-(5-chloro-2-methoxyphenyl)-2-fluoroethanone;
2-[(2Z)-2-[2-(5-chloro-2-methoxyphenyl)-2-oxoethylidene]-4,5-dimethyl-1,3-thiazol-3(2H)-yl[ethyl 5-chloro-2-methoxybenzoate;
(2Z)-2-(3-butyl-4,5-dimethyl-1,3-thiazol-2(3H)-ylidene)-1-[2-(methylamino)phenyl]ethanone;
(2Z)-1-(5-chloro-2-methoxyphenyl)-2-[3-(4-fluorobutyl)-4,5-dimethyl-1,3-thiazol-2(3H)-ylidene]ethanone;
(2Z)-1-(2-amino-5-chlorophenyl)-2-(3-butyl-4,5-dimethyl-1,3-thiazol-2(3H)-ylidene)ethanone;
ethyl 2-[(2Z)-2-(3-butyl-4,5-dimethyl-1,3-thiazol-2(3H)-ylidene)ethanoyl]-4-chlorophenylcarbamate;
(2E)-2-(3-butyl-4,5-dimethyl-1,3-thiazol-2(3H)-ylidene)-1-(2-chloropyridin-3-yl)-2-fluoroethanone;
ethyl 2-[(2Z)-2-(3-butyl-4,5-dimethyl-1,3-thiazol-2(3H)-ylidene)ethanoyl]-4-chlorophenyl(methyl)carbamate;
methyl 2-[(2Z)-2-(3-butyl-4,5-dimethyl-1,3-thiazol-2(3H)-ylidene)ethanoyl]-4-chlorobenzoate;
(2Z)-2-[3-butyl-4-methyl-5-(2-methyl-1,3-dioxolan-2-yl)-1,3-thiazol-2(3H)-ylidene]-1-(5-chloro-2-methoxyphenyl)ethanone; 2,2,2-trichloro-1,1dimethylethyl (2Z)-(3-butyl-4,5-dimethyl-1,3-thiazol-2(3H)-ylidene)acetate;
(2Z)-2-[4-tert-butyl-3-(2-methoxyethyl)-1,3-thiazol-2(3H)-ylidene]-1-(5-chloro-2-methoxyphenyl)ethanone;
(2Z)-2-[4-tert-butyl-3-(tetrahydrofuran-2-ylmethyl)-1,3-thiazol-2(3H)-ylidene]-1-(5-chloro-2-methoxyphenyl)ethanone;
(2Z)-2[4-tert-butyl-3-(2-piperidin-1-ylethyl)-1,3-thiazol-2(3H)-ylidene]-1-(5-chloro-2-methoxyphenyl)ethanone;
(2Z)-3-butyl-2-[2-(5-chloro-2-methoxyphenyl)-2-oxoethylidene]-N-methyl-2,3-dihydro-1,3-thiazole-4-carboxamide;
(Z)-2-(5-acetyl-3-butylthiazol-2(3H)-ylidene)-1-(5-chloro-2-methoxyphenyl)ethanone;
(2Z)-2-(3-butyl-5-tert-butyl-1,3-thiazol-2(3H)-ylidene)-1-(2-chloropyridin-3-yl)ethanone;
(2Z)-2-(3-butyl-5-tert-butyl-1,3-thiazol-2(3H)-ylidene)-1-(5-fluoro-2-methoxyphenyl)ethanone;
(2Z)-2-(3-butyl-5-tert-butyl-1,3-thiazol-2(3H)-ylidene)-1-(3-chlorothien-2-yl)ethanone;
6-[(2Z)-2-(3-butyl-5-tert-butyl-1,3-thiazol-2(3H)-ylidene)ethanoyl]-2,2-dimethyl-2,3-dihydro-4H-pyran-4-one;
(2Z)-2-(3-butyl-5-tert-butyl-1,3-thiazol-2(3H)-ylidene)-1-(5-iodo-2-methoxyphenyl)ethanone;
(2Z)-1-(1-benzofuran-5-yl)-2-(3-butyl-5-tert-butyl-1,3-thiazol-2(3H)-ylidene)ethanone;
(2Z)-2-(3-butyl-5-tert-butyl-1,3-thiazol-2(3H)-ylidene)-1-(2-ethoxypyridin-3-yl)ethanone;
(2Z)-1-(1-benzofuran-5-yl)-2-(3-butyl-5-isopropenyl-1,3-thiazol-2(3H)-ylidene)ethanone;
(2Z)-2-(3-butyl-5-isopropenyl-1,3-thiazol-2(3H)-ylidene)-1-(2-ethoxypyridin-3-yl)ethanone;
(2Z)-2-(3-butyl-4-methyl-1,3-thiazol-2(3H)-ylidene)-1-[trans-2-phenylcyclopropyl]ethanone;
(2Z)-1-(5-chloro-2-methoxyphenyl)-2-[3-(cyclobutylmethyl)-5-(1-hydroxy-1-methylethyl)-4-methyl-1,3-thiazol-2(3H)-ylidene]ethanone;
(2Z)-2-[5-bromo-3-(cyclobutylmethyl)-4-methyl-1,3-thiazol-2(3H)-ylidene]-1-(5-chloro-2-methoxyphenyl)ethanone;
(2Z)-1-(5-chloro-2-methoxyphenyl)-2-[3-(cyclobutylmethyl)-1,3-thiazol-2(3H)-ylidene]ethanone;
(2Z)-1-(5-chloro-2-methoxyphenyl)-2-[3-(cyclobutylmethyl)-4-methyl-5-(2,2,2-trifluoro-1-hydroxy-1-methylethyl)-1,3-thiazol-2(3H)-ylidene]ethanone;
(2Z)-2[3-butyl-5-(1-hydroxy-1-methylethyl)-1,3-thiazol-2(3H)-ylidene]-1-(5-chloro-2-methoxyphenyl)ethanone;
(2Z)-1-(5-chloro-2-methoxyphenyl)-2-[3-(cyclobutylmethyl)-5-(1-hydroxy-1-methylethyl)-1,3-thiazol-2(3H)-ylidene]ethanone;
(2Z)-1-(5-chloro-2-methoxyphenyl)-2-[3-(cyclobutylmethyl)-5-(1-ethyl-1-hydroxypropyl)-4-methyl-1,3-thiazol-2(3H)-ylidene]ethanone;
(2Z)-1-(5-chloro-2-methoxyphenyl)-2-[3-(cyclobutylmethyl)-5-(2-fluoro-1-hydroxy-1-methylethyl)-4-methyl-1,3-thiazol-2(3H)-ylidene]ethanone;
(2Z)-1-(5-chloro-2-methoxyphenyl)-2-[3-(cyclobutylmethyl)-5-(2,2-difluoro-1-hydroxy-1-methylethyl)-4-methyl-1,3-thiazol-2(3H)-ylidene]ethanone;
(2Z)-2-(3-butyl-5-tert-butyl-1,3-thiazol-2(3H)-ylidene)-1-[2-(trifluoromethyl)phenyl]ethanone;
ethyl (2Z)-3-butyl-2-[2-(5-chloro-2-methoxyphenyl)-2-oxoethylidene]-5-(1-hydroxy-1-methylethyl)-2,3-dihydro-1,3-thiazole-4-carboxylate;
(2Z)-3-butyl-2-[2-(5-chloro-2-methoxyphenyl)-2-oxoethylidene]-6,6-dimethyl-3,6-dihydrofuro[3,4-d][1,3]thiazol-4(2H)-one;
(2Z)-2-(3-butyl-4,5-dimethyl-1,3-thiazol-2(3H)-ylidene)-1-(5-chloro-2-hydroxyphenyl)ethanone;
tert-butyl (2Z)-3-butyl-2-[2-(5-chloro-2-methoxyphenyl)-2-oxoethylidene]-2,3-dihydro-1,3-thiazol-4-ylcarbamate;
(2Z)-2-(3-butyl-4,5-dimethyl-1,3-thiazol-2(3H)-ylidene)-1-[5-chloro-2-(dimethylamino)phenyl]ethanone;
(2Z)-1-(5-chloro-2-methoxyphenyl)-2-[3-(cyclobutylmethyl)-5-(1-ethyl-1-hydroxypropyl)-1,3-thiazol-2(3H)-ylidene]ethanone;
(2Z)-2-[5-(1-amino-1-ethylpropyl)-3-(cyclobutylmethyl)-1,3-thiazol-2(3H)-ylidene]-1-(5-chloro-2-methoxyphenyl)ethanone;
(2Z)-2-(3-butyl-5-tert-butyl-1,3-thiazol-2(3H)-ylidene)-1-[6-chloro-4-(trifluoromethyl)pyridin-3-yl]ethanone;
(2Z)-3-butyl-2-[2-(5-chloro-2-methoxyphenyl)-2-oxoethylidene]-6,6-diethyl-2,3,5,6-tetrahydro-4H-pyrrolo[3,4-d][1,3]thiazol-4-one;
(2Z)-2-[3-butyl-5-[2-fluoro-1-(fluoromethyl)-1-hydroxyethyl]-1,3-thiazol-2(3H)-ylidene]-1-(5-chloro-2-methoxyphenyl)ethanone;
(2Z)-2-(3-butyl-5-isopropenyl-1,3-thiazol-2(3H)-ylidene)-1-[6-chloro-4-(trifluoromethyl)pyridin-3-yl]ethanone;
(2Z)-2[3-butyl-4-(1-hydroxy-1-methylethyl)-1,3-thiazol-2(3H)-ylidene]-1-(5-chloro-2-methoxyphenyl)ethanone;
(Z)-2-(4-acetyl-3-butylthiazol-2(3H)-ylidene)-1-(5-chloro-2-methoxyphenyl)ethanone;
(2Z)-1-(5-chloro-2-methoxyphenyl)-2-[3-(cyclobutylmethyl)-5-[2-fluoro-1-(fluoromethyl)-1-hydroxyethyl]-4-methyl-1,3-thiazol-2(3H)-ylidene]ethanone;
ethyl (2Z)-5-(1-amino-1-methylethyl)-3-butyl-2-[2-(5-chloro-2-methoxyphenyl)-2-oxoethylidene]-2,3-dihydro-1,3-thiazole-4-carboxylate;

(2Z)-3-butyl-2[2-(5-chloro-2-methoxyphenyl)-2-oxoethylidene]-6,6-dimethyl-2,3,5,6-tetrahydro-4H-pyrrolo[3,4-d][1,3]thiazol-4-one; and (Z)-2-(3-butyl-4,5-dimethylthiazol-2(3H)-ylidene)-1-(5-chloro-2-methoxyphenyl)ethanethione.

14. A pharmaceutical composition comprising a therapeutically effective amount of a compound of claim 1 of formula (I), or a pharmaceutically acceptable salt thereof, in combination with one or more pharmaceutically acceptable carrier.

15. A method for treating pain in a mammal in need of such treatment comprising administering to the mammal a therapeutically effective amount of a compound of claim 1 of formula (I), or a pharmaceutically acceptable salt thereof.

* * * * *